(12) United States Patent
Kretschmer et al.

(10) Patent No.: US 10,674,727 B2
(45) Date of Patent: Jun. 9, 2020

(54) SUBSTITUTED OXADIAZOLES FOR COMBATING PHYTOPATHOGENIC FUNGI

(71) Applicant: BASF SE, Ludwigshafen (DE)

(72) Inventors: Manuel Kretschmer, Washington, DC (US); Christine Wiebe, Ludwigshafen (DE); Wassilios Grammenos, Ludwigshafen (DE); Ana Escribano Cuesta, Ludwigshafen (DE); Maria Angelica Quintero Palomar, Limburgerhof (DE); Ian Robert Craig, Ludwigshafen (DE); Marcus Fehr, Limburgerhof (DE); Tobias Mentzel, Limburgerhof (DE); Bernd Mueller, Ludwigshafen (DE); Christian Harald Winter, Navi Mumbai (IN); Violeta Terteryan-Seiser, Ludwigshafen (DE); Jan Klaas Lohmann, Ludwigshafen (DE); Erica Cambeis, Ludwigshafen (DE); Thomas Grote, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 82 days.

(21) Appl. No.: 15/777,470

(22) PCT Filed: Nov. 16, 2016

(86) PCT No.: PCT/EP2016/077819
§ 371 (c)(1),
(2) Date: May 18, 2018

(87) PCT Pub. No.: WO2017/085100
PCT Pub. Date: May 26, 2017

(65) Prior Publication Data
US 2018/0368409 A1   Dec. 27, 2018

(30) Foreign Application Priority Data
Nov. 19, 2015   (EP) ..................... 15195439

(51) Int. Cl.
*A01N 43/82*  (2006.01)
*C07D 271/06*  (2006.01)
*C07D 413/10*  (2006.01)
*C07D 413/12*  (2006.01)

(52) U.S. Cl.
CPC ........... *A01N 43/82* (2013.01); *C07D 271/06* (2013.01); *C07D 413/10* (2013.01); *C07D 413/12* (2013.01)

(58) Field of Classification Search
None
See application file for complete search history.

(56) References Cited

U.S. PATENT DOCUMENTS

| | | | |
|---|---|---|---|
| 4,243,409 | A | 1/1981 | Schmidt et al. |
| 4,871,753 | A | 10/1989 | Rohr |
| 2003/0224936 | A1 | 12/2003 | Kretzschmar |
| 2018/0265483 | A1 | 9/2018 | Stierli et al. |
| 2018/0273494 | A1 | 9/2018 | Stierli et al. |
| 2018/0325114 | A1 | 11/2018 | Terteryan-Seiser et al. |

FOREIGN PATENT DOCUMENTS

| | | |
|---|---|---|
| CL | 2018001348 A1 | 6/2018 |
| CL | 2018000832 A1 | 7/2018 |
| CL | 2018000834 A1 | 7/2018 |
| CN | 1927860 A | 3/2007 |
| CN | 101468985 A | 7/2009 |
| DE | 2801509 A1 | 7/1979 |
| DE | 19536811 A1 | 4/1997 |
| EP | 0276432 A2 | 8/1988 |
| EP | 0393936 B1 | 2/1995 |
| EP | 1329160 A2 | 7/2003 |
| EP | 3165093 A1 | 5/2017 |
| EP | 3165094 A1 | 5/2017 |

(Continued)

OTHER PUBLICATIONS

European Search Report for EP Patent Application No. 15195439.3, dated Feb. 24, 2016.
International Search Report for PCT Patent Application No. PCT/EP2016/077819, dated Jan. 2, 2017.
International Preliminary Report on Patentability for PCT Patent Application No. PCT/EP2016/077819, dated May 22, 2018.
Office Action, issued in co-pending U.S. Appl. No. 15/777,281, dated Jan. 8, 2019.
Database Registry [online], Chemical Abstracts Service, Columbus, Ohio, US, XP002754059, Jul. 6, 2015, retrieved from STN Database accession No. 1795437-67-0.

(Continued)

*Primary Examiner* — Alton N Pryor
(74) *Attorney, Agent, or Firm* — Marshall, Gerstein & Borun LLP

(57) ABSTRACT

The present invention relates the use of the compounds of the formula I

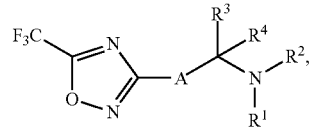

or the N-oxides, or the agriculturally acceptable salts thereof for combating phytopathogenic harmful fungi, wherein the variables are defined as given in the description and claims. Further present invention relates to novel compounds, to mixtures comprising at least one such compound of the formula I and at least one further pesticidally active substance selected from the group consisting of herbicides, safeners, fungicides, insecticides, and plant growth regulators; and to agrochemical compositions comprising at least one such compound of the formula I and to agrochemical compositions further comprising seeds.

10 Claims, No Drawings

(56) References Cited

FOREIGN PATENT DOCUMENTS

| | | | |
|---|---|---|---|
| EP | 3167716 A1 | 5/2017 |
| JP | 2001316378 A2 | 11/2001 |
| WO | 9405153 A1 | 3/1994 |
| WO | 9715576 A1 | 5/1997 |
| WO | 199715576 A1 | 5/1997 |
| WO | 97/30047 A1 | 8/1997 |
| WO | WO2002023986 | * | 3/2002 |
| WO | 2003059903 A2 | 7/2003 |
| WO | WO2003074495 | * | 9/2003 |
| WO | 04020445 A2 | 3/2004 |
| WO | 2005040152 A1 | 5/2005 |
| WO | 2006102645 A1 | 9/2006 |
| WO | 2009019656 A1 | 2/2009 |
| WO | 2010072602 A1 | 7/2010 |
| WO | 201088181 A2 | 8/2010 |
| WO | 2011/088181 A1 | 7/2011 |
| WO | 2011/088192 A1 | 7/2011 |
| WO | 2012100342 A1 | 8/2012 |
| WO | 2013/008162 A1 | 1/2013 |
| WO | 2013/009830 A1 | 1/2013 |
| WO | 2013006408 A1 | 1/2013 |
| WO | 2013017657 A1 | 2/2013 |
| WO | 2013/064079 A1 | 5/2013 |
| WO | 13066839 A2 | 5/2013 |
| WO | 2013066835 A2 | 5/2013 |
| WO | WO-2013066838 A1 | * | 5/2013 |
| WO | 2013080120 A1 | 6/2013 |
| WO | 2014062549 A1 | 4/2014 |
| WO | 15086462 A1 | 6/2015 |
| WO | 15173050 A1 | 11/2015 |
| WO | 15181035 A1 | 12/2015 |
| WO | 15185485 A1 | 12/2015 |
| WO | 15185708 A1 | 12/2015 |
| WO | 15189035 A1 | 12/2015 |
| WO | 15197458 A1 | 12/2015 |
| WO | 16055404 A1 | 4/2016 |
| WO | 16142224 A1 | 9/2016 |
| WO | 16156129 A1 | 10/2016 |
| WO | 16166020 A1 | 10/2016 |
| WO | 17016915 A1 | 2/2017 |
| WO | 2017/055469 A1 | 4/2017 |
| WO | 2017/055473 A1 | 4/2017 |
| WO | 17055587 A1 | 4/2017 |
| WO | 17060148 A1 | 4/2017 |
| WO | 17067784 A1 | 4/2017 |
| WO | 2017/076739 A1 | 5/2017 |
| WO | 2017/076740 A1 | 5/2017 |
| WO | 2017/076742 A1 | 5/2017 |
| WO | 2017/076757 A1 | 5/2017 |
| WO | 2017/076935 A1 | 5/2017 |
| WO | 2017/081309 A1 | 5/2017 |
| WO | 2017/081310 A1 | 5/2017 |
| WO | 2017/081311 A1 | 5/2017 |
| WO | 2017/081312 A1 | 5/2017 |
| WO | 2017/085098 A1 | 5/2017 |
| WO | 2017/085100 A1 | 5/2017 |
| WO | 17093019 A1 | 6/2017 |
| WO | 17093120 A1 | 6/2017 |
| WO | 17093167 A1 | 6/2017 |
| WO | 2017/148797 A1 | 9/2017 |
| WO | 2017/178245 A1 | 10/2017 |
| WO | 2017/211649 A1 | 12/2017 |
| WO | 2017/211650 A1 | 12/2017 |
| WO | 2017/211652 A1 | 12/2017 |

OTHER PUBLICATIONS

Database Registry [online], Chemical Abstracts Service, Columbus, Ohio, US, XP002754060, Jul. 6, 2015, retrieved from STN Database accession No. 1795431-65-0.

Database Registry [online], Chemical Abstracts Service, Columbus, Ohio, US, XP002754061, Apr. 18, 2014, retrieved from STN Database accession No. 1586975-57-6.

Database Registry [online], Chemical Abstracts Service, Columbus, Ohio, US, XP002754062, Apr. 18, 2014, retrieved from STN Database accession No. 1586674-00-1.

Andrianov et al., "Rearrangements of 1-oxa-2-azoles. 4. Synthesis and Rearrangement of Amidoximes of Isoxazole—and 4,5-Dihydroisoxazole-3-Carboxylic Acids," CAS Accession No. 1992:6493.

Goddard, "5-Heteroaryl-2-Thiophenecarboxylic Acids: Oxazoles and Oxadiazoles," Journal of Heterocyclic Chemistry, 1991, vol. 28, No. 17, pp. 17-28, CAS Accession No. 1991:185346.

Hemming, "Product Class 6: 1,2,4-Oxadiazoles," Science of Synthesis, pp. 127-184, CAS Accession No. 2004:204619.

Liu et al., "Design, Synthesis, and Biological Evaluation of N-Carboxyphenylpyrrole Derivatives as Potent HIV Fusion Inhibitors Targeting gp41," CAS Accession No. 2008:1411348.

Tale et al., "Synthesis and Antibacterial, Antifungal Activity of Novel 1,2,4-Oxadiazole," Journal of Chemical and Pharmaceutical Research, 2011, vol. 3, No. 2, pp. 496-505, CAS Accession No. 2011:495843.

Database CA [online], Chemical Abstracts Service, Columbus, Ohio, US, Xie et al., "Preparation of 5-[3-(heteroaryl) phenyl]tetrazole Derivatives as for Treating or Preventing HIV Infection," XP002753544, retrieved from STN Database accession No. 2009:804990.

Hynes et al. "Hydroxylamine Derivatives as Potential Antimalarial Agents. 3. 1,2,4-Oxadiazoles," Journal of Medicinal Chemistry, vol. 15, Issue 11, (1972), pp. 1198-1200.

Remy et al., "Prolintane Metabolites. Synthesis of dl-1-(.alpha.-propylphenethyl)pyrrolidin-2-one," Journal of Medical Chemistry, vol. 15, Issue 11, (1972), p. 1198.

Office Action dated Jan. 8, 2019 in U.S. Appl. No. 15/775,429, filed May 11, 2018.

Office Action dated Jan. 8, 2019 in U.S. Appl. No. 15/775,434, filed May 11, 2018.

* cited by examiner

SUBSTITUTED OXADIAZOLES FOR COMBATING PHYTOPATHOGENIC FUNGI

This application is a National Stage application of International Application No. PCT/EP2016/077819, filed Nov. 16, 2016. This application also claims priority under 35 U.S.C. § 119 to European Patent Application No. 15195439.3, filed Nov. 19, 2015.

The present invention relates to the use oxadiazoles of the formula I, or an N-oxide and/or their agriculturally useful for controlling phytopathogenic fungi, or to a method for combating phytopathogenic harmful fungi, which process comprises treating the fungi or the materials, plants, the soil or seeds to be protected against fungal attack, with an effective amount of at least one compound of the formula I, or an N-oxide, or an agriculturally acceptable salt thereof; the present invention also relates to mixtures comprising at least one such compound of the formula I and at least one further pesticidally active substance selected from the group consisting of herbicides, safeners, fungicides, insecticides, and plant growth regulators; and to agrochemical compositions comprising at least one such compound of the formula I and to agrochemical compositions further comprising seeds.

EP 276432 A2 relates to 3-phenyl-5-trifluoromethyloxadiazole derivatives and to their use to combat phytopathogenic microorganisms. WO 2013/008162 describes trifluoromethyl-oxadiazole derivatives with HDAC4 inhibitory activity and their medical use, particularly in the treatment of Huntington's disease, muscle atrophy and diabetes/metabolic syndrome. WO11088192, WO 2011088181 describes the medicinal use of trifluoromethyl-oxadiazole derivatives. A use for controlling phytopathogenic fungi is not described. WO 2015/185485 was published after the date of filing of the present application and describes the use of certain substituted oxadiazoles for combating phytopathogenic fungi In many cases, in particular at low application rates, the fungicidal activity of known fungicidal compounds is unsatisfactory. Based on this, it was an objective of the present invention to provide compounds having improved activity and/or a broader activity spectrum against phytopathogenic fungi. This objective is achieved by the oxadiazoles of the formula I and/or their agriculturally useful salts for controlling phytopathogenic fungi.

Accordingly, the present invention relates to the use of the compounds of the formula I

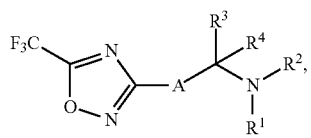

wherein:
A is phenyl or a 5- or 6-membered aromatic heterocycle, wherein the ring member atoms of the heterocyclic ring include besides carbon atoms 1, 2, 3 or 4 heteroatoms selected from N, O and S as ring member atoms; and wherein the cyclic groups A are unsubstituted or substituted by 1, 2, 3 or 4 identical or different groups $R^A$; wherein
$R^A$ is halogen, cyano, $NO_2$, OH, $NH_2$, SH, $C_1$-$C_6$-alkyl, $C_1$-$C_6$-alkoxy, $C_1$-$C_6$-alkylthio, $C_1$-$C_6$-alkylsulfinyl, $C_1$-$C_6$-alkylsulfonyl, $C_2$-$C_6$-alkenyl, $C_2$-$C_6$-alkynyl, $C_3$-$C_8$-cycloalkyl or $C_3$-$C_8$-cycloalkoxy; and wherein any of the aliphatic or cyclic moieties are unsubstituted or substituted by 1, 2, 3 or 4 identical or different groups $R^a$; wherein
$R^a$ is halogen, cyano, $NO_2$, OH, SH, $NH_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio or $C_3$-$C_8$-cycloalkyl;
$R^1$, $R^2$ independently of each other are hydrogen, $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkenyl, C(=O)—($C_1$-$C_6$-alkyl), C(=O)—($C_1$-$C_6$-alkoxy), phenyl-$C_1$-$C_4$-alkyl, heteroaryl-$C_1$-$C_4$-alkyl, phenyl, naphthyl or a 3- to 10-membered saturated, partially unsaturated or aromatic mono- or bicyclic heterocycle, wherein the ring member atoms of said mono- or bicyclic heterocycle include besides carbon atoms further 1, 2, 3 or 4 heteroatoms selected from N, O and S as ring member atoms and wherein 1 or 2 carbon ring member atoms of the heterocycle may be replaced by 1 or 2 groups independently selected from C(=O) and C(=S); and wherein the heteroaryl group in heteroaryl-$C_1$-$C_4$-alkyl is a 5- or 6-membered aromatic heterocycle, wherein the ring member atoms of the heterocyclic ring include besides carbon atoms 1, 2, 3 or 4 heteroatoms selected from N, O and S as ring member atoms; and wherein any of the above-mentioned aliphatic or cyclic groups are unsubstituted or substituted by 1, 2, 3 or up to the maximum possible number of identical or different groups $R^{1a}$; or
$R^1$ and $R^2$ together with the nitrogen atom to which they are bound form a saturated or partially unsaturated mono- or bicyclic 3- to 7-membered heterocycle, wherein the heterocycle includes beside one nitrogen atom and one or more carbon atoms no further heteroatom or 1, 2 or 3 further heteroatoms independently selected from N, O and S as ring member atoms; and wherein one or two $CH_2$ groups of the heterocycle may be replaced by one or two groups independently selected from the group of C(=O) and C(=S); and wherein the heterocycle is unsubstituted or carries 1, 2, 3, 4 or up to the maximum possible number of identical or different groups $R^{1a}$; wherein
$R^{1a}$ is halogen, cyano, $NO_2$, OH, SH, $NH_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $NHSO_2$—$C_1$-$C_4$-alkyl, (C=O)—($C_1$-$C_4$-alkyl), C(=O)—($C_1$-$C_4$-alkoxy) or $C_1$-$C_6$-alkylsulfonyl;
$R^3$ is H, $C_1$-$C_4$-alkyl, $C_1$-$C_4$-haloalkyl;
$R^4$ is H, $C_1$-$C_4$-alkyl, $C_1$-$C_4$-haloalkyl;
or the N-oxides, or the agriculturally acceptable salts thereof for combating phytopathogenic harmful fungi.

Agriculturally acceptable salts of the compounds of the formula I encompass especially the salts of those cations or the acid addition salts of those acids whose cations and anions, respectively, have no adverse effect on the fungicidal action of the compounds I. Suitable cations are thus in particular the ions of the alkali metals, preferably sodium and potassium, of the alkaline earth metals, preferably calcium, magnesium and barium, of the transition metals, preferably manganese, copper, zinc and iron, and also the ammonium ion which, if desired, may carry one to four $C_1$-$C_4$-alkyl substituents and/or one phenyl or benzyl substituent, preferably diisopropylammonium, tetramethylammonium, tetrabutylammonium, trimethylbenzylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium. Anions of acceptable acid addition salts are primarily chloride, bromide, fluoride, hydrogensulfate, sulfate, dihydrogenphosphate, hydrogenphosphate, phosphate, nitrate, bicarbonate, carbonate, hexafluorosilicate, hexafluorophosphate, benzoate, and the anions of $C_1$-$C_4$-alkanoic acids, preferably formate, acetate, propionate and butyrate. They can be formed by reacting a compound I with an acid of the corresponding anion, preferably of hydrochloric acid, hydrobromic acid, sulfuric acid, phosphoric acid or nitric acid.

Compounds of the formula I can exist as one or more stereoisomers. The various stereoisomers include enantiomers, diastereomers, atropisomers arising from restricted rotation about a single bond of asymmetric groups and geometric isomers. They also form part of the subject matter of the present invention. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, e.g. a racemate, individual stereoisomers, or as an optically active form.

Compounds of the formula I can be present in different crystal modifications whose biological activity may differ. They also form part of the subject matter of the present invention. In respect of the variables, the embodiments of the intermediates obtained during preparation of compounds I correspond to the embodiments of the compounds of formula I. The term "compounds I" refers to compounds of formula I.

In the definitions of the variables given above, collective terms are used which are generally representative for the substituents in question. The term "$C_n$-$C_m$" indicates the number of carbon atoms possible in each case in the substituent or substituent moiety in question.

The moieties having two ore more possibilities to be attached apply following:

The moieties having no brackets in the name are bonded via the last moiety e.g. $C_2$-$C_6$-alkenyloxyimino-$C_1$-$C_4$-alkyl is bonded via $C_1$-$C_4$-alkyl, heteroaryl-$C_1$-$C_4$-alkyl is bonded via $C_1$-$C_4$-alkyl etc.

The moieties having brackets in the name are bonded via the first moiety e.g. C(=O)—($C_1$-$C_6$-alkyl) is bonded via C=O as indicated by the number valence of the carbon atom, etc.

The term "halogen" refers to fluorine, chlorine, bromine and iodine.

The term "$C_1$-$C_6$-alkyl" refers to a straight-chained or branched saturated hydrocarbon group having 1 to 6 carbon atoms, for example methyl, ethyl, propyl, 1-methylethyl, butyl, 1-methylpropyl, 2-methylpropyl, and 1,1-dimethylethyl.

The term "$C_1$-$C_6$-haloalkyl" refers to a straight-chained or branched alkyl group having 1 to 6 carbon atoms (as defined above), wherein some or all of the hydrogen atoms in these groups may be replaced by halogen atoms as mentioned above, for example chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, $CH_2$—$C_2F_5$, $CF_2$—$C_2F_5$, $CF(CF_3)_2$, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl.

The term "$C_1$-$C_6$-alkoxy" refers to a straight-chain or branched alkyl group having 1 to 6 carbon atoms (as defined above) which is bonded via an oxygen, at any position in the alkyl group, for example methoxy, ethoxy, n-propoxy, 1-methylethoxy, butoxy, 1-methylpropoxy, 2-methylpropoxy or 1,1-dimethylethoxy.

The term "$C_1$-$C_6$-haloalkoxy" refers to a $C_1$-$C_6$-alkoxy group as defined above, wherein some or all of the hydrogen atoms may be replaced by halogen atoms as mentioned above, for example, $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, $OC_2F_5$, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$—$C_2F_5$, $OCF_2$—$C_2F_5$, 1-($CH_2F$)-2-fluoroethoxy, 1-($CH_2Cl$)-2-chloroethoxy, 1-($CH_2Br$)-2-bromo¬ethoxy, 4-fluorobutoxy, 4-chlorobutoxy, 4-bromobutoxy or nonafluorobutoxy. The terms "phenyl-$C_1$-$C_4$-alkyl or heteroaryl-$C_1$-$C_4$-alkyl" refer to alkyl having 1 to 4 carbon atoms (as defined above), wherein one hydrogen atom of the alkyl radical is replaced by a phenyl or hetereoaryl radical respectively.

The term "$C_1$-$C_4$-alkoxy-$C_1$-$C_4$-alkyl" refers to alkyl having 1 to 4 carbon atoms (as defined above), wherein one hydrogen atom of the alkyl radical is replaced by a $C_1$-$C_4$-alkoxy group (as defined above). Likewise, the term "$C_1$-$C_4$-alkylthio-$C_1$-$C_4$-alkyl" refers to alkyl having 1 to 4 carbon atoms (as defined above), wherein one hydrogen atom of the alkyl radical is replaced by a $C_1$-$C_4$-alkylthio group.

The term "$C_1$-$C_6$-alkylthio" as used herein refers to straight-chain or branched alkyl groups having 1 to 6 carbon atoms (as defined above) bonded via a sulfur atom. Accordingly, the term "$C_1$-$C_6$-haloalkylthio" as used herein refers to straight-chain or branched haloalkyl group having 1 to 6 carbon atoms (as defined above) bonded through a sulfur atom, at any position in the haloalkyl group.

The term "$C_1$-$C_6$-alkylsulfinyl" refers to straight-chain or branched alkyl groups having 1 to 6 carbon atoms (as defined above) bonded through a —S(=O)— moiety, at any position in the alkyl group, for example methylsulfinyl and ethylsulfinyl, and the like. Accordingly, the term "$C_1$-$C_6$-haloalkylsulfinyl" refers to straight-chain or branched haloalkyl group having 1 to 6 carbon atoms (as defined above), bonded through a —S(=O)— moiety, at any position in the haloalkyl group.

The term "$C_1$-$C_6$-alkylsulfonyl" refers to straight-chain or branched alkyl groups having 1 to 6 carbon atoms (as defined above), bonded through a —S(=O)$_2$— moiety, at any position in the alkyl group, for example methylsulfonyl. Accordingly, the term "$C_1$-$C_6$-haloalkylsulfonyl" refers to straight-chain or branched haloalkyl group having 1 to 6 carbon atoms (as defined above), bonded through a —S(=O)$_2$— moiety, at any position in the haloalkyl group.

The term "hydroxy$C_1$-$C_4$-alkyl" refers to alkyl having 1 to 4 carbon atoms, wherein one hydrogen atom of the alkyl radical is replaced by a OH group.

The term "aminoC$_1$-C$_4$-alkyl" refers to alkyl having 1 to 4 carbon atoms, wherein one hydrogen atom of the alkyl radical is replaced by a NH$_2$ group.

The term "C$_1$-C$_4$-alkylamino-C$_1$-C$_4$-alkyl" refers to refers to alkyl having 1 to 4 carbon atoms (as defined above), wherein one hydrogen atom of the alkyl radical is replaced by a C$_1$-C$_4$-alkyl-NH— group which is bound through the nitrogen. Likewise the term "diC$_1$-C$_4$-alkylamino-C$_1$-C$_4$-alkyl" refers to refers to alkyl having 1 to 4 carbon atoms (as defined above), wherein one hydrogen atom of the alkyl radical is replaced by a (C$_1$-C$_4$-alkyl)$_2$N— group which is bound through the nitrogen.

The term "aminocarbonyl-C$_1$-C$_4$-alkyl" refers to alkyl having 1 to 4 carbon atoms, wherein one hydrogen atom of the alkyl radical is replaced by a —(C=O)—NH$_2$ group.

The term "C$_2$-C$_6$-alkenyl" refers to a straight-chain or branched unsaturated hydrocarbon radical having 2 to 6 carbon atoms and a double bond in any position, such as ethenyl, 1-propenyl, 2-propenyl (allyl), 1-methylethenyl, 1-butenyl, 2-butenyl, 3-butenyl, 1-methyl-1-propenyl, 2-methyl-1-propenyl, 1-methyl-2-propenyl, 2-methyl-2-propenyl.

The term "C$_2$-C$_6$-alkynyl" refers to a straight-chain or branched unsaturated hydrocarbon radical having 2 to 6 carbon atoms and containing at least one triple bond, such as ethynyl, 1-propynyl, 2-propynyl (propargyl), 1-butynyl, 2-butynyl, 3-butynyl, 1-methyl-2-propynyl.

The term "C$_3$-C$_8$-cycloalkyl" refers to monocyclic saturated hydrocarbon radicals having 3 to 8 carbon ring members such as cyclopropyl (C$_3$H$_5$), cyclobutyl, cyclopentyl, cyclohexyl, cycloheptyl or cyclooctyl.

The term "C$_3$-C$_8$-cycloalkyloxy" refers to a cycloalkyl radical having 3 to 8 carbon atoms (as defined above), which is bonded via an oxygen.

The term "C(=O)—(C$_1$-C$_4$-alkyl)" refers to a radical which is attached through the carbon atom of the C(=O) group as indicated by the number valence of the carbon atom.

The term "aliphatic" refers to compounds or radicals composed of carbon and hydrogen and which are non-aromatic compounds. An alicyclic compound or radical is an organic compound that is both aliphatic and cyclic. They contain one or more all-carbon rings which may be either saturated or unsaturated, but do not have aromatic character.

The terms "cyclic moiety" or "cyclic group" refer to a radical which is an alicyclic ring or an aromatic ring, such as, for example, phenyl or heteroaryl.

The term "and wherein any of the aliphatic or cyclic groups are unsubstituted or substituted by 1, 2, 3, 4 or up to the maximum possible number of identical or different groups Ria" refers to aliphatic groups, cyclic groups and groups, which contain an aliphatic and a cyclic moiety in one group, such as in, for example, phenyl-C$_1$-C$_4$-alkyl; therefore a group which contains an aliphatic and a cyclic moiety both of these moieties may be substituted or unsubstituted independently of each other.

The term "heteroaryl" refers to aromatic monocyclic or polycyclic ring systems incuding besides carbon atoms, 1, 2, 3 or 4 heteroatoms independently selected from the group consisting of N, O and S.

The term "phenyl" refers to an aromatic ring systems incuding six carbon atoms (commonly referred to as benzene ring). In association with the group A the term "phenyl" is to be interpreted as a benzene ring or phenylene ring, which is attached to both, the oxadiazole moiety and the —CR$^3$R$^4$— group.

The term "saturated or partially unsaturated 3-, 4-, 5-, 6- or 7-membered carbocycle" is to be understood as meaning both saturated or partially unsaturated carbocycles having 3, 4, 5, 6 or 7 ring members. Examples include cyclopropyl, cyclopentyl, cyclopentenyl, cyclopentadienyl, cyclohexyl, cyclohexenyl, cyclohexadienyl, cycloheptyl, cycloheptenyl, cycloheptadienyl, and the like.

The term "3- to 10-membered saturated, partially unsaturated or aromatic mono- or bicyclic heterocycle, wherein the ring member atoms of said mono- or bicyclic heterocycle include besides carbon atoms further 1, 2, 3 or 4 heteroatoms selected from N, O and S as ring member atoms", is to be understood as meaning both, aromatic mono- and bicyclic heteroaromatic ring systems, and also saturated and partially unsaturated heterocycles, for example:

a 3- or 4-membered saturated heterocycle which contains 1 or 2 heteroatoms from the group consisting of N, O and S as ring members such as oxirane, aziridine, thiirane, oxetane, azetidine, thiethane, [1,2]dioxetane, [1,2]dithietane, [1,2]diazetidine; and a 5- or 6-membered saturated or partially unsaturated heterocycle which contains 1, 2 or 3 heteroatoms from the group consisting of N, O and S as ring members such as 2-tetrahydro-furanyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl and also the corresponding -ylidene radicals; and a 7-membered saturated or partially unsaturated heterocycle such as tetra- and hexahydroazepinyl, such as 2,3,4,5-tetrahydro[1H]azepin-1-,-2-,-3-,-4-,-5-,-6- or -7-yl, 3,4,5,6-tetrahydro[2H]azepin-2-,-3-,-4-,-5-,-6- or -7-yl, 2,3,4,7-tetrahydro[1H]azepin-1-,-2-,-3-,-4-,-5-,-6-or -7-yl, 2,3,6,7-tetrahydro[1H]azepin-1-,-2-,-3-,-4-,-5-,-6- or -7-yl, hexahydroazepin-1-,-2-,-3- or -4-yl, tetra- and hexahydrooxepinyl such as 2,3,4,5-tetrahydro[1H]oxepin-2-,-3-,-4-,-5-,-6- or -7-yl, 2,3,4,7-tetrahydro[1H]oxepin-2-,-3-,-4-,-5-,-6- or -7-yl, 2,3,6,7-tetrahydro[1H]oxepin-2-, -3-,-4-,-5-,-6- or -7-yl, hexahydroazepin-1-,-2-,-3- or -4-yl, tetra- and hexahydro-1,3-diazepinyl, tetra- and hexahydro-1,4-diazepinyl, tetra- and hexahydro-1,3-oxazepinyl, tetra- and hexahydro-1,4-oxazepinyl, tetra- and hexahydro-1,3-dioxepinyl, tetra- and hexahydro-1,4-dioxepinyl and the corresponding -ylidene radicals; and the term "5- or 6-membered heteroaryl" or the term "5- or 6-membered aromatic heterocycle" refers to aromatic ring systems incuding besides carbon atoms, 1, 2, 3 or 4 heteroatoms independently selected from the group consisting of N, O and S, for example, a 5-membered heteroaryl such as pyrrol-1-yl, pyrrol-2-yl, pyrrol-3-yl, thien-2-yl, thien-3-yl, furan-2-yl, furan-3-yl, pyrazol-1-yl, pyrazol-3-yl, pyrazol-4-yl, pyrazol-5-yl, imidazol-1-yl, imidazol-2-yl, imidazol-4-yl, imidazol-5-yl, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, 1,2,4-triazolyl-1-yl, 1,2,4-triazol-3-yl1,2,4-triazol-5-yl, 1,2,4-oxadiazol-3-yl, 1,2,4-oxadiazol-5-yl and 1,2,4-thiadiazol-3-yl, 1,2,4-thiadiazol-5-yl; or a 6-membered heteroaryl, such as pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl and 1,3,5-triazin-2-yl and 1,2,4-triazin-3-yl.

In respect of the variables, the embodiments of the intermediates correspond to the embodiments of the compounds I. Preference is given to those compounds I and, where applicable, also to compounds of all sub-formulae provided herein, wherein all variables have independently of each other or more preferably in combination (any possible combination of 2 or more substituents as defined herein) the following meanings:

In one aspect of the invention A is phenyl which is unsubstituted or substituted by 1, 2, 3 or 4 identical or different groups $R^4$ as defined or preferably defined herein and wherein the group —$C(R^3R^4)$—$NR^1R^2$ is attached to the phenyl ring in para-position with regard to the trifluoromethyloxadiazole group.

In one aspect of the invention A is phenyl which is unsubstituted or substituted by 1, 2, 3 or 4 identical or different groups $R^4$ as defined or preferably defined herein and wherein the group —$C(R^3R^4)$—$NR^1R^2$ is attached to the phenyl ring in meta-position with regard to the trifluoromethyloxadiazole group.

In a further aspect of the invention A is phenyl which is substituted by 1 or 2 identical or different groups $R^4$ as defined or preferably defined herein and wherein the group —$C(R^3R^4)$—$NR^1R^2$ is attached to the phenyl ring in pars-position with regard to the trifluoromethyloxadiazole group.

In another aspect of the invention A is phenyl which is unsubstituted and wherein the group —$C(R^3R^4)$—$NR^1R^2$ is attached to the phenyl ring in pars-position with regard to the trifluoromethyloxadiazole group.

In a preferred embodiment of the invention A is phenyl substituted by $R^4$ selected from halogen, or $C_1$-$C_6$-alkyl. In a further preferred embodiment of the invention A is phenyl substituted by halogen. In a special preferred embodiment of the invention A is phenyl substituted by F. In a further special preferred embodiment of the invention A is phenyl substituted by Cl.

In a further preferred embodiment of the invention A is phenyl substituted by $C_1$-$C_6$-alkyl. In a special preferred embodiment of the invention A is phenyl substituted by $CH_3$. In a further special preferred embodiment of the invention A is phenyl substituted by $CH_2CH_3$. In a further special preferred embodiment of the invention A is phenyl which is unsubstituted.

In one embodiment A is a 6-membered aromatic heterocycle, wherein the ring member atoms of the aromatic heterocycle include besides carbon atoms 1 or 2 nitrogen atoms as ring member atoms; and wherein the aromatic heterocyclic ring is unsubstituted or substituted by 1 or 2 identical or different groups $R^4$ as defined or preferably defined herein.

In a further embodiment A is a 6-membered aromatic heterocycle, wherein the ring member atoms of the aromatic heterocycle include besides carbon atoms 1 or 2 nitrogen atoms as ring member atoms; and wherein the aromatic heterocycle is unsubstituted or substituted by 1 or 2 identical or different groups $R^4$ as defined or preferably defined herein and wherein the group —$C(R^3R^4)$—$NR^1R^2$ is attached to the 6-membered aromatic heterocycle in pars-position with regard to the trifluoromethyloxadiazole group.

In a further embodiment A is a 6-membered aromatic heterocycle, wherein the ring member atoms of the aromatic heterocycle include besides carbon atoms 1 or 2 nitrogen atoms as ring member atoms; and wherein the aromatic heterocycle is unsubstituted or substituted by 1 or 2 identical or different groups $R^4$ as defined or preferably defined herein and wherein the group —$C(R^3R^4)$—$NR^1R^2$ is attached to the 6-membered aromatic heterocycle in meta-position with regard to the trifluoromethyloxadiazole group.

In a further embodiment A is a 6-membered aromatic heterocycle, wherein the ring member atoms of the aromatic heterocycle include besides carbon atoms 1 or 2 nitrogen atoms as ring member atoms; and wherein the aromatic heterocycle is unsubstituted or substituted by 1 or 2 identical or different groups $R^4$ as defined or preferably defined herein and wherein the group —$C(R^3R^4)$—$NR^1R^2$ is attached to the 6-membered aromatic heterocycle in ortho-position with regard to the trifluoromethyloxadiazole group.

In a further embodiment A is a 6-membered aromatic heterocycle, wherein the ring member atoms of the aromatic heterocycle include besides carbon atoms 1 or 2 nitrogen atoms as ring member atoms; and wherein the aromatic heterocycle is unsubstituted and wherein the group —$C(R^3R^4)$—$NR^1R^2$ is attached to the 6-membered aromatic heterocycle in pars-position with regard to the trifluoromethyloxadiazole group.

In a further preferred embodiment A is a 5-membered aromatic heterocycle, wherein the ring member atoms of the heterocycle include besides carbon atoms 1, 2, 3 or 4 heteroatoms selected from N, O and S as ring member atoms; and wherein the cyclic groups A are unsubstituted or substituted by 1 or 2 identical or different groups $R^4$ as defined or preferably defined herein.

In a further preferred embodiment A is a 5-membered aromatic heterocycle, wherein the ring member atoms of the heterocycle include besides carbon atoms 1, 2, 3 or 4 heteroatoms selected from N, O and S as ring member atoms; and wherein the cyclic groups A are unsubstituted.

In one embodiment the invention relates to the use of compounds of the formula I, or the N-oxides, or the agriculturally acceptable salts thereof for combating phytopathogenic harmful fungi, wherein the cyclic moiety A is defined as in subformulae (A.1) to (A.12),

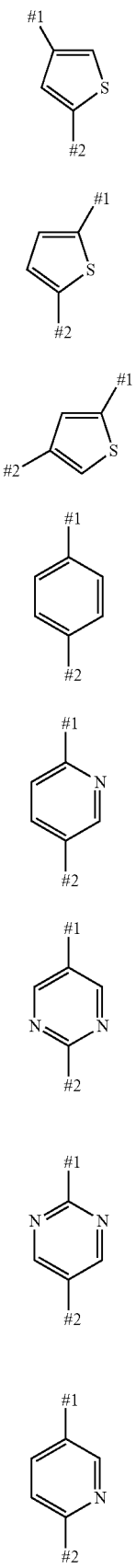

wherein #1 denotes the position which is bound to the trifluoromethyloxadiazole moiety and #2 denotes the position, which is connected to the —C(R$^3$R$^4$)—NR$^1$R$^2$ group of compounds of the formula I; and wherein the cyclic moiety A is unsubstituted or substituted by 1 or 2 identical or different groups R$^A$ and wherein R$^A$ is as defined or preferably defined herein. In another embodiment the cyclic moieties A as defined in any one of subformulae (A.1) to (A.12) is unsubstituted or substituted by 1 or 2 identical or different groups R$^A$; and wherein R$^A$ is chlorine, fluorine or methyl. In a preferred embodiment the cyclic moiety A as defined in any one of subformulae (A.1) to (A.12) is unsubstituted.

In a preferred embodiment of the invention R$^A$ is halogen, cyano, $C_1$-$C_6$-alkyl, $C_1$-$C_6$-alkoxy, $C_2$-$C_6$-alkenyl, $C_2$-$C_6$-alkynyl or $C_3$-$C_8$-cycloalkyl; and wherein any of the aliphatic and cyclic moieties are unsubstituted or substituted by 1, 2, 3, 4 or up to the maximum possible number of identical or different groups R$^a$ as defined or preferably defined herein.

In another preferred embodiment of the invention R$^A$ is halogen, cyano, $C_1$-$C_6$-alkyl, $C_1$-$C_6$-alk-oxy, $C_2$-$C_6$-alkenyl, $C_2$-$C_6$-alkynyl or $C_3$-$C_8$-cycloalkyl; and wherein any of the the aliphatic and cyclic moieties are unsubstituted or substituted by 1, 2, 3, 4 or up to the maximum possible number of identical or different groups selected from halogen, cyano, $C_1$-$C_6$-alkyl, $C_1$-$C_6$-alkoxy and $C_3$-$C_8$-cycloalkyl; in particular fluorine.

More preferably R$^A$ is halogen, cyano, $C_1$-$C_6$-alkyl, $C_1$-$C_6$-haloalkyl, $C_1$-$C_6$-alkoxy or $C_1$-$C_6$-haloalkoxy; in particular halogen, $C_1$-$C_6$-alkyl; more particularly R$^A$ is chlorine, fluorine or methyl.

In a more preferable embodiment R$^A$ is chlorine, fluorine or methyl.

R$^a$ according to the invention is halogen, cyano, NO$_2$, OH, SH, NH$_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio or $C_3$-$C_8$-cycloalkyl. In a preferred embodiment of the invention $R^a$ is halogen, cyano, $C_1$-$C_6$-alkyl, $C_1$-$C_6$-alkoxy or $C_3$-$C_8$-cycloalkyl. More preferably $R^a$ is halogen, in particular fluorine.

According to one embodiment $R^1$ is H. According to one embodiment $R^1$ is $C_1$-$C_6$-alkyl, preferably methyl, ethyl, n-propyl, i-propyl, n-butyl, i-butyl, t-butyl, in particular methyl, ethyl. According to a further embodiment $R^1$ is $C_2$-$C_6$-alkenyl, preferably ethylene. According to a further embodiment $R^1$ is $C_2$-$C_6$-alkynyl, preferred ethynyl, 1-propynyl. According to a further embodiment $R^1$ is $C_3$-$C_8$-cycloalkyl, preferrably cyclopropyl, cyclobutyl, cyclopentyl, in particular cyclopropyl, cyclopentyl or cyclohexyl.

According to one embodiment $R^1$ is $C_1$-$C_6$-alkyl substituted by halogen, preferably methyl, ethyl, n-propyl, i-propyl, n-butyl, i-butyl, t-butyl, in particular methyl, ethyl. In a special embodiment of the invention $R^1$ is $CF_3$.

According to one embodiment $R^1$ is C(=O)—($C_1$-$C_6$-alkyl). According to one embodiment $R^1$ is C(=O)—($C_1$-$C_6$-alkyl), wherein alkyl is preferably methyl, ethyl, n-propyl, i-propyl, n-butyl, i-butyl, t-butyl, in particular methyl, ethyl. According to one embodiment $R^1$ is C(=O)—($C_1$-$C_6$-alkoxy), wherein alkoxy is preferrably methoxy, ethoxy, n-propoxy, i-propoxy, n-butoxy, i-butoxy, t-butoxy. According to one embodiment $R^1$ is phenyl-$C_1$-$C_4$-alkyl, wherein alkyl is preferably methyl, ethyl, n-propyl, i-propyl, n-butyl, i-butyl, t-butyl, in particular methyl, ethyl.

According to one embodiment $R^1$ is heteroaryl-$C_1$-$C_4$-alkyl, wherein alkyl is preferably methyl, ethyl, n-propyl, i-propyl, n-butyl, i-butyl, t-butyl, in particular methyl, ethyl and wherein heteroaryl is furan, thiophen, pyrazol, isoxazol, imidazole, oxazol, thiazol, triazol, oxydiazol, pyrol, pyriminin.

According to one embodiment $R^1$ is phenyl. According to a further embodiment $R^1$ is benzyl.

According to a further embodiment $R^1$ is naphthyl. According to one embodiment $R^1$ 3- to 10-membered saturated, partially unsaturated or aromatic mono- or bicyclic heterocycle, wherein the ring member atoms of said mono- or bicyclic heterocycle include besides carbon atoms further 1, 2, 3 or 4 heteroatoms selected from N, O and S as ring member atoms and wherein 1 or 2 carbon ring member atoms of the heterocycle may be replaced by 1 or 2 groups independently selected from C(=O) and C(=S); and wherein the heteroaryl group in heteroaryl-$C_1$-$C_4$-alkyl is a 5- or 6-membered aromatic heterocycle, wherein the ring member atoms of the heterocyclic ring include besides carbon atoms 1, 2, 3 or 4 heteroatoms selected from N, O and S as ring member atoms especially, furan, thiophen, pyrazol, isoxazol, imidazole, oxazol, thiazol, triazol, oxydiazol, pyrol, pyriminin.

According to a further embodiment the above mentioned groups may carry one, two, three or four identical or different substituents selected from the group consisting of methyl, ethyl, propyl, butyl, preferably methyl. According to a further embodiment the above mentioned groups may carry one, two, three or four identical or different substituents selected from the group consisting of partially or fully halogenated methyl, ethyl, propyl, butyl, preferably partially or fully halogenated methyl, in particular $CF_3$. According to a further embodiment the above mentioned groups may carry one, two, three or four identical or different substituents selected from the group consisting of methoxy, ethoxy, propoxy, butoxy, preferably methoxy. According to a further embodiment the above mentioned groups may carry one, two, three or four identical or different substituents selected from the group consisting of partially or fully halogenated methoxy, ethoxy, propoxy, butoxy, preferably partially or fully halogenated methoxy, in particular $OCF_3$. In a special embodiment of the invention, $R^1$ is phenyl. In a further special embodiment of the invention, $R^1$ is phenyl substituted by Cl, F, Br, I, $CH_3$, $OCH_3$, $CF_3$ or $OCF_3$. In a further special embodiment of the invention, $R^1$ is benzyl substituted by Cl, F, Br, I, $CH_3$, $OCH_3$, $CF_3$ or $OCF_3$. In a further special embodiment $R^1$ is naphtyl substituted by Cl, F, Br, I, $CH_3$, $OCH_3$, $CF_3$ or $OCF_3$. In a further special embodiment of the invention, $R^1$ is thiophene substituted by Cl, F, Br, I, $CH_3$, $OCH_3$, $CF_3$ or $OCF_3$. In a further special embodiment of the invention, $R^1$ is pyrol substituted by Cl, F, Br, I, $CH_3$, $OCH_3$, $CF_3$ or $OCF_3$. In a further special embodiment of the invention, $R^1$ is pyrazol substituted by Cl, F, Br, I, $CH_3$, $OCH_3$, $CF_3$ or $OCF_3$. In a further special embodiment of the invention, $R^1$ is pyrimidin substituted by Cl, F, Br, I, $CH_3$, $OCH_3$, $CF_3$ or $OCF_3$. In a further special embodiment of the invention, $R^1$ is oxydiazol substituted by Cl, F, Br, I, CHs, $OCH_3$, $CF_3$ or $OCF_3$.

In a preferred embodiment $R^1$ is H, $C_1$-$C_6$-alkyl, $C_3$-$C_6$-cycloalkyl. In a special preferred embodiment $R^1$ is H, CHs, cyclopropyl.

According to one embodiment $R^2$ is H. According to one embodiment $R^2$ is $C_1$-$C_6$-alkyl, preferably methyl, ethyl, n-propyl, i-propyl, n-butyl, i-butyl, t-butyl, in particular methyl, ethyl. According to a further embodiment $R^2$ is $C_2$-$C_6$-alkenyl, preferably ethylene. According to a further embodiment $R^2$ is $C_2$-$C_6$-alkynyl, preferred ethynyl, 1-propynyl. According to a further embodiment $R^2$ is $C_3$-$C_8$-cycloalkyl, preferrably cyclopropyl, cyclobutyl, cyclopentyl, in particular cyclopropyl, cyclopentyl or cyclohexyl.

According to one embodiment $R^2$ is $C_1$-$C_6$-alkyl substituted by halogen, preferably methyl, ethyl, n-propyl, i-propyl, n-butyl, i-butyl, t-butyl, in particular methyl, ethyl. In a special embodiment of the invention, $R^2$ is $CF_3$.

According to one embodiment $R^2$ is C(=O)—($C_1$-$C_6$-alkyl). According to one embodiment $R^2$ is C(=O)—($C_1$-$C_6$-alkyl), wherein alkyl is preferably methyl, ethyl, n-propyl, i-propyl, n-butyl, i-butyl, t-butyl, in particular methyl, ethyl. According to one embodiment $R^2$ is C(=O)—($C_1$-$C_6$-alkoxy), wherein alkoxy is preferrably methoxy, ethoxy, n-propoxy, i-propoxy, n-butoxy, i-butoxy, t-butoxy.

According to one embodiment $R^2$ is phenyl-$C_1$-$C_4$-alkyl, wherein alkyl is preferably methyl, ethyl, n-propyl, i-propyl, n-butyl, i-butyl, t-butyl, in particular methyl, ethyl.

According to one embodiment $R^2$ is heteroaryl-$C_1$-$C_4$-alkyl, wherein alkyl is preferably methyl, ethyl, n-propyl, i-propyl, n-butyl, i-butyl, t-butyl, in particular methyl, ethyl and wherein heteroaryl is furan, thiophen, pyrazol, isoxazol, imidazole, oxazol, thiazol, triazol, oxydiazol, pyrol, pyriminin.

According to one embodiment $R^2$ is phenyl. According to a further embodiment $R^2$ is benzyl. According to a further embodiment $R^2$ is naphthyl. According to one embodiment $R^2$ is a 3- to 10-membered saturated, partially unsaturated or aromatic mono- or bicyclic heterocycle, wherein the ring member atoms of said mono- or bicyclic heterocycle include besides carbon atoms further 1, 2, 3 or 4 heteroatoms selected from N, O and S as ring member atoms and wherein 1 or 2 carbon ring member atoms of the heterocycle may be replaced by 1 or 2 groups independently selected from C(=O) and C(=S); and wherein the heteroaryl group in heteroaryl-$C_1$-$C_4$-alkyl is a 5- or 6-membered aromatic heterocycle, wherein the ring member atoms of the heterocyclic ring include besides carbon atoms 1, 2, 3 or 4 heteroatoms selected from N, O and S as ring member atoms especially, furan, thiophen, pyrazol, isoxazol, imidazole, oxazol, thiazol, triazol, oxydiazol, pyrol, pyrimidin.

According to a further embodiment the above mentioned groups may carry one, two, three or four identical or different substituents selected from the group consisting of methyl, ethyl, propyl, butyl, preferably methyl. According to a further embodiment the above mentioned groups may carry one, two, three or four identical or different substituents selected from the group consisting of partially or fully halogenated methyl, ethyl, propyl, butyl, preferably partially or fully halogenated methyl, in particular $CF_3$. According to a further embodiment the above mentioned groups may carry one, two, three or four identical or different substituents selected from the group consisting of methoxy, ethoxy, propoxy, butoxy, preferably methoxy. According to a further embodiment the above mentioned groups may carry one, two, three or four identical or different substituents selected from the group consisting of partially or fully halogenated methoxy, ethoxy, propoxy, butoxy, preferably partially or fully halogenated methoxy, in particular $OCF_3$. In a special embodiment of the invention, $R^2$ is phenyl. In a further special embodiment of the invention, $R^2$ is phenyl substituted by Cl, F, Br, I, $CH_3$, $OCH_3$, $CF_3$ or $OCF_3$. In a further special embodiment of the invention, $R^2$ is benzyl substituted by Cl, F, Br, I, $CH_3$, $OCH_3$, $CF_3$ or $OCF_3$. In a further special embodiment $R^2$ is naphtyl substituted by Cl, F, Br, I, $CH_3$, $OCH_3$, $CF_3$ or $OCF_3$. In a further special embodiment of the invention, $R^2$ is thiophene substituted by Cl, F, Br, I, $CH_3$, $OCH_3$, $CF_3$ or $OCF_3$. In a further special embodiment of the invention, $R^2$ is pyrol substituted by Cl, F, Br, I, $CH_3$, $OCH_3$, $CF_3$ or $OCF_3$. In a further special embodiment of the invention, $R^2$ is pyrazol substituted by Cl, F, Br, I, $CH_3$, $OCH_3$, $CF_3$ or $OCF_3$. In a further special embodiment of the invention, $R^2$ is pyrimidin substituted by Cl, F, Br, I, $CH_3$, $OCH_3$, $CF_3$ or $OCF_3$. In a further special embodiment of the invention, $R^2$ is oxydiazol substituted by Cl, F, Br, I, $CH_3$, $OCH_3$, $CF_3$ or $OCF_3$.

In a preferred embodiment $R^2$ is H, $C_1$-$C_6$-alkyl, $C_2$-$C_6$-alkenyl, $C_2$-$C_6$-alkynyl, $C_3$-$C_6$-cycloalkyl, phenyl-$C_1$-$C_4$-alkyl, heteroaryl-$C_1$-$C_4$-alkyl, phenyl. In a special preferred embodiment $R^2$ is H, $C_1$-$C_6$-alkyl, $C_3$-$C_6$-cycloalkyl, phenyl-$C_1$-$C_4$-alkyl, heteroaryl-$C_1$-$C_4$-alkyl, phenyl. In a further special preferred embodiment $R^2$ is H, $C_1$-$C_6$-alkyl, $C_3$-$C_6$-cycloalkyl, phenyl-$C_1$-$C_4$-alkyl, phenyl. In a further special preferred embodiment $R^2$ is H, $CH_3$, $CH_2CH_3$, cyclopropyl, phenyl, benzyl. In another preferred embodiment $R^1$ is hydrogen, $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkenyl, phenyl-$C_1$-$C_4$-alkyl, heteroaryl-$C_1$-$C_4$-alkyl, phenyl or a 3- to 10-membered saturated, partially unsaturated mono- or bicyclic heterocycle, wherein the ring member atoms of said mono- or bicyclic heterocycle include besides carbon atoms further 1, 2, 3 or 4 heteroatoms selected from N, O and S as ring member atoms and wherein 1 or 2 carbon ring member atoms of the heterocycle may be replaced by 1 or 2 groups independently selected from C(=O) and C(=S); and wherein the heteroaryl group in heteroaryl-$C_1$-$C_4$-alkyl is a 5- or 6-membered aromatic heterocycle, wherein the ring member atoms of the heterocyclic ring include besides carbon atoms 1, 2, 3 or 4 heteroatoms selected from N, O and S as ring member atoms; and wherein any of the above-mentioned aliphatic or cyclic groups are unsubstituted or substituted by 1, 2, 3 or up to the maximum possible number of identical or different groups $R^{1a}$; wherein $R^{1a}$ is halogen, cyano, $NO_2$, OH, SH, $NH_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $NHSO_2$—$C_1$-$C_4$-alkyl, (C=O)—($C_1$-$C_4$-alkyl), C(=O)—($C_1$-$C_4$-alkoxy) or $C_1$-$C_6$-alkylsulfonyl; and wherein $R^2$ is C(=O)—($C_1$-$C_6$-alkyl) or C(=O)—($C_1$-$C_6$-alkoxy). In a further embodiment $R^1$ and $R^2$ independently of each other are hydrogen, $C_1$-$C_6$-alkyl, $C_2$-$C_6$-alkenyl, $C_2$-$C_6$-alkynyl, $C_3$-$C_8$-cycloalkyl, C(=O)—($C_1$-$C_6$-alkyl), C(=O)—($C_1$-$C_6$-alkoxy), phenyl-$C_1$-$C_4$-alkyl or phenyl; and wherein the aliphatic and the cyclic groups are unsubstituted or substituted by 1, 2, 3, 4 or up to the maximum possible number of identical or different groups $R^{1a}$ as defined herein.

In another embodiment $R^1$ is hydrogen, $C_1$-$C_6$-alkyl, $C_2$-$C_6$-alkenyl or $C_2$-$C_6$-alkynyl and $R^2$ is hydrogen, $C_1$-$C_6$-alkyl, $C_2$-$C_6$-alkenyl, $C_2$-$C_6$-alkynyl, $C_3$-$C_8$-cycloalkyl, phenyl-$C_1$-$C_4$-alkyl, heteroaryl-$C_1$-$C_4$-alkyl, phenyl or heteroaryl; and wherein the heteroaryl group is a 5- or 6-membered aromatic heterocycle, wherein the ring includes besides carbon atoms 1, 2, 3 or 4 heteroatoms selected from N, O and S as ring member atoms; and wherein any of the aliphatic or cyclic groups are unsubstituted or substituted by 1, 2, 3, 4 or up to the maximum possible number of identical or different groups $R^{1a}$ as defined or preferably defined herein.

In one aspect of the invention $R^1$ and $R^2$ independently of each other are hydrogen, $C_1$-$C_6$-alkyl, $C_2$-$C_6$-alkenyl, $C_2$-$C_6$-alkynyl, $C_3$-$C_8$-cycloalkyl, C(=O)—($C_1$-$C_6$-alkyl) or C(=O)—($C_1$-$C_6$-alkoxy); and wherein any of the aliphatic or cyclic groups are unsubstituted or substituted by 1, 2, 3, 4 or up to the maximum possible number of identical or different groups $R^{1a}$ as defined or preferably defined herein.

In another embodiment $R^1$ is hydrogen, $C_1$-$C_6$-alkyl, $C_2$-$C_6$-alkenyl, $C_2$-$C_6$-alkynyl or $C_3$-$C_8$-cycloalkyl and $R^2$ is C(=O)—($C_1$-$C_6$-alkyl) or C(=O)—($C_1$-$C_6$-alkoxy); and wherein any of the aliphatic or cyclic groups are unsubstituted or substituted by 1, 2, 3, 4 or up to the maximum possible number of identical or different groups $R^{1a}$ as defined or preferably defined herein.

In another embodiment $R^1$ is hydrogen, $C_1$-$C_6$-alkyl, $C_2$-$C_6$-alkenyl, $C_2$-$C_6$-alkynyl or $C_3$-$C_8$-cycloalkyl and $R^2$ is C(=O)—($C_1$-$C_6$-alkyl); and wherein any of the aliphatic or cyclic groups are unsubstituted or substituted by 1, 2, 3, 4 or up to the maximum possible number of identical or different radicals selected from the group fluorine, chlorine and methyl.

In one aspect of the invention $R^1$ and $R^2$ independently of each other are hydrogen, $C_1$-$C_6$-alkyl, $C_2$-$C_6$-alkenyl, $C_2$-$C_6$-alkynyl, $C_3$-$C_8$-cycloalkyl; and wherein any of the aliphatic or cyclic groups are unsubstituted or substituted by 1, 2, 3, 4 or up to the maximum possible number of identical or different groups $R^{1a}$ as defined or preferably defined herein.

In a further aspect of the invention $R^1$ is hydrogen, $C_1$-$C_6$-alkyl, $C_2$-$C_6$-alkenyl or $C_2$-$C_6$-alkynyl and $R^2$ is phenyl-$C_1$-$C_4$-alkyl, heteroaryl-$C_1$-$C_4$-alkyl, phenyl or heteroaryl; and wherein the heteroaryl group is a 5- or 6-membered aromatic heterocycle wherein the ring includes besides carbon atoms 1, 2, 3 or 4 heteroatoms selected from N, O and S as ring member atoms; and wherein any of the aliphatic or cyclic groups are unsubstituted or substituted by 1, 2, 3, 4 or up to the maximum possible number of identical or different groups $R^{1a}$ as defined or preferably defined herein.

In a further aspect of the invention $R^1$ is hydrogen, $C_1$-$C_6$-alkyl, $C_2$-$C_6$-alkenyl or $C_2$-$C_6$-alkynyl and $R^2$ is phenyl-$C_1$-$C_4$-alkyl, heteroaryl-$C_1$-$C_4$-alkyl or phenyl; and wherein the heteroaryl group is a 5- or 6-membered aromatic heterocycle wherein the ring includes besides carbon atoms 1, 2, 3 or 4 heteroatoms selected from N, O and S as ring member atoms; and wherein any of the aliphatic or cyclic groups are unsubstituted or substituted by 1, 2, 3, 4 or up to the maximum possible number of identical or different groups $R^{1a}$ as defined or preferably defined herein.

In one embodiment $R^1$ is hydrogen or $C_1$-$C_4$-alkyl and $R^2$ is $C_3$-$C_8$-cycloalkyl, wherein the cycloalkyl group is unsubstituted or carries 1, 2, 3, 4 or up to the maximum possible number of identical or different groups $R^{1a}$ as defined or preferably defined herein.

In one embodiment $R^1$ is hydrogen or $C_1$-$C_4$-alkyl and $R^2$ is $C_1$-$C_6$-alkyl, $C_2$-$C_6$-alkenyl or $C_2$-$C_6$-alkynyl, wherein the aliphatic groups are unsubstituted or carry 1, 2, 3, 4 or up to the maximum possible number of identical or different groups $R^{1a}$ as defined or preferably defined herein.

In one embodiment $R^1$ is hydrogen or $C_1$-$C_4$-alkyl and $R^2$ is phenyl, a 5- or 6-membered aromatic heterocycle, phenyl-$C_1$-$C_4$-alkyl or heteroaryl-$C_1$-$C_4$-alkyl, wherein the ring member atoms of the heterocyclic ring include besides carbon atoms 1, 2, 3 or 4 heteroatoms selected from N, O and S as ring member atoms; and wherein any of the cyclic groups are unsubstituted or substituted by 1, 2, 3, 4 or up to the maximum possible number of identical or different groups $R^{1a}$ as defined or preferably defined herein.

In one embodiment $R^1$ is hydrogen or $C_1$-$C_4$-alkyl and $R^2$ is phenyl-$C_1$-$C_4$-alkyl or heteroaryl-$C_1$-$C_4$-alkyl; wherein the heteroaryl group is a 5- or 6-membered aromatic heterocycle, wherein the ring member atoms of the aromatic heterocycle include besides carbon atoms 1, 2, 3 or 4 heteroatoms selected from N, O and S as ring member atoms; wherein any of the aliphatic or cyclic groups are unsubstituted or substituted by 1, 2, 3, 4 or up to the maximum possible number of identical or different groups $R^{1a}$ as defined or preferably defined herein.

In one embodiment $R^1$ is hydrogen or $C_1$-$C_4$-alkyl and $R^2$ is phenyl or a 5- or 6-membered aromatic heterocycle, wherein the ring member atoms of the heterocyclic ring include besides carbon atoms 1, 2, 3 or 4 heteroatoms selected from N, O and S as ring member atoms; and wherein any of the cyclic groups are unsubstituted or substituted by 1, 2, 3, 4 or up to the maximum possible number of identical or different groups $R^{1a}$ as defined or preferably defined herein.

In one embodiment of the invention $R^1$ and $R^2$ together with the nitrogen atom to which they are bound form a saturated or partially unsaturated mono- or bicyclic 3- to 7-membered heterocycle, wherein the heterocycle includes beside one nitrogen atom and one or more carbon atoms 1, 2 or 3 heteroatoms independently selected from N, O and S as ring member atoms; and wherein one or two CH$_2$ groups of the heterocycle may be replaced by one or two groups independently selected from the group of C(=O) and C(=S); and wherein the heterocycle is unsubstituted or carries 1, 2, 3, 4 or up to the maximum possible number of identical or different groups $R^{1a}$; wherein $R^{1a}$ is halogen, cyano, NO$_2$, OH, SH, NH$_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, NHSO$_2$—$C_1$-$C_4$-alkyl, (C=O)—$C_1$-$C_4$-alkyl, C(=O)—$C_1$-$C_4$-alkoxy or $C_1$-$C_6$-alkylsulfonyl.

In one embodiment of the invention $R^1$ and $R^2$ together with the N atom to which it is bound form a saturated or partially unsaturated 3- to 6-membered heterocycle, wherein the heterocycle includes beside one nitrogen atom and one or more carbon atoms no further heteroatoms.

In one embodiment of the invention $R^1$ and $R^2$ together with the N to which it is bound form a saturated or partially unsaturated 3- to 6-membered heterocycle, wherein one or two CH$_2$ groups of the heterocycle may be replaced by one or two groups independently selected from the group of C(=O) and C(=S). In one embodiment $R^1$ and $R^2$ together with the nitrogen atom to which they are bound form a saturated or partially unsaturated monocyclic 5- to 7-membered heterocycle, wherein the heterocycle includes beside one nitrogen atom and one or more carbon atoms no further heteroatom or 1 or 2 heteroatoms independently selected from N, O and S as ring member atoms; and wherein one or two CH$_2$ groups of the heterocycle may be replaced by one or two groups independently selected from the group of C(=O) and C(=S); and wherein the heterocycle is unsubstituted or carries 1, 2, 3, 4 or up to the maximum possible number of identical or different groups $R^{1a}$ as defined or preferably defined herein; particularly $R^{1a}$ is halogen or $C_1$-$C_6$-alkyl.

In a further embodiment $R^1$ and $R^2$ together with the nitrogen atom to which they are bound form a saturated or partially unsaturated monocyclic 5- or 6-membered heterocycle, wherein the heterocycle includes beside one nitrogen atom and one or more carbon atoms no further heteroatom or 1 further heteroatom independently selected from N, O and S as ring member atoms; and wherein one or two CH$_2$ groups of the heterocycle may be replaced by one or two groups independently selected from the group of C(=O) and C(=S); and wherein the heterocycle is unsubstituted or carries 1, 2, 3, 4 or up to the maximum possible number of identical or different groups $R^{1a}$ as defined or preferably defined herein; particularly $R^{1a}$ is halogen or In one embodiment of the invention $R^{1a}$ is halogen, cyano, $C_1$-$C_6$-haloalkyl, $C_1$-$C_6$-alkoxy, $C_1$-$C_6$-haloalkoxy. In another preferred aspect of the invention $R^{1a}$ is fluorine, chlorine, cyano, methyl, methoxy, trifluoromethyl, trifluoromethoxy, difluoromethyl or difluoromethoxy. In a more preferred aspect of the invention $R^{1a}$ is halogen or $C_1$-$C_6$-alkyl; particularly fluorine, chlorine or methyl.

In one special preferred embodiment of the invention $R^1$ and $R^2$ together with the N atom to which it is bound form a aziridinyl.

In one special preferred embodiment of the invention $R^1$ and $R^2$ together with the N atom to which it is bound form a azetidinyl.

In one special preferred embodiment of the invention $R^1$ and $R^2$ together with the N atom to which it is bound form a 1-pyrrolidinyl.

In one special preferred embodiment of the invention $R^1$ and $R^2$ together with the N atom to which it is bound form a 1-piperidinyl.

In one special preferred embodiment of the invention $R^1$ and $R^2$ together with the N atom to which it is bound form a 1-piperazinyl.

In one special preferred embodiment of the invention $R^1$ and $R^2$ together with the N atom to which it is bound form a 1-methyl-4-piperazinyl.

In one special preferred embodiment of the invention $R^1$ and $R^2$ together with the N atom to which it is bound form a 4-morpholinyl.

In one embodiment of the invention $R^{1a}$ is halogen, cyano, $C_1$-$C_6$-haloalkyl, $C_1$-$C_6$-alkoxy, $C_1$-$C_6$-haloalkoxy. In another preferred aspect of the invention $R^{1a}$ is fluorine, chlorine, cyano, methyl, methoxy, trifluoromethyl, trifluoromethoxy, difluoromethyl or difluoromethoxy. In a more preferred aspect of the invention $R^{1a}$ is halogen or $C_1$-$C_6$-alkyl; particularly fluorine, chlorine or methyl.

According to one embodiment $R^3$ is H. According to one embodiment $R^3$ is $C_1$-$C_6$-alkyl, preferably methyl, ethyl, n-propyl, i-propyl, n-butyl, i-butyl, t-butyl, in particular methyl, ethyl.

According to one embodiment $R^3$ is $C_1$-$C_6$-haloalkyl, preferably by halogen substituted methyl, ethyl, n-propyl, i-propyl, n-butyl, i-butyl, t-butyl, in particular methyl, ethyl. In a preferred embodiment of the invention, $R^3$ is H, $CH_3$ and $CF_3$. In a special embodiment of the invention, $R^3$ is $CF_3$.

According to one embodiment $R^4$ is H. According to one embodiment $R^4$ is $C_1$-$C_6$-alkyl, preferably methyl, ethyl, n-propyl, i-propyl, n-butyl, i-butyl, t-butyl, in particular methyl, ethyl.

According to one embodiment $R^4$ is $C_1$-$C_6$-haloalkyl, preferably by halogen substituted methyl, ethyl, n-propyl, i-propyl, n-butyl, i-butyl, t-butyl, in particular methyl, ethyl. In a preferred embodiment of the invention, $R^4$ is H, $CH_3$ and $CF_3$. In a special embodiment of the invention, $R^4$ is $CF_3$.

According to one embodiment $R^3$ and $R^4$ are independently of each other hydrogen, fluorine, methyl or trifluoromethyl. In a further embodiment $R^3$ and $R^4$ are independently selected from the group consisting of hydrogen and $C_1$-$C_4$-alkyl, in particular from hydrogen and $CH_3$. According to another embodiment $R^3$ is hydrogen and $R^4$ is hydrogen or $C_1$-$C_4$-alkyl, in particular hydrogen or $CH_3$.

In another aspect $R^3$ and $R^4$ are both hydrogen. In a further aspect $R^3$ is hydrogen and $R^4$ is $CH_3$. In still another aspect $R^3$ is hydrogen and $R^4$ is trifluoromethyl. In yet another aspect $R^3$ and $R^4$ are both methyl. In one embodiment $R^3$ and $R^4$ are both trifluoromethyl.

In yet another embodiment $R^3$ and $R^4$ independently of each other are H, $CH_3$ or trifluoromethyl.

In one embodiment the present invention relates to compounds (1.1) of the formula I wherein:

A is phenyl or a 5- or 6-membered aromatic heterocycle, wherein the ring member atoms of the heterocyclic ring include besides carbon atoms 1, 2, 3 or 4 heteroatoms selected from N, O and S as ring member atoms; and wherein the cyclic groups A are unsubstituted or substituted by 1, 2, 3 or 4 identical or different groups $R^A$; wherein $R^A$ is halogen, cyano, $NO_2$, OH, $NH_2$, SH, $C_1$-$C_6$-alkoxy, $C_1$-$C_6$-alkylsulfinyl, $C_1$-$C_6$-alkylsulfonyl, $C_2$-$C_6$-alkenyl, $C_2$-$C_6$-alkynyl, $C_3$-$C_8$-cycloalkyl or $C_3$-$C_8$-cycloalkoxy; and wherein any of the aliphatic or cyclic moieties are unsubstituted or substituted by 1, 2, 3 or 4 identical or different groups $R^a$; wherein $R^a$ is halogen, cyano, $NO_2$, OH, SH, $NH_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-haloalkylthio or $C_3$-$C_8$-cycloalkyl;

$R^1$ is hydrogen, $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkenyl, heteroaryl-$C_1$-$C_4$-alkyl, phenyl, naphthyl or a 3- to 10-membered saturated, partially unsaturated or aromatic mono- or bicyclic heterocycle, wherein the ring member atoms of said mono- or bicyclic heterocycle include besides carbon atoms further 1, 2, 3 or 4 heteroatoms selected from N, O and S as ring member atoms and wherein 1 or 2 carbon ring member atoms of the heterocycle may be replaced by 1 or 2 groups independently selected from C(=O) and C(=S); and wherein the heteroaryl group in heteroaryl-$C_1$-$C_4$-alkyl is a 5- or 6-membered aromatic heterocycle, wherein the ring member atoms of the heterocyclic ring include besides carbon atoms 1, 2, 3 or 4 heteroatoms selected from N, O and S as ring member atoms; and wherein any of the above-mentioned aliphatic or cyclic groups are unsubstituted or substituted by 1, 2, 3 or up to the maximum possible number of identical or different groups $R^{1a}$; wherein $R^{1a}$ is halogen, cyano, $NO_2$, OH, SH, $NH_2$, $C_1$-$C_6$-alkyl, $C_1$-$C_6$-alkoxy, $C_1$-$C_6$-haloalkoxy, $C_1$-$C_6$-haloalkylthio, $C_3$-$C_8$-cycloalkyl, $NHSO_2$—$C_1$-$C_4$-alkyl, (C=O)—$C_1$-$C_4$-alkyl, C(=O)—$C_1$-$C_4$-alkoxy, $C_1$-$C_6$-alkylsulfonyl or $C_1$-$C_6$-haloalkylsulfonyl;

$R^2$ is C(=O)—($C_1$-$C_6$-alkyl), C(=O)—($C_1$-$C_6$-alkoxy);

or $R^1$ and $R^2$ together with the nitrogen atom to which they are bound form a saturated or partially unsaturated mono- or bicyclic 3- to 7-membered heterocycle, wherein the heterocycle includes beside one nitrogen atom and one or more carbon atoms no further heteroatom or 1, 2 or 3 further heteroatoms independently selected from N, O and S as ring member atoms; and wherein one or two $CH_2$ groups of the heterocycle may be replaced by one or two groups independently selected from the group of C(=O) and C(=S); and wherein the heterocycle is unsubstituted or carries 1, 2, 3, 4 or up to the maximum possible number of identical or different groups $R^{1a}$ as defined or preferably defined herein;

$R^3$ is H, $C_1$-$C_4$-alkyl or $C_1$-$C_4$-haloalkyl;
$R^4$ is H, $C_1$-$C_4$-alkyl or $C_1$-$C_4$-haloalkyl;
or the N-oxides, or the agriculturally acceptable salts thereof.

In a further embodiment the invention relates to compounds (I.1), wherein A is (A.2). In a further embodiment the invention relates to compounds (I.1), wherein A is (A.2), and wherein A is substituted by 1 group $R^A$ as defined or preferably defined herein. In yet another embodiment the invention relates to compounds (I.1), wherein A is (A.2), and wherein A is unsubstituted. In another embodiment the invention relates to compounds (I.1), wherein A is (A.8). In a further embodiment the invention relates to compounds (I.1), wherein A is (A.8), and wherein A is substituted by 1 group $R^A$ as defined or preferably defined herein. In yet another embodiment the invention relates to compounds (I.1), wherein A is (A.8), and wherein A is unsubstituted. In another embodiment the invention relates to compounds (I.1), wherein A is (A.4). In a further embodiment the invention relates to compounds (I.1), wherein A is (A.4), and wherein A is substituted by 1 group $R^A$ as defined or preferably defined herein. In yet another embodiment the invention relates to compounds (I.1), wherein A is (A.4), and wherein A is unsubstituted.

In one embodiment the present invention relates to compounds (I.2) of the formula I wherein:

A is phenyl or a 5- or 6-membered aromatic heterocycle, wherein the ring member atoms of the heterocyclic ring include besides carbon atoms 1, 2, 3 or 4 heteroatoms selected from N, O and S as ring member atoms; and wherein the cyclic groups A are unsubstituted or substituted by 1, 2, 3 or 4 identical or different groups $R^A$; wherein $R^A$ is halogen, cyano, $NO_2$, OH, $NH_2$, SH, $C_1$-$C_6$-alkyl, $C_1$-$C_6$-alkoxy, $C_1$-$C_6$-alkylthio, $C_1$-$C_6$-alkylsulfinyl, $C_1$-$C_6$-alkylsulfonyl, $C_2$-$C_6$-alkenyl, $C_2$-$C_6$-alkynyl, $C_3$-$C_8$-cycloalkyl or $C_3$-$C_8$-cycloalkoxy; and wherein any of the aliphatic or cyclic moieties are unsubstituted or substituted by 1, 2, 3 or 4 identical or different groups $R^a$; wherein $R^a$ is halogen, cyano, $NO_2$, OH, SH, $NH_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio or $C_3$-$C_8$-cycloalkyl;

$R^1$ is hydrogen, $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkenyl, phenyl-$C_1$-$C_4$-alkyl, heteroaryl-$C_1$-$C_4$-alkyl, phenyl or a 3- to 10-membered saturated, partially unsaturated mono- or bicyclic heterocycle, wherein the ring member atoms of said mono- or bicyclic heterocycle include besides carbon atoms further 1, 2, 3 or 4 heteroatoms selected from N, O and S as ring member atoms and wherein 1 or 2 carbon ring member atoms of the heterocycle may be replaced by 1 or 2 groups independently selected from C(=O) and C(=S); and wherein the heteroaryl group in heteroaryl-$C_1$-$C_4$-alkyl is a 5- or 6-membered aromatic heterocycle, wherein the ring member atoms of the heterocyclic ring include besides carbon atoms 1, 2, 3 or 4 heteroatoms selected from N, O and S as ring member atoms; and wherein any of the above-mentioned aliphatic or cyclic groups are unsubstituted or substituted by 1, 2, 3 or up to the maximum possible number of identical or different groups $R^{1a}$; wherein $R^{1a}$ is halogen, cyano, $NO_2$, OH, SH, $NH_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $NHSO_2$—$C_1$-$C_4$-alkyl, (C=O)—$C_1$-$C_4$-alkyl, C(=O)—$C_1$-$C_4$-alkoxy or $C_1$-$C_6$-alkylsulfonyl;

$R^2$ is C(=O)—($C_1$-$C_6$-alkyl) or C(=O)—($C_1$-$C_6$-alkoxy); or $R^1$ and $R^2$ together with the nitrogen atom to which they are bound form a saturated or partially unsaturated monocyclic 5- to 7-membered heterocycle, wherein the heterocycle includes beside one nitrogen atom and one or more carbon atoms no further heteroatom or 1 or 2 further heteroatoms independently selected from N, O and S as ring member atoms; and wherein one or two $CH_2$ groups of the heterocycle are replaced by one or two groups independently selected from the group of C(=O) and C(=S); and wherein the heterocycle is unsubstituted or carries 1, 2, 3, 4 or up to the maximum possible number of identical or different groups $R^{1a}$ as defined or preferably defined herein; particularly $R^{1a}$ is halogen or $C_1$-$C_6$-alkyl;

$R^3$, $R^4$ independently of each other are hydrogen, $C_1$-$C_4$-alkyl or $C_1$-$C_4$-haloalkyl;

or the N-oxides, or the agriculturally acceptable salts thereof.

In a further embodiment the invention relates to compounds (I.2), wherein A is (A.2). In a further embodiment the invention relates to compounds (I.2), wherein A is (A.2), and wherein A is substituted by 1 group $R^4$ as defined or preferably defined herein. In yet another embodiment the invention relates to compounds (I.2), wherein A is (A.2), and wherein A is unsubstituted. In another embodiment the invention relates to compounds (I.2), wherein A is (A.8). In a further embodiment the invention relates to compounds (I.2), wherein A is (A.8), and wherein A is substituted by 1 group $R^4$ as defined or preferably defined herein. In yet another embodiment the invention relates to compounds (I.2), wherein A is (A.8), and wherein A is unsubstituted. In another embodiment the invention relates to compounds (I.2), wherein A is (A.4). In another embodiment the invention relates to compounds (I.2), wherein A is (A.4), and wherein $R^4$ is hydrogen or $CH_3$. In a further embodiment the invention relates to compounds (I.2), wherein A is (A.4), and wherein A is substituted by 1 group $R^4$ as defined or preferably defined herein. In a further embodiment the invention relates to compounds (I.2), wherein A is (A.4), and wherein A is substituted by 1 group $R^4$ as defined or preferably defined herein, and wherein $R^3$ is hydrogen and $R^4$ is hydrogen or $CH_3$. In yet another embodiment the invention relates to compounds (I.2), wherein A is (A.4), and wherein A is unsubstituted. In yet another embodiment the invention relates to compounds (I.2), wherein A is (A.4), and wherein A is unsubstituted, and wherein $R^3$ is hydrogen and wherein $R^4$ is hydrogen or $CH_3$.

In one embodiment the present invention relates to compounds (I.3) of the formula I wherein:

A is phenyl or a 5- or 6-membered aromatic heterocycle, wherein the ring member atoms of the heterocyclic ring include besides carbon atoms 1, 2, 3 or 4 heteroatoms selected from N, O and S as ring member atoms; and wherein the cyclic groups A are unsubstituted or substituted by 1, 2, 3 or 4 identical or different groups $R^A$; wherein $R^A$ is halogen, cyano, $NO_2$, OH, $NH_2$, SH, $C_1$-$C_6$-alkyl, $C_1$-$C_6$-alkoxy, $C_1$-$C_6$-alkylthio, $C_1$-$C_6$-alkylsulfinyl, $C_1$-$C_6$-alkylsulfonyl, $C_2$-$C_6$-alkenyl, $C_2$-$C_6$-alkynyl, $C_3$-$C_8$-cycloalkyl or $C_3$-$C_8$-cycloalkoxy; and wherein any of the aliphatic or cyclic moieties are unsubstituted or substituted by 1, 2, 3 or 4 identical or different groups $R^a$; wherein $R^a$ is halogen, cyano, $NO_2$, OH, SH, $NH_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio or $C_3$-$C_8$-cycloalkyl;

$R^1$ is hydrogen, $C_1$-$C_6$-alkyl, $C_2$-$C_6$-alkenyl, $C_2$-$C_6$-alkynyl or $C_3$-$C_8$-cycloalkyl;

$R^2$ is C(=O)—($C_1$-$C_6$-alkyl) or C(=O)—($C_1$-$C_6$-alkoxy);

$R^3$ is hydrogen;

$R^4$ is hydrogen, $C_1$-$C_4$-alkyl or $C_1$-$C_4$-haloalky;

or the N-oxides, or the agriculturally acceptable salts thereof.

In a further embodiment the invention relates to compounds (I.3), wherein A is (A.2). In a further embodiment the invention relates to compounds (I.3), wherein A is (A.2), and wherein A is substituted by 1 group $R^4$ as defined or preferably defined herein. In yet another embodiment the invention relates to compounds (I.3), wherein A is (A.2), and wherein A is unsubstituted. In another embodiment the invention relates to compounds (I.3), wherein A is (A.8). In a further embodiment the invention relates to compounds (I.3), wherein A is (A.8), and wherein A is substituted by 1 group $R^4$ as defined or preferably defined herein. In yet another embodiment the invention relates to compounds (I.3), wherein A is (A.8), and wherein A is unsubstituted. In another embodiment the invention relates to compounds (I.3), wherein A is (A.4). In another embodiment the invention relates to compounds (I.3), wherein A is (A.4), and wherein $R^4$ is hydrogen or $CH_3$. In a further embodiment the invention relates to compounds (I.3), wherein A is (A.4), and wherein A is substituted by 1 group $R^4$ as defined or preferably defined herein. In a further embodiment the invention relates to compounds (I.3), wherein A is (A.4), and wherein A is substituted by 1 group $R^4$ as defined or preferably defined herein, and wherein $R^4$ is hydrogen or $CH_3$. In yet another embodiment the invention relates to compounds (I.3), wherein A is (A.4), and wherein A is unsubstituted. In yet another embodiment the invention relates to compounds (I.3), wherein A is (A.4), and wherein A is unsubstituted, and wherein $R^4$ is hydrogen or $CH_3$.

In one embodiment the present invention relates to compounds (I.4) of the formula I wherein:

A is phenyl or a 5- or 6-membered aromatic heterocycle, wherein the ring member atoms of the heterocyclic ring include besides carbon atoms 1, 2, 3 or 4 heteroatoms selected from N, O and S as ring member atoms; and wherein the cyclic groups A are unsubstituted or substituted by 1, 2, 3 or 4 identical or different groups $R^A$;
wherein
$R^A$ is chlorine, fluorine or methyl;
$R^1$ is hydrogen, $C_1$-$C_6$-alkyl, $C_2$-$C_6$-alkenyl, $C_2$-$C_6$-alkynyl or $C_3$-$C_8$-cycloalkyl;
$R^2$ is C(=O)—($C_1$-$C_6$-alkyl) or C(=O)—($C_1$-$C_6$-alkoxy);
$R^3$ is hydrogen;
$R^4$ is hydrogen or $CH_3$;
or the N-oxides, or the agriculturally acceptable salts thereof.

In a further embodiment the invention relates to compounds (I.4), wherein A is (A.2). In a further embodiment the invention relates to compounds (I.4), wherein A is (A.2), and wherein A is substituted by 1 group $R^A$ as defined or preferably defined herein. In yet another embodiment the invention relates to compounds (I.4), wherein A is (A.2), and wherein A is unsubstituted.

In another embodiment the invention relates to compounds (I.4), wherein A is (A.8). In a further embodiment the invention relates to compounds (I.4), wherein A is (A.8), and wherein A is substituted by 1 group $R^A$ as defined or preferably defined herein. In yet another embodiment the invention relates to compounds (I.4), wherein A is (A.8), and wherein A is unsubstituted. In another embodiment the invention relates to compounds (I.4), wherein A is (A.4). In a further embodiment the invention relates to compounds (I.4), wherein A is (A.4), and wherein A is substituted by 1 group $R^A$ as defined or preferably defined herein. In yet another embodiment the invention relates to compounds (I.4), wherein A is (A.4), and wherein A is unsubstituted.

In one embodiment the present invention relates to compounds (I.5) of the formula I wherein:
A is phenyl or a 5- or 6-membered aromatic heterocycle, wherein the ring member atoms of the heterocyclic ring include besides carbon atoms 1, 2, 3 or 4 heteroatoms selected from N, O and S as ring member atoms; and wherein the cyclic groups A are unsubstituted or substituted by 1, 2, 3 or 4 identical or different groups $R^A$;
wherein
$R^A$ is halogen, cyano, $NO_2$, OH, $NH_2$, SH, $C_1$-$C_6$-alkyl, $C_1$-$C_6$-alkoxy, $C_1$-$C_6$-alkylthio, $C_1$-$C_6$-alkylsulfinyl, $C_1$-$C_6$-alkylsulfonyl, $C_2$-$C_6$-alkenyl, $C_2$-$C_6$-alkynyl, $C_3$-$C_8$-cycloalkyl or $C_3$-$C_8$-cycloalkoxy; and wherein any of the aliphatic or cyclic moieties are unsubstituted or substituted by 1, 2, 3 or 4 identical or different groups $R^a$; wherein
$R^a$ is halogen, cyano, $NO_2$, OH, SH, $NH_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio or $C_3$-$C_8$-cycloalkyl;
$R^1$ and $R^2$ together with the nitrogen atom to which they are bound form a saturated or partially unsaturated monocyclic 5- to 7-membered heterocycle, wherein the heterocycle includes beside one nitrogen atom and one or more carbon atoms no further heteroatom or 1 or 2 further heteroatoms independently selected from N, O and S as ring member atoms; and wherein one or two $CH_2$ groups of the heterocycle are replaced by one or two groups independently selected from the group of C(=O) and C(=S); and wherein the heterocycle is unsubstituted or carries 1, 2, 3, 4 or up to the maximum possible number of identical or different groups $R^{1a}$ as defined or preferably defined herein; particularly $R^{1a}$ is halogen or $C_1$-$C_6$-alkyl;

$R^3$, $R^4$ independently of each other are hydrogen, $C_1$-$C_4$-alkyl or $C_1$-$C_4$-haloalky; or the N-oxides, or the agriculturally acceptable salts thereof.

In a further embodiment the invention relates to compounds (I.5), wherein A is (A.2). In a further embodiment the invention relates to compounds (I.5), wherein A is (A.2), and wherein A is substituted by 1 group $R^A$ as defined or preferably defined herein. In yet another embodiment the invention relates to compounds (I.5), wherein A is (A.2), and wherein A is unsubstituted. In another embodiment the invention relates to compounds (I.5), wherein A is (A.8). In a further embodiment the invention relates to compounds (I.5), wherein A is (A.8), and wherein A is substituted by 1 group $R^A$ as defined or preferably defined herein. In yet another embodiment the invention relates to compounds (I.5), wherein A is (A.8), and wherein A is unsubstituted. In another embodiment the invention relates to compounds (I.5), wherein A is (A.4). In another embodiment the invention relates to compounds (I.5), wherein A is (A.4), and wherein $R^4$ is hydrogen or $CH_3$. In a further embodiment the invention relates to compounds (I.5), wherein A is (A.4), and wherein A is substituted by 1 group $R^A$ as defined or preferably defined herein. In a further embodiment the invention relates to compounds (I.5), wherein A is (A.4), and wherein A is substituted by 1 group $R^A$ as defined or preferably defined herein, and wherein $R^3$ is hydrogen and $R^4$ is hydrogen or $CH_3$. In yet another embodiment the invention relates to compounds (I.5), wherein A is (A.4), and wherein A is unsubstituted. In yet another embodiment the invention relates to compounds (I.5), wherein A is (A.4), and wherein A is unsubstituted, and wherein $R^3$ is hydrogen and wherein $R^4$ is hydrogen or $CH_3$.

In one embodiment the present invention relates to compounds (I.6) of the formula I wherein:
A is phenyl or a 5- or 6-membered aromatic heterocycle, wherein the ring member atoms of the heterocyclic ring include besides carbon atoms 1, 2, 3 or 4 heteroatoms selected from N, O and S as ring member atoms; and wherein the cyclic groups A are unsubstituted or substituted by 1, 2, 3 or 4 identical or different groups $R^A$;
wherein
$R^A$ is halogen, cyano, $NO_2$, OH, $NH_2$, SH, $C_1$-$C_6$-alkyl, $C_1$-$C_6$-alkoxy, $C_1$-$C_6$-alkylthio, $C_1$-$C_6$-alkylsulfinyl, $C_1$-$C_6$-alkylsulfonyl, $C_2$-$C_6$-alkenyl, $C_2$-$C_6$-alkynyl, $C_3$-$C_8$-cycloalkyl or $C_3$-$C_8$-cycloalkoxy; and wherein any of the aliphatic or cyclic moieties are unsubstituted or substituted by 1, 2, 3 or 4 identical or different groups $R^a$; wherein
$R^a$ is halogen, cyano, $NO_2$, OH, SH, $NH_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio or $C_3$-$C_8$-cycloalkyl;
$R^1$ and $R^2$ together with the nitrogen atom to which they are bound form a saturated or partially unsaturated monocyclic 5- or 6-membered heterocycle, wherein the heterocycle includes beside one nitrogen atom and one or more carbon atoms no further heteroatom or 1 further heteroatom independently selected from N, O and S as ring member atoms; and wherein one or two $CH_2$ groups of the heterocycle are replaced by one or two groups independently selected from the group of C(=O) and C(=S); and wherein the heterocycle is unsubstituted or carries 1, 2, 3, 4 or up to the maximum possible number of identical or different groups $R^{1a}$ as defined or preferably defined herein; particularly $R^{1a}$ is halogen or $C_1$-$C_6$-alkyl;
$R^3$ is hydrogen;
$R^4$ is hydrogen, $C_1$-$C_4$-alkyl or $C_1$-$C_4$-haloalkyl;

or the N-oxides, or the agriculturally acceptable salts thereof.

In a further embodiment the invention relates to compounds (I.6), wherein A is (A.2). In a further embodiment the invention relates to compounds (I.6), wherein A is (A.2), and wherein A is substituted by 1 group $R^4$ as defined or preferably defined herein. In yet another embodiment the invention relates to compounds (I.6), wherein A is (A.2), and wherein A is unsubstituted. In another embodiment the invention relates to compounds (I.6), wherein A is (A.8). In a further embodiment the invention relates to compounds (I.6), wherein A is (A.8), and wherein A is substituted by 1 group $R^4$ as defined or preferably defined herein. In yet another embodiment the invention relates to compounds (I.6), wherein A is (A.8), and wherein A is unsubstituted. In another embodiment the invention relates to compounds (I.6), wherein A is (A.4). In another embodiment the invention relates to compounds (I.6), wherein A is (A.4), and wherein $R^4$ is hydrogen or $CH_3$. In a further embodiment the invention relates to compounds (I.6), wherein A is (A.4), and wherein A is substituted by 1 group $R^4$ as defined or preferably defined herein. In a further embodiment the invention relates to compounds (I.6), wherein A is (A.4), and wherein A is substituted by 1 group $R^4$ as defined or preferably defined herein, and wherein $R^4$ is hydrogen or $CH_3$. In yet another embodiment the invention relates to compounds (I.6), wherein A is (A.4), and wherein A is unsubstituted. In yet another embodiment the invention relates to compounds (I.6), wherein A is (A.4), and wherein A is unsubstituted, and wherein $R^4$ is hydrogen or $CH_3$.

According to one embodiment, the present invention relates to compounds of the formula I.A

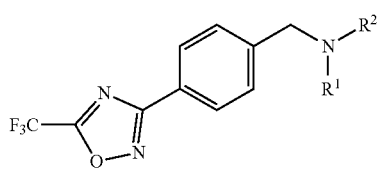

I.A or to the use of the compounds of the formula I.A for controlling phytopathogenic fungi. Here, the variables are as defined elsewhere herein for formula I, or as defined as being preferred for formula I.

According to one embodiment, the present invention relates to compounds of the formula I.B

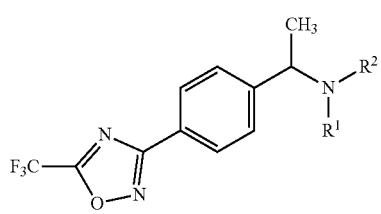

I.B or to the use of the compounds of the formula I.B for controlling phytopathogenic fungi. Here, the variables are as defined elsewhere herein for formula I, or as defined as being preferred for formula I.

According to one embodiment, the present invention relates to compounds of the formula I.C

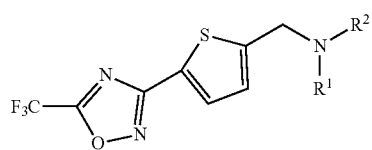

I.C or to the use of the compounds of the formula I.C for controlling phytopathogenic fungi. Here, the variables are as defined elsewhere herein for formula I, or as defined as being preferred for formula I.

According to one embodiment, the present invention relates to compounds of the formula I.D

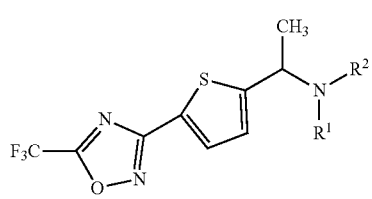

I.D or to the use of the compounds of the formula I.D for controlling phytopathogenic fungi. Here, the variables are as defined elsewhere herein for formula I, or as defined as being preferred for formula I.

According to one embodiment, the present invention relates to compounds of the formula I.E

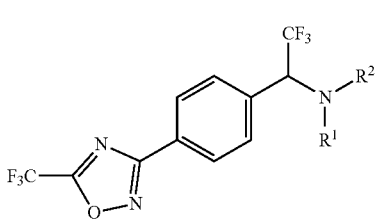

I.E or to the use of the compounds of the formula I.E for controlling phytopathogenic fungi. Here, the variables are as defined elsewhere herein for formula I, or as defined as being preferred for formula I.

According to one embodiment, the present invention relates to compounds of the formula I.F

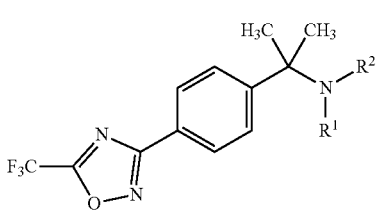

I.F or to the use of the compounds of the formula I.F for controlling phytopathogenic fungi. Here, the variables are as defined elsewhere herein for formula I, or as defined as being preferred for formula I.

According to one embodiment, the present invention relates to compounds of the formula I.G

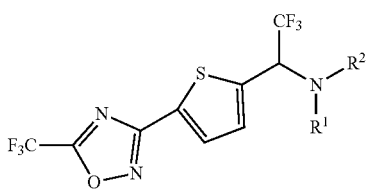

I.G or to the use of the compounds of the formula I.G for controlling phytopathogenic fungi. Here, the variables are as defined elsewhere herein for formula I, or as defined as being preferred for formula I.

According to one embodiment, the present invention relates to compounds of the formula I.H

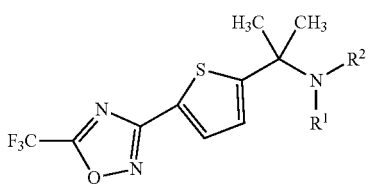

I.H or to the use of the compounds of the formula I.H for controlling phytopathogenic fungi. Here, the variables are as defined elsewhere herein for formula I, or as defined as being preferred for formula I.

According to one embodiment, the present invention relates to compounds of the formula I.I

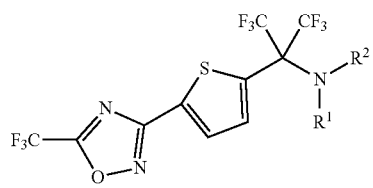

I.I or to the use of the compounds of the formula I.I for controlling phytopathogenic fungi. Here, the variables are as defined elsewhere herein for formula I, or as defined as being preferred for formula I.

According to one embodiment, the present invention relates to compounds of the formula I.J or to the use of the compounds of the formula I.J for controlling phytopathogenic fungi. Here, the variables are as defined elsewhere herein for formula I, or as defined as being preferred for formula I.

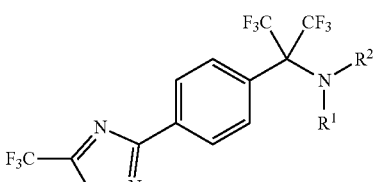

I.J

According to one embodiment, the present invention relates to compounds of the formula I.K, I.L, I.M, I.N, I.O, I.P, I.Q, I.R or I.S or to the use of the compounds of the formula I.K, I.L, I.M, I.N, I.O, I.P, I.Q, I.R or I.S for controlling phytopathogenic fungi. Here, the variables $R^3$ and $R^4$ are as defined or preferably defined herein for formula I.

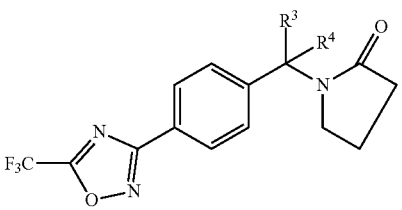

I.K

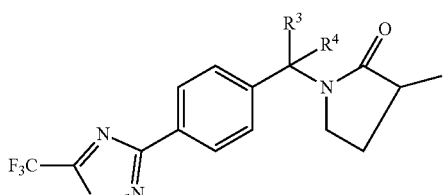

I.L

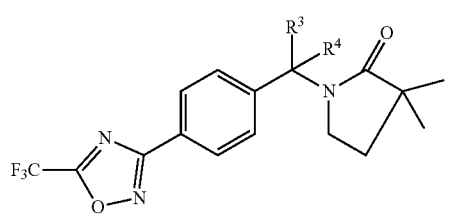

I.M

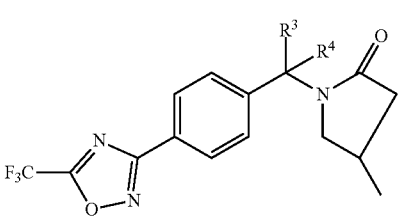

I.N

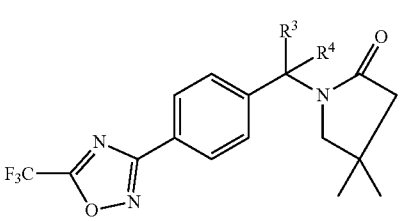

I.O

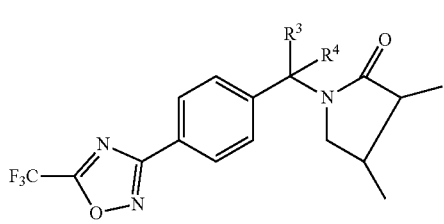

I.P

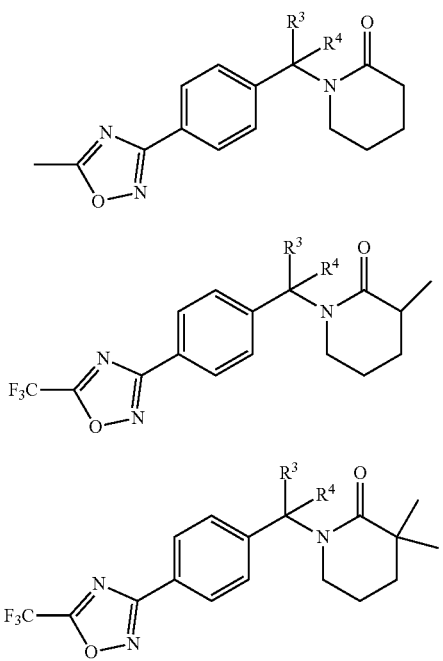

Preference is given to the compounds I used according to the invention and to the compounds according to the invention compiled in Tables 1 to 10 below. With regard to the compounds according to the invention the exception as defined above will be considered. The groups mentioned for a substituent in the tables are furthermore per se, independently of the combination in which they are mentioned, a particularly preferred aspect of the substituent in question.

Table 1

Compounds of the formula I.A, in which $R^1$ and $R^2$ for each individual compound corresponds in each case to one line of Table A (I.A.A-1 to I.A.A-973). For example, compound I.A.A-3 is therefore to be construed as a compound of formula I.A, wherein the meaning of $R^1$ and $R^2$ is as defined in line A-3 of table A ($R^1$ is hydrogen and $R^2$ is ethyl).

Table 2

Compounds of the formula I.B, in which $R^1$ and $R^2$ for each individual compound corresponds in each case to one line of Table A (I.B.A-1 to I.B.A-973).

Table 3

Compounds of the formula I.C, in which $R^1$ and $R^2$ for each individual compound corresponds in each case to one line of Table A (I.C.A-1 to I.C.A-973)

Table 4

Compounds of the formula I.D, in which $R^1$ and $R^2$ for each individual compound corresponds in each case to one line of Table A (I.D.A-1 to I.D.A-973).

Table 5

Compounds of the formula I.E, in which $R^1$ and $R^2$ for each individual compound corresponds in each case to one line of Table A (I.E.A-1 to I.E.A-973).

Table 6

Compounds of the formula I.F, in which $R^1$ and $R^2$ for each individual compound corresponds in each case to one line of Table A (I.F.A-1 to I.F.A-973).

Table 7

Compounds of the formula I.G, in which $R^1$ and $R^2$ for each individual compound corresponds in each case to one line of Table A (I.G.A-1 to I.G.A-503).

Table 8

Compounds of the formula I.H, in which $R^1$ and $R^2$ for each individual compound corresponds in each case to one line of Table A (I.H.A-1 to I.H.A-973).

Table 9

Compounds of the formula I.I, in which $R^1$ and $R^2$ for each individual compound corresponds in each case to one line of Table A (I.I.A-1 to I.I.A-973).

Table 10

Compounds of the formula I.J, in which $R^1$ and $R^2$ for each individual compound corresponds in each case to one line of Table A (I.J.A-1 to I.J.A-973).

TABLE A

| No | $R^1$ | $R^2$ |
|---|---|---|
| A-1 | H | H |
| A-2 | H | $CH_3$ |
| A-3 | H | $CH_2CH_3$ |
| A-4 | H | $CH_2CH_2CH_3$ |
| A-5 | H | $CH(CH_3)_2$ |
| A-6 | H | $CH_2CH_2CH_2CH_3$ |
| A-7 | H | $CH(CH_3)CH_2CH_3$ |
| A-8 | H | $CH_2CH(CH_3)CH_3$ |
| A-9 | H | $C(CH_3)_3$ |
| A-10 | H | $C(=O)—CH_3$ |
| A-11 | H | $C(=O)—CH_2CH_3$ |
| A-12 | H | $C(=O)—CH_2CH_2CH_3$ |
| A-13 | H | $C(=O)—CH(CH_3)_2$ |
| A-14 | H | $C(=O)—CH_2CH_2CH_2CH_3$ |
| A-15 | H | $C(=O)—CH(CH_3)CH_2CH_3$ |
| A-16 | H | $C(=O)—CH_2CH(CH_3)CH_3$ |
| A-17 | H | $C(=O)—C(CH_3)_3$ |
| A-18 | H | $C(=O)—CH_2CH_2CH_2CH_2CH_3$ |
| A-19 | H | $C(=O)—CH(CH_3)CH_2CH_2CH_3$ |
| A-20 | H | $C(=O)—CH_2CH(CH_3)CH_2CH_3$ |
| A-21 | H | $C(=O)—CH_2CH_2CH(CH_3)CH_3$ |
| A-22 | H | $C(=O)—CH(CH_2CH_3)CH_2CH_3$ |
| A-23 | H | $C(=O)—OCH_3$ |
| A-24 | H | $C(=O)—OCH_2CH_3$ |
| A-25 | H | $C(=O)—OCH_2CH_2CH_3$ |
| A-26 | H | $C(=O)—OCH(CH_3)_2$ |
| A-27 | H | $C(=O)—OCH_2CH_2CH_2CH_3$ |
| A-28 | H | $C(=O)—OCH(CH_3)CH_2CH_3$ |
| A-29 | H | $C(=O)—OCH_2CH(CH_3)CH_3$ |
| A-30 | H | $C(=O)—OC(CH_3)_3$ |
| A-31 | H | $C(=O)—OCH_2CH_2CH_2CH_2CH_3$ |
| A-32 | H | $C(=O)—OCH(CH_3)CH_2CH_2CH_3$ |
| A-33 | H | $C(=O)—OCH_2CH(CH_3)CH_2CH_3$ |
| A-34 | H | $C(=O)—OCH_2CH_2CH(CH_3)CH_3$ |
| A-35 | H | $C(=O)—OCH(CH_2CH_3)CH_2CH_3$ |
| A-36 | H | allyl |
| A-37 | H | propargyl |
| A-38 | H | cyclopropyl |
| A-39 | H | cylopentyl |
| A-40 | H | cyclohexyl |
| A-41 | H | phenyl |
| A-42 | H | 2-pyridyl |
| A-43 | H | 3-pyridyl |
| A-44 | H | 4-pyridyl |
| A-45 | H | 2-F-phenyl |
| A-46 | H | 3-F-phenyl |
| A-47 | H | 4-F-phenyl |
| A-48 | H | 2-Cl-phenyl |
| A-49 | H | 3-Cl-phenyl |
| A-50 | H | 4-Cl-phenyl |
| A-51 | H | 2-methyl-phenyl |
| A-52 | H | 3-methyl-phenyl |
| A-53 | H | 4-methyl-phenyl |
| A-54 | H | 2-ethyl-phenyl |
| A-55 | H | 3-ethyl-phenyl |
| A-56 | H | 4-ethyl-phenyl |
| A-57 | H | 2-isopropyl-phenyl |
| A-58 | H | 3-isopropyl-phenyl |
| A-59 | H | 4-isopropyl-phenyl |
| A-60 | H | 2-(2,2,2-trifluoroethyl)-phenyl |
| A-61 | H | 3-(2,2,2-trifluoroethyl)-phenyl |
| A-62 | H | 4-(2,2,2-trifluoroethyl)-phenyl |

TABLE A-continued

| No | R¹ | R² |
|---|---|---|
| A-63 | H | 2-trifluoromethyl-phenyl |
| A-64 | H | 3-trifluoromethyl-phenyl |
| A-65 | H | 4-trifluoromethyl-phenyl |
| A-66 | H | 2-methoxy-phenyl |
| A-67 | H | 3-methoxy-phenyl |
| A-68 | H | 4-methoxy-phenyl |
| A-69 | H | 2-trifluoromethoxy-phenyl |
| A-70 | H | 3-trifluoromethoxy-phenyl |
| A-71 | H | 4-trifluoromethoxy-phenyl |
| A-72 | H | 2-difluoromethoxy-phenyl |
| A-73 | H | 3-difluoromethoxy-phenyl |
| A-74 | H | 4-difluoromethoxy-phenyl |
| A-75 | H | 2-(2,2,2-trifluoroethoxy)-phenyl |
| A-76 | H | 3-(2,2,2-trifluoroethoxy)-phenyl |
| A-77 | H | 4-(2,2,2-trifluoroethoxy)-phenyl |
| A-78 | H | 2-cyano-phenyl |
| A-79 | H | 3-cyano-phenyl |
| A-80 | H | 4-cyano-phenyl |
| A-81 | H | 2,3-difluoro-phenyl |
| A-82 | H | 2,4-difluoro-phenyl |
| A-83 | H | 2,5-difluoro-phenyl |
| A-84 | H | 2,6-difluoro-phenyl |
| A-85 | H | 2,3-dichloro-phenyl |
| A-86 | H | 2,4-dichloro-phenyl |
| A-87 | H | 2,5-dichloro-phenyl |
| A-88 | H | 2,6-dichloro-phenyl |
| A-89 | H | 2-F-3-Cl-phenyl |
| A-90 | H | 2-F-4-Cl-phenyl |
| A-91 | H | 2-F-5-Cl-phenyl |
| A-92 | H | 2-F-6-Cl-phenyl |
| A-93 | H | 3-F-4-Cl-phenyl |
| A-94 | H | 3-F-5-Cl-phenyl |
| A-95 | H | 2-Cl-3-F-phenyl |
| A-96 | H | 2-Cl-4-F-phenyl |
| A-97 | H | 2-Cl-5-F-phenyl |
| A-98 | H | 3-Cl-4-F-phenyl |
| A-99 | H | 2-F-3-methyl-phenyl |
| A-100 | H | 2-F-4-methyl-phenyl |
| A-101 | H | 2-F-5-methyl-phenyl |
| A-102 | H | 2-F-6-methyl-phenyl |
| A-103 | H | 3-F-4-methyl-phenyl |
| A-104 | H | 3-F-5-methyl-phenyl |
| A-105 | H | 2-methyl-3-F-phenyl |
| A-106 | H | 2-methyl-4-F-phenyl |
| A-107 | H | 2-methyl-5-F-phenyl |
| A-108 | H | 3-methyl-4-F-phenyl |
| A-109 | H | 2-F-3-CF₃-phenyl |
| A-110 | H | 2-F-4-CF₃-phenyl |
| A-111 | H | 2-F-5-CF₃-phenyl |
| A-112 | H | 2-F-6-CF₃-phenyl |
| A-113 | H | 3-F-4-CF₃-phenyl |
| A-114 | H | 3-F-5-CF₃-phenyl |
| A-115 | H | 2-CF₃-3-F-phenyl |
| A-116 | H | 2-CF₃-4-F-phenyl |
| A-117 | H | 2-CF₃-5-F-phenyl |
| A-118 | H | 3-CF₃-4-F-phenyl |
| A-119 | H | 2-F-3-OMe-phenyl |
| A-120 | H | 2-F-4-OMe-phenyl |
| A-121 | H | 2-F-5-OMe-phenyl |
| A-122 | H | 2-F-6-OMe-phenyl |
| A-123 | H | 3-F-4-OMe-phenyl |
| A-124 | H | 3-F-5-OMe-phenyl |
| A-125 | H | 2-OMe-3-F-phenyl |
| A-126 | H | 2-OMe-4-F-phenyl |
| A-127 | H | 2-OMe-5-F-phenyl |
| A-128 | H | 3-OMe-4-F-phenyl |
| A-129 | H | 2-F-3-OCHF₂-phenyl |
| A-130 | H | 2-F-4-OCHF₂-phenyl |
| A-131 | H | 2-F-5-OCHF₂-phenyl |
| A-132 | H | 2-F-6-OCHF₂-phenyl |
| A-133 | H | 3-F-4-OCHF₂-phenyl |
| A-134 | H | 3-F-5-OCHF₂-phenyl |
| A-135 | H | 2-OCHF₂-3-F-phenyl |
| A-136 | H | 2-OCHF₂-4-F-phenyl |
| A-137 | H | 2-OCHF₂-5-F-phenyl |
| A-138 | H | 3-OCHF₂-4-F-phenyl |
| A-139 | H | 2-F-3-CN-phenyl |
| A-140 | H | 2-F-4-CN-phenyl |
| A-141 | H | 2-F-5-CN-phenyl |
| A-142 | H | 2-F-6-CN-phenyl |
| A-143 | H | 3-F-4-CN-phenyl |
| A-144 | H | 3-F-5-CN-phenyl |
| A-145 | H | 2-CN-3-F-phenyl |
| A-146 | H | 2-CN-4-F-phenyl |
| A-147 | H | 2-CN-5-F-phenyl |
| A-148 | H | 3-CN-4-F-phenyl |
| A-149 | H | 2-Cl-3-methyl-phenyl |
| A-150 | H | 2-Cl-4-methyl-phenyl |
| A-151 | H | 2-Cl-5-methyl-phenyl |
| A-152 | H | 2-Cl-6-methyl-phenyl |
| A-153 | H | 3-Cl-4-methyl-phenyl |
| A-154 | H | 3-Cl-5-methyl-phenyl |
| A-155 | H | 2-methyl-3-Cl-phenyl |
| A-156 | H | 2-methyl-4-Cl-phenyl |
| A-157 | H | 2-methyl-5-Cl-phenyl |
| A-158 | H | 3-methyl-4-Cl-phenyl |
| A-159 | H | 2-Cl-3-CF₃-phenyl |
| A-160 | H | 2-Cl-4-CF₃-phenyl |
| A-161 | H | 2-Cl-5-CF₃-phenyl |
| A-162 | H | 2-Cl-6-CF₃-phenyl |
| A-163 | H | 3-Cl-4-CF₃-phenyl |
| A-164 | H | 3-Cl-5-CF₃-phenyl |
| A-165 | H | 2-CF₃-3-Cl-phenyl |
| A-166 | H | 2-CF₃-4-Cl-phenyl |
| A-167 | H | 2-CF₃-5-Cl-phenyl |
| A-168 | H | 3-CF₃-4-Cl-phenyl |
| A-169 | H | 2-Cl-3-OMe-phenyl |
| A-170 | H | 2-Cl-4-OMe-phenyl |
| A-171 | H | 2-Cl-5-OMe-phenyl |
| A-172 | H | 2-Cl-6-OMe-phenyl |
| A-173 | H | 3-Cl-4-OMe-phenyl |
| A-174 | H | 3-Cl-5-OMe-phenyl |
| A-175 | H | 2-OMe-3-Cl-phenyl |
| A-176 | H | 2-OMe-4-Cl-phenyl |
| A-177 | H | 2-OMe-5-Cl-phenyl |
| A-178 | H | 3-OMe-4-Cl-phenyl |
| A-179 | H | 2-Cl-3-OCHF₂-phenyl |
| A-180 | H | 2-Cl-4-OCHF₂-phenyl |
| A-181 | H | 2-Cl-5-OCHF₂-phenyl |
| A-182 | H | 2-Cl-6-OCHF₂-phenyl |
| A-183 | H | 3-Cl-4-OCHF₂-phenyl |
| A-184 | H | 3-Cl-5-OCHF₂-phenyl |
| A-185 | H | 2-OCHF₂-3-Cl-phenyl |
| A-186 | H | 2-OCHF₂-4-Cl-phenyl |
| A-187 | H | 2-OCHF₂-5-Cl-phenyl |
| A-188 | H | 3-OCHF₂-4-Cl-phenyl |
| A-189 | H | 2-Cl-3-CN-phenyl |
| A-190 | H | 2-Cl-4-CN-phenyl |
| A-191 | H | 2-Cl-5-CN-phenyl |
| A-192 | H | 2-Cl-6-CN-phenyl |
| A-193 | H | 3-Cl-4-CN-phenyl |
| A-194 | H | 3-Cl-5-CN-phenyl |
| A-195 | H | 2-CN-3-Cl-phenyl |
| A-196 | H | 2-CN-4-Cl-phenyl |
| A-197 | H | 2-CN-5-Cl-phenyl |
| A-198 | H | 3-CN-4-Cl-phenyl |
| A-199 | H | CH₂-cyclopropyl |
| A-200 | H | CH₂-cyclopentyl |
| A-201 | H | CH₂-cyclohexyl |
| A-202 | H | CH₂-(4-quinolinyl) |
| A-203 | H | CH₂-(2-pyridyl) |
| A-204 | H | CH₂-(3-pyridyl) |
| A-205 | H | CH₂-(4-pyridyl) |
| A-206 | H | CH₂-(2-thienyl) |
| A-207 | H | CH₂-(3-thienyl) |
| A-208 | H | CH₂-(N-methyl-3-pyrazolyl) |
| A-209 | H | CH₂-(N-methyl-4-pyrazolyl) |
| A-210 | H | CH₂-(1-pyrazolyl) |
| A-211 | H | CH₂-(2-oxazolyl) |
| A-212 | H | CH₂-(4-oxazolyl) |
| A-213 | H | CH₂-(5-oxazolyl) |
| A-214 | H | CH₂-(2-(1,3,4-oxadiazolyl)) |
| A-215 | H | CH₂-(2-furyl) |
| A-216 | H | CH₂-(3-furyl) |
| A-217 | H | 3-hydroxypropyl |
| A-218 | H | CH₂-(N-methyl-3-pyrrolidinyl) |

TABLE A-continued

| No | R¹ | R² |
|---|---|---|
| A-219 | H | 3-dimethylaminopropyl |
| A-220 | H | 2-dimethylaminoethyl |
| A-221 | H | 3-pyrrolidinyl |
| A-222 | H | benzyl |
| A-223 | H | (2-F-phenyl)methyl |
| A-224 | H | (3-F-phenyl)methyl |
| A-225 | H | (4-F-phenyl)methyl |
| A-226 | H | (2-Cl-phenyl)methyl |
| A-227 | H | (3-Cl-phenyl)methyl |
| A-228 | H | (4-Cl-phenyl)methyl |
| A-229 | H | (2-methyl-phenyl)methyl |
| A-230 | H | (3-methyl-phenyl)methyl |
| A-231 | H | (4-methyl-phenyl)methyl |
| A-232 | H | (2-methoxy-phenyl)methyl |
| A-233 | H | (3-methoxy-phenyl)methyl |
| A-234 | H | (4-methoxy-phenyl)methyl |
| A-235 | H | (2-cyano-phenyl)methyl |
| A-236 | H | (3-cyano-phenyl)methyl |
| A-237 | H | (4-cyano-phenyl)methyl |
| A-238 | H | (2,3-difluoro-phenyl)methyl |
| A-239 | H | (2,4-difluoro-phenyl)methyl |
| A-240 | H | (2,5-difluoro-phenyl)methyl |
| A-241 | H | (2,6-difluoro-phenyl)methyl |
| A-242 | H | (2,3-dichloro-phenyl)methyl |
| A-243 | H | (2,4-dichloro-phenyl)methyl |
| A-244 | H | (2,5-dichloro-phenyl)methyl |
| A-245 | H | (2,6-dichloro-phenyl)methyl |
| A-246 | R¹ and R² together with the nitrogen to which they are bound form a aziridinyl | |
| A-247 | R¹ and R² together with the nitrogen to which they are bound form a azetidinyl | |
| A-248 | R¹ and R² together with the nitrogen to which they are bound form a 1-pyrrolidinyl | |
| A-249 | R¹ and R² together with the nitrogen to which they are bound form a 1-piperidinyl | |
| A-250 | R¹ and R² together with the nitrogen to which they are bound form a 1-piperazinyl | |
| A-251 | R¹ and R² together with the nitrogen to which they are bound form a 1-methyl-4-piperazinyl | |
| A-252 | R¹ and R² together with the nitrogen to which they are bound form a 4-morpholinyl | |
| A-253 | $CH_3$ | $CH_3$ |
| A-254 | $CH_3$ | $CH_2CH_3$ |
| A-255 | $CH_3$ | $CH_2CH_2CH_3$ |
| A-256 | $CH_3$ | $CH(CH_3)_2$ |
| A-257 | $CH_3$ | $CH_2CH_2CH_2CH_3$ |
| A-258 | $CH_3$ | $CH(CH_3)CH_2CH_3$ |
| A-259 | $CH_3$ | $CH_2CH(CH_3)CH_3$ |
| A-260 | $CH_3$ | $C(CH_3)_3$ |
| A-261 | $CH_3$ | $C(=O)-CH_3$ |
| A-262 | $CH_3$ | $C(=O)-CH_2CH_3$ |
| A-263 | $CH_3$ | $C(=O)-CH_2CH_2CH_3$ |
| A-264 | $CH_3$ | $C(=O)-CH(CH_3)_2$ |
| A-265 | $CH_3$ | $C(=O)-CH_2CH_2CH_2CH_3$ |
| A-266 | $CH_3$ | $C(=O)-CH(CH_3)CH_2CH_3$ |
| A-267 | $CH_3$ | $C(=O)-CH_2CH(CH_3)CH_3$ |
| A-268 | $CH_3$ | $C(=O)-C(CH_3)_3$ |
| A-269 | $CH_3$ | $C(=O)-CH_2CH_2CH_2CH_2CH_3$ |
| A-270 | $CH_3$ | $C(=O)-CH(CH_3)CH_2CH_2CH_3$ |
| A-271 | $CH_3$ | $C(=O)-CH_2CH(CH_3)CH_2CH_3$ |
| A-272 | $CH_3$ | $C(=O)-CH_2CH_2CH(CH_3)CH_3$ |
| A-273 | $CH_3$ | $C(=O)-CH(CH_2CH_3)CH_2CH_3$ |
| A-274 | $CH_3$ | $C(=O)-OCH_3$ |
| A-275 | $CH_3$ | $C(=O)-OCH_2CH_3$ |
| A-276 | $CH_3$ | $C(=O)-OCH_2CH_2CH_3$ |
| A-277 | $CH_3$ | $C(=O)-OCH(CH_3)_2$ |
| A-278 | $CH_3$ | $C(=O)-OCH_2CH_2CH_2CH_3$ |
| A-279 | $CH_3$ | $C(=O)-OCH(CH_3)CH_2CH_3$ |
| A-280 | $CH_3$ | $C(=O)-OCH_2CH(CH_3)CH_3$ |
| A-281 | $CH_3$ | $C(=O)-OC(CH_3)_3$ |
| A-282 | $CH_3$ | $C(=O)-OCH_2CH_2CH_2CH_2CH_3$ |
| A-283 | $CH_3$ | $C(=O)-OCH(CH_3)CH_2CH_2CH_3$ |
| A-284 | $CH_3$ | $C(=O)-OCH_2CH(CH_3)CH_2CH_3$ |
| A-285 | $CH_3$ | $C(=O)-OCH_2CH_2CH(CH_3)CH_3$ |
| A-286 | $CH_3$ | $C(=O)-OCH(CH_2CH_3)CH_2CH_3$ |
| A-287 | $CH_3$ | allyl |
| A-288 | $CH_3$ | propargyl |
| A-289 | $CH_3$ | cyclopropyl |
| A-290 | $CH_3$ | cylopentyl |
| A-291 | $CH_3$ | cyclohexyl |
| A-292 | $CH_3$ | phenyl |
| A-293 | $CH_3$ | 2-pyridyl |
| A-294 | $CH_3$ | 3-pyridyl |
| A-295 | $CH_3$ | 4-pyridyl |
| A-296 | $CH_3$ | 2-F-phenyl |
| A-297 | $CH_3$ | 3-F-phenyl |
| A-298 | $CH_3$ | 4-F-phenyl |
| A-299 | $CH_3$ | 2-Cl-phenyl |
| A-300 | $CH_3$ | 3-Cl-phenyl |
| A-301 | $CH_3$ | 4-Cl-phenyl |
| A-302 | $CH_3$ | 2-methyl-phenyl |
| A-303 | $CH_3$ | 3-methyl-phenyl |
| A-304 | $CH_3$ | 4-methyl-phenyl |
| A-305 | $CH_3$ | 2-ethyl-phenyl |
| A-306 | $CH_3$ | 3-ethyl-phenyl |
| A-307 | $CH_3$ | 4-ethyl-phenyl |
| A-308 | $CH_3$ | 2-isopropyl-phenyl |
| A-309 | $CH_3$ | 3-isopropyl-phenyl |
| A-310 | $CH_3$ | 4-isopropyl-phenyl |
| A-311 | $CH_3$ | 2-(2,2,2-trifluoroethyl)-phenyl |
| A-312 | $CH_3$ | 3-(2,2,2-trifluoroethyl)-phenyl |
| A-313 | $CH_3$ | 4-(2,2,2-trifluoroethyl)-phenyl |
| A-314 | $CH_3$ | 2-trifluoromethyl-phenyl |
| A-315 | $CH_3$ | 3-trifluoromethyl-phenyl |
| A-316 | $CH_3$ | 4-trifluoromethyl-phenyl |
| A-317 | $CH_3$ | 2-methoxy-phenyl |
| A-318 | $CH_3$ | 3-methoxy-phenyl |
| A-319 | $CH_3$ | 4-methoxy-phenyl |
| A-320 | $CH_3$ | 2-trifluoromethoxy-phenyl |
| A-321 | $CH_3$ | 3-trifluoromethoxy-phenyl |
| A-322 | $CH_3$ | 4-trifluoromethoxy-phenyl |
| A-323 | $CH_3$ | 2-difluoromethoxy-phenyl |
| A-324 | $CH_3$ | 3-difluoromethoxy-phenyl |
| A-325 | $CH_3$ | 4-difluoromethoxy-phenyl |
| A-326 | $CH_3$ | 2-(2,2,2-trifluoroethoxy)-phenyl |
| A-327 | $CH_3$ | 3-(2,2,2-trifluoroethoxy)-phenyl |
| A-328 | $CH_3$ | 4-(2,2,2-trifluoroethoxy)-phenyl |
| A-329 | $CH_3$ | 2-cyano-phenyl |
| A-330 | $CH_3$ | 3-cyano-phenyl |
| A-331 | $CH_3$ | 4-cyano-phenyl |
| A-332 | $CH_3$ | 2,3-difluoro-phenyl |
| A-333 | $CH_3$ | 2,4-difluoro-phenyl |
| A-334 | $CH_3$ | 2,5-difluoro-phenyl |
| A-335 | $CH_3$ | 2,6-difluoro-phenyl |
| A-336 | $CH_3$ | 2,3-dichloro-phenyl |
| A-337 | $CH_3$ | 2,4-dichloro-phenyl |
| A-338 | $CH_3$ | 2,5-dichloro-phenyl |
| A-339 | $CH_3$ | 2,6-dichloro-phenyl |
| A-340 | $CH_3$ | 2-F-3-Cl-phenyl |
| A-341 | $CH_3$ | 2-F-4-Cl-phenyl |
| A-342 | $CH_3$ | 2-F-5-Cl-phenyl |
| A-343 | $CH_3$ | 2-F-6-Cl-phenyl |
| A-344 | $CH_3$ | 3-F-4-Cl-phenyl |
| A-345 | $CH_3$ | 3-F-5-Cl-phenyl |
| A-346 | $CH_3$ | 2-Cl-3-F-phenyl |
| A-347 | $CH_3$ | 2-Cl-4-F-phenyl |
| A-348 | $CH_3$ | 2-Cl-5-F-phenyl |
| A-349 | $CH_3$ | 3-Cl-4-F-phenyl |
| A-350 | $CH_3$ | 2-F-3-methyl-phenyl |
| A-351 | $CH_3$ | 2-F-4-methyl-phenyl |
| A-352 | $CH_3$ | 2-F-5-methyl-phenyl |
| A-353 | $CH_3$ | 2-F-6-methyl-phenyl |
| A-354 | $CH_3$ | 3-F-4-methyl-phenyl |
| A-355 | $CH_3$ | 3-F-5-methyl-phenyl |
| A-356 | $CH_3$ | 2-methyl-3-F-phenyl |
| A-357 | $CH_3$ | 2-methyl-4-F-phenyl |
| A-358 | $CH_3$ | 2-methyl-5-F-phenyl |
| A-359 | $CH_3$ | 3-methyl-4-F-phenyl |
| A-360 | $CH_3$ | 2-F-3-$CF_3$-phenyl |
| A-361 | $CH_3$ | 2-F-4-$CF_3$-phenyl |
| A-362 | $CH_3$ | 2-F-5-$CF_3$-phenyl |
| A-363 | $CH_3$ | 2-F-6-$CF_3$-phenyl |
| A-364 | $CH_3$ | 3-F-4-$CF_3$-phenyl |
| A-365 | $CH_3$ | 3-F-5-$CF_3$-phenyl |
| A-366 | $CH_3$ | 2-$CF_3$-3-F-phenyl |
| A-367 | $CH_3$ | 2-$CF_3$-4-F-phenyl |

TABLE A-continued

| No | R¹ | R² |
|---|---|---|
| A-368 | CH₃ | 2-CF₃-5-F-phenyl |
| A-369 | CH₃ | 3-CF₃-4-F-phenyl |
| A-370 | CH₃ | 2-F-3-OMe-phenyl |
| A-371 | CH₃ | 2-F-4-OMe-phenyl |
| A-372 | CH₃ | 2-F-5-OMe-phenyl |
| A-373 | CH₃ | 2-F-6-OMe-phenyl |
| A-374 | CH₃ | 3-F-4-OMe-phenyl |
| A-375 | CH₃ | 3-F-5-OMe-phenyl |
| A-376 | CH₃ | 2-OMe-3-F-phenyl |
| A-377 | CH₃ | 2-OMe-4-F-phenyl |
| A-378 | CH₃ | 2-OMe-5-F-phenyl |
| A-379 | CH₃ | 3-OMe-4-F-phenyl |
| A-380 | CH₃ | 2-F-3-OCHF₂-phenyl |
| A-381 | CH₃ | 2-F-4-OCHF₂-phenyl |
| A-382 | CH₃ | 2-F-5-OCHF₂-phenyl |
| A-383 | CH₃ | 2-F-6-OCHF₂-phenyl |
| A-384 | CH₃ | 3-F-4-OCHF₂-phenyl |
| A-385 | CH₃ | 3-F-5-OCHF₂-phenyl |
| A-386 | CH₃ | 2-OCHF₂-3-F-phenyl |
| A-387 | CH₃ | 2-OCHF₂-4-F-phenyl |
| A-388 | CH₃ | 2-OCHF₂-5-F-phenyl |
| A-389 | CH₃ | 3-OCHF₂-4-F-phenyl |
| A-390 | CH₃ | 2-F-3-CN-phenyl |
| A-391 | CH₃ | 2-F-4-CN-phenyl |
| A-392 | CH₃ | 2-F-5-CN-phenyl |
| A-393 | CH₃ | 2-F-6-CN-phenyl |
| A-394 | CH₃ | 3-F-4-CN-phenyl |
| A-395 | CH₃ | 3-F-5-CN-phenyl |
| A-396 | CH₃ | 2-CN-3-F-phenyl |
| A-397 | CH₃ | 2-CN-4-F-phenyl |
| A-398 | CH₃ | 2-CN-5-F-phenyl |
| A-399 | CH₃ | 3-CN-4-F-phenyl |
| A-400 | CH₃ | 2-Cl-3-methyl-phenyl |
| A-401 | CH₃ | 2-Cl-4-methyl-phenyl |
| A-402 | CH₃ | 2-Cl-5-methyl-phenyl |
| A-403 | CH₃ | 2-Cl-6-methyl-phenyl |
| A-404 | CH₃ | 3-Cl-4-methyl-phenyl |
| A-405 | CH₃ | 3-Cl-5-methyl-phenyl |
| A-406 | CH₃ | 2-methyl-3-Cl-phenyl |
| A-407 | CH₃ | 2-methyl-4-Cl-phenyl |
| A-408 | CH₃ | 2-methyl-5-Cl-phenyl |
| A-409 | CH₃ | 3-methyl-4-Cl-phenyl |
| A-410 | CH₃ | 2-Cl-3-CF₃-phenyl |
| A-411 | CH₃ | 2-Cl-4-CF₃-phenyl |
| A-412 | CH₃ | 2-Cl-5-CF₃-phenyl |
| A-413 | CH₃ | 2-Cl-6-CF₃-phenyl |
| A-414 | CH₃ | 3-Cl-4-CF₃-phenyl |
| A-415 | CH₃ | 3-Cl-5-CF₃-phenyl |
| A-416 | CH₃ | 2-CF₃-3-Cl-phenyl |
| A-417 | CH₃ | 2-CF₃-4-Cl-phenyl |
| A-418 | CH₃ | 2-CF₃-5-Cl-phenyl |
| A-419 | CH₃ | 3-CF₃-4-Cl-phenyl |
| A-420 | CH₃ | 2-Cl-3-OMe-phenyl |
| A-421 | CH₃ | 2-Cl-4-OMe-phenyl |
| A-422 | CH₃ | 2-Cl-5-OMe-phenyl |
| A-423 | CH₃ | 2-Cl-6-OMe-phenyl |
| A-424 | CH₃ | 3-Cl-4-OMe-phenyl |
| A-425 | CH₃ | 3-Cl-5-OMe-phenyl |
| A-426 | CH₃ | 2-OMe-3-Cl-phenyl |
| A-427 | CH₃ | 2-OMe-4-Cl-phenyl |
| A-428 | CH₃ | 2-OMe-5-Cl-phenyl |
| A-429 | CH₃ | 3-OMe-4-Cl-phenyl |
| A-430 | CH₃ | 2-Cl-3-OCHF₂-phenyl |
| A-431 | CH₃ | 2-Cl-4-OCHF₂-phenyl |
| A-432 | CH₃ | 2-Cl-5-OCHF₂-phenyl |
| A-433 | CH₃ | 2-Cl-6-OCHF₂-phenyl |
| A-434 | CH₃ | 3-Cl-4-OCHF₂-phenyl |
| A-435 | CH₃ | 3-Cl-5-OCHF₂-phenyl |
| A-436 | CH₃ | 2-OCHF₂-3-Cl-phenyl |
| A-437 | CH₃ | 2-OCHF₂-4-Cl-phenyl |
| A-438 | CH₃ | 2-OCHF₂-5-Cl-phenyl |
| A-439 | CH₃ | 3-OCHF₂-4-Cl-phenyl |
| A-440 | CH₃ | 2-Cl-3-CN-phenyl |
| A-441 | CH₃ | 2-Cl-4-CN-phenyl |
| A-442 | CH₃ | 2-Cl-5-CN-phenyl |
| A-443 | CH₃ | 2-Cl-6-CN-phenyl |
| A-444 | CH₃ | 3-Cl-4-CN-phenyl |
| A-445 | CH₃ | 3-Cl-5-CN-phenyl |
| A-446 | CH₃ | 2-CN-3-Cl-phenyl |
| A-447 | CH₃ | 2-CN-4-Cl-phenyl |
| A-448 | CH₃ | 2-CN-5-Cl-phenyl |
| A-449 | CH₃ | 3-CN-4-Cl-phenyl |
| A-450 | CH₃ | CH₂-cyclopropyl |
| A-451 | CH₃ | CH₂-cyclopentyl |
| A-452 | CH₃ | CH₂-cyclohexyl |
| A-453 | CH₃ | CH₂-(4-quinolinyl) |
| A-454 | CH₃ | CH₂-(2-pyridyl) |
| A-455 | CH₃ | CH₂-(3-pyridyl) |
| A-456 | CH₃ | CH₂-(4-pyridyl) |
| A-457 | CH₃ | CH₂-(2-thienyl) |
| A-458 | CH₃ | CH₂-(3-thienyl) |
| A-459 | CH₃ | CH₂-(N-methyl-3-pyrazolyl) |
| A-460 | CH₃ | CH₂-(N-methyl-4-pyrazolyl) |
| A-461 | CH₃ | CH₂-(1-pyrazolyl) |
| A-462 | CH₃ | CH₂-(2-oxazolyl) |
| A-463 | CH₃ | CH₂-(4-oxazolyl) |
| A-464 | CH₃ | CH₂-(5-oxazolyl) |
| A-465 | CH₃ | CH₂-(2-(1,3,4-oxadiazolyl)) |
| A-466 | CH₃ | CH₂-(2-furyl) |
| A-467 | CH₃ | CH₂-(3-furyl) |
| A-468 | CH₃ | 3-hydroxypropyl |
| A-469 | CH₃ | CH₂-(N-methyl-3-pyrrolidinyl) |
| A-470 | CH₃ | 3-dimethylaminopropyl |
| A-471 | CH₃ | 2-dimethylaminoethyl |
| A-472 | CH₃ | 3-pyrrolidinyl |
| A-473 | CH₃ | benzyl |
| A-474 | CH₃ | (2-F-phenyl)methyl |
| A-475 | CH₃ | (3-F-phenyl)methyl |
| A-476 | CH₃ | (4-F-phenyl)methyl |
| A-477 | CH₃ | (2-Cl-phenyl)methyl |
| A-478 | CH₃ | (3-Cl-phenyl)methyl |
| A-479 | CH₃ | (4-Cl-phenyl)methyl |
| A-480 | CH₃ | (2-methyl-phenyl)methyl |
| A-481 | CH₃ | (3-methyl-phenyl)methyl |
| A-482 | CH₃ | (4-methyl-phenyl)methyl |
| A-483 | CH₃ | (2-methoxy-phenyl)methyl |
| A-484 | CH₃ | (3-methoxy-phenyl)methyl |
| A-485 | CH₃ | (4-methoxy-phenyl)methyl |
| A-486 | CH₃ | (2-cyano-phenyl)methyl |
| A-487 | CH₃ | (3-cyano-phenyl)methyl |
| A-488 | CH₃ | (4-cyano-phenyl)methyl |
| A-489 | CH₃ | (2,3-difluoro-phenyl)methyl |
| A-490 | CH₃ | (2,4-difluoro-phenyl)methyl |
| A-491 | CH₃ | (2,5-difluoro-phenyl)methyl |
| A-492 | CH₃ | (2,6-difluoro-phenyl)methyl |
| A-493 | CH₃ | (2,3-dichloro-phenyl)methyl |
| A-494 | CH₃ | (2,4-dichloro-phenyl)methyl |
| A-495 | CH₃ | (2,5-dichloro-phenyl)methyl |
| A-496 | CH₃ | (2,6-dichloro-phenyl)methyl |
| A-497 | ethyl | H |
| A-498 | ethyl | CH₃ |
| A-499 | ethyl | CH₂CH₃ |
| A-500 | ethyl | CH₂CH₂CH₃ |
| A-501 | ethyl | CH(CH₃)₂ |
| A-502 | ethyl | CH₂CH₂CH₂CH₃ |
| A-503 | ethyl | CH(CH₃)CH₂CH₃ |
| A-504 | ethyl | CH₂CH(CH₃)CH₃ |
| A-505 | ethyl | C(CH₃)₃ |
| A-506 | ethyl | C(=O)—CH₃ |
| A-507 | ethyl | C(=O)—CH₂CH₃ |
| A-508 | ethyl | C(=O)—CH₂CH₂CH₃ |
| A-509 | ethyl | C(=O)—CH(CH₃)₂ |
| A-510 | ethyl | C(=O)—CH₂CH₂CH₂CH₃ |
| A-511 | ethyl | C(=O)—CH(CH₃)CH₂CH₃ |
| A-512 | ethyl | C(=O)—CH₂CH(CH₃)CH₃ |
| A-513 | ethyl | C(=O)—C(CH₃)₃ |
| A-514 | ethyl | C(=O)—CH₂CH₂CH₂CH₂CH₃ |
| A-515 | ethyl | C(=O)—CH(CH₃)CH₂CH₂CH₃ |
| A-516 | ethyl | C(=O)—CH₂CH(CH₃)CH₂CH₃ |
| A-517 | ethyl | C(=O)—CH₂CH₂CH(CH₃)CH₃ |
| A-518 | ethyl | C(=O)—CH(CH₂CH₃)CH₂CH₃ |
| A-519 | ethyl | C(=O)—OCH₃ |
| A-520 | ethyl | C(=O)—OCH₂CH₃ |
| A-521 | ethyl | C(=O)—OCH₂CH₂CH₃ |
| A-522 | ethyl | C(=O)—OCH(CH₃)₂ |
| A-523 | ethyl | C(=O)—OCH₂CH₂CH₂CH₃ |

TABLE A-continued

| No | R¹ | R² |
|---|---|---|
| A-524 | ethyl | C(=O)—OCH(CH₃)CH₂CH₃ |
| A-525 | ethyl | C(=O)—OCH₂CH(CH₃)CH₃ |
| A-526 | ethyl | C(=O)—OC(CH₃)₃ |
| A-527 | ethyl | C(=O)—OCH₂CH₂CH₂CH₂CH₃ |
| A-528 | ethyl | C(=O)—OCH(CH₃)CH₂CH₂CH₃ |
| A-529 | ethyl | C(=O)—OCH₂CH(CH₃)CH₂CH₃ |
| A-530 | ethyl | C(=O)—OCH₂CH₂CH(CH₃)CH₃ |
| A-531 | ethyl | C(=O)—OCH(CH₂CH₃)CH₂CH₃ |
| A-532 | ethyl | allyl |
| A-533 | ethyl | propargyl |
| A-534 | ethyl | cyclopropyl |
| A-535 | ethyl | cylopentyl |
| A-536 | ethyl | cyclohexyl |
| A-537 | ethyl | phenyl |
| A-538 | ethyl | 2-pyridyl |
| A-539 | ethyl | 3-pyridyl |
| A-540 | ethyl | 4-pyridyl |
| A-541 | ethyl | 2-F-phenyl |
| A-542 | ethyl | 3-F-phenyl |
| A-543 | ethyl | 4-F-phenyl |
| A-544 | ethyl | 2-Cl-phenyl |
| A-545 | ethyl | 3-Cl-phenyl |
| A-546 | ethyl | 4-Cl-phenyl |
| A-547 | ethyl | 2-methyl-phenyl |
| A-548 | ethyl | 3-methyl-phenyl |
| A-549 | ethyl | 4-methyl-phenyl |
| A-550 | i-propyl | H |
| A-551 | i-propyl | CH₃ |
| A-552 | i-propyl | CH₂CH₃ |
| A-553 | i-propyl | CH₂CH₂CH₃ |
| A-554 | i-propyl | CH(CH₃)₂ |
| A-555 | i-propyl | CH₂CH₂CH₂CH₃ |
| A-556 | i-propyl | CH(CH₃)CH₂CH₃ |
| A-557 | i-propyl | CH₂CH(CH₃)CH₃ |
| A-558 | i-propyl | C(CH₃)₃ |
| A-559 | i-propyl | C(=O)—CH₃ |
| A-560 | i-propyl | C(=O)—CH₂CH₃ |
| A-561 | i-propyl | C(=O)—CH₂CH₂CH₃ |
| A-562 | i-propyl | C(=O)—CH(CH₃)₂ |
| A-563 | i-propyl | C(=O)—CH₂CH₂CH₂CH₃ |
| A-564 | i-propyl | C(=O)—CH(CH₃)CH₂CH₃ |
| A-565 | i-propyl | C(=O)—CH₂CH(CH₃)CH₃ |
| A-566 | i-propyl | C(=O)—C(CH₃)₃ |
| A-567 | i-propyl | C(=O)—CH₂CH₂CH₂CH₂CH₃ |
| A-568 | i-propyl | C(=O)—CH(CH₃)CH₂CH₂CH₃ |
| A-569 | i-propyl | C(=O)—CH₂CH(CH₃)CH₂CH₃ |
| A-570 | i-propyl | C(=O)—CH₂CH₂CH(CH₃)CH₃ |
| A-571 | i-propyl | C(=O)—CH(CH₂CH₃)CH₂CH₃ |
| A-572 | i-propyl | C(=O)—OCH₃ |
| A-573 | i-propyl | C(=O)—OCH₂CH₃ |
| A-574 | i-propyl | C(=O)—OCH₂CH₂CH₃ |
| A-575 | i-propyl | C(=O)—OCH(CH₃)₂ |
| A-576 | i-propyl | C(=O)—OCH₂CH₂CH₂CH₃ |
| A-577 | i-propyl | C(=O)—OCH(CH₃)CH₂CH₃ |
| A-578 | i-propyl | C(=O)—OCH₂CH(CH₃)CH₃ |
| A-579 | i-propyl | C(=O)—OC(CH₃)₃ |
| A-580 | i-propyl | C(=O)—OCH₂CH₂CH₂CH₂CH₃ |
| A-581 | i-propyl | C(=O)—OCH(CH₃)CH₂CH₂CH₃ |
| A-582 | i-propyl | C(=O)—OCH₂CH(CH₃)CH₂CH₃ |
| A-583 | i-propyl | C(=O)—OCH₂CH₂CH(CH₃)CH₃ |
| A-584 | i-propyl | C(=O)—OCH(CH₂CH₃)CH₂CH₃ |
| A-585 | i-propyl | allyl |
| A-586 | i-propyl | propargyl |
| A-587 | i-propyl | cyclopropyl |
| A-588 | i-propyl | cylopentyl |
| A-589 | i-propyl | cyclohexyl |
| A-590 | i-propyl | phenyl |
| A-591 | i-propyl | 2-pyridyl |
| A-592 | i-propyl | 3-pyridyl |
| A-593 | i-propyl | 4-pyridyl |
| A-594 | i-propyl | 2-F-phenyl |
| A-595 | i-propyl | 3-F-phenyl |
| A-596 | i-propyl | 4-F-phenyl |
| A-597 | i-propyl | 2-Cl-phenyl |
| A-598 | i-propyl | 3-Cl-phenyl |
| A-599 | i-propyl | 4-Cl-phenyl |
| A-600 | i-propyl | 2-methyl-phenyl |
| A-601 | i-propyl | 3-methyl-phenyl |
| A-602 | i-propyl | 4-methyl-phenyl |
| A-603 | n-propyl | H |
| A-604 | n-propyl | CH₃ |
| A-605 | n-propyl | CH₂CH₃ |
| A-606 | n-propyl | CH₂CH₂CH₃ |
| A-607 | n-propyl | CH(CH₃)₂ |
| A-608 | n-propyl | CH₂CH₂CH₂CH₃ |
| A-609 | n-propyl | CH(CH₃)CH₂CH₃ |
| A-610 | n-propyl | CH₂CH(CH₃)CH₃ |
| A-611 | n-propyl | C(CH₃)₃ |
| A-612 | n-propyl | C(=O)—CH₃ |
| A-613 | n-propyl | C(=O)—CH₂CH₃ |
| A-614 | n-propyl | C(=O)—CH₂CH₂CH₃ |
| A-615 | n-propyl | C(=O)—CH(CH₃)₂ |
| A-616 | n-propyl | C(=O)—CH₂CH₂CH₂CH₃ |
| A-617 | n-propyl | C(=O)—CH(CH₃)CH₂CH₃ |
| A-618 | n-propyl | C(=O)—CH₂CH(CH₃)CH₃ |
| A-619 | n-propyl | C(=O)—C(CH₃)₃ |
| A-620 | n-propyl | C(=O)—CH₂CH₂CH₂CH₂CH₃ |
| A-621 | n-propyl | C(=O)—CH(CH₃)CH₂CH₂CH₃ |
| A-622 | n-propyl | C(=O)—CH₂CH(CH₃)CH₂CH₃ |
| A-623 | n-propyl | C(=O)—CH₂CH₂CH(CH₃)CH₃ |
| A-624 | n-propyl | C(=O)—CH(CH₂CH₃)CH₂CH₃ |
| A-625 | n-propyl | C(=O)—OCH₃ |
| A-626 | n-propyl | C(=O)—OCH₂CH₃ |
| A-627 | n-propyl | C(=O)—OCH₂CH₂CH₃ |
| A-628 | n-propyl | C(=O)—OCH(CH₃)₂ |
| A-629 | n-propyl | C(=O)—OCH₂CH₂CH₂CH₃ |
| A-630 | n-propyl | C(=O)—OCH(CH₃)CH₂CH₃ |
| A-631 | n-propyl | C(=O)—OCH₂CH(CH₃)CH₃ |
| A-632 | n-propyl | C(=O)—OC(CH₃)₃ |
| A-633 | n-propyl | C(=O)—OCH₂CH₂CH₂CH₂CH₃ |
| A-634 | n-propyl | C(=O)—OCH(CH₃)CH₂CH₂CH₃ |
| A-635 | n-propyl | C(=O)—OCH₂CH(CH₃)CH₂CH₃ |
| A-636 | n-propyl | C(=O)—OCH₂CH₂CH(CH₃)CH₃ |
| A-637 | n-propyl | C(=O)—OCH(CH₂CH₃)CH₂CH₃ |
| A-638 | n-propyl | allyl |
| A-639 | n-propyl | propargyl |
| A-640 | n-propyl | cyclopropyl |
| A-641 | n-propyl | cylopentyl |
| A-642 | n-propyl | cyclohexyl |
| A-643 | n-propyl | phenyl |
| A-644 | n-propyl | 2-pyridyl |
| A-645 | n-propyl | 3-pyridyl |
| A-646 | n-propyl | 4-pyridyl |
| A-647 | n-propyl | 2-F-phenyl |
| A-648 | n-propyl | 3-F-phenyl |
| A-649 | n-propyl | 4-F-phenyl |
| A-650 | n-propyl | 2-Cl-phenyl |
| A-651 | n-propyl | 3-Cl-phenyl |
| A-652 | n-propyl | 4-Cl-phenyl |
| A-653 | n-propyl | 2-methyl-phenyl |
| A-654 | n-propyl | 3-methyl-phenyl |
| A-655 | n-propyl | 4-methyl-phenyl |
| A-656 | allyl | H |
| A-657 | allyl | CH₃ |
| A-658 | allyl | CH₂CH₃ |
| A-659 | allyl | CH₂CH₂CH₃ |
| A-660 | allyl | CH(CH₃)₂ |
| A-661 | allyl | CH₂CH₂CH₂CH₃ |
| A-662 | allyl | CH(CH₃)CH₂CH₃ |
| A-663 | allyl | CH₂CH(CH₃)CH₃ |
| A-664 | allyl | C(CH₃)₃ |
| A-665 | allyl | C(=O)—CH₃ |
| A-666 | allyl | C(=O)—CH₂CH₃ |
| A-667 | allyl | C(=O)—CH₂CH₂CH₃ |
| A-668 | allyl | C(=O)—CH(CH₃)₂ |
| A-669 | allyl | C(=O)—CH₂CH₂CH₂CH₃ |
| A-670 | allyl | C(=O)—CH(CH₃)CH₂CH₃ |
| A-671 | allyl | C(=O)—CH₂CH(CH₃)CH₃ |
| A-672 | allyl | C(=O)—C(CH₃)₃ |
| A-673 | allyl | C(=O)—CH₂CH₂CH₂CH₂CH₃ |
| A-674 | allyl | C(=O)—CH(CH₃)CH₂CH₂CH₃ |
| A-675 | allyl | C(=O)—CH₂CH(CH₃)CH₂CH₃ |
| A-676 | allyl | C(=O)—CH₂CH₂CH(CH₃)CH₃ |
| A-677 | allyl | C(=O)—CH(CH₂CH₃)CH₂CH₃ |
| A-678 | allyl | C(=O)—OCH₃ |
| A-679 | allyl | C(=O)—OCH₂CH₃ |

TABLE A-continued

| No | R¹ | R² |
|---|---|---|
| A-680 | allyl | C(=O)—OCH$_2$CH$_2$CH$_3$ |
| A-681 | allyl | C(=O)—OCH(CH$_3$)$_2$ |
| A-682 | allyl | C(=O)—OCH$_2$CH$_2$CH$_2$CH$_3$ |
| A-683 | allyl | C(=O)—OCH(CH$_3$)CH$_2$CH$_3$ |
| A-684 | allyl | C(=O)—OCH$_2$CH(CH$_3$)CH$_3$ |
| A-685 | allyl | C(=O)—OC(CH$_3$)$_3$ |
| A-686 | allyl | C(=O)—OCH$_2$CH$_2$CH$_2$CH$_2$CH$_3$ |
| A-687 | allyl | C(=O)—OCH(CH$_3$)CH$_2$CH$_2$CH$_3$ |
| A-688 | allyl | C(=O)—OCH$_2$CH(CH$_3$)CH$_2$CH$_3$ |
| A-689 | allyl | C(=O)—OCH$_2$CH$_2$CH(CH$_3$)CH$_3$ |
| A-690 | allyl | C(=O)—OCH(CH$_2$CH$_3$)CH$_2$CH$_3$ |
| A-691 | allyl | allyl |
| A-692 | allyl | propargyl |
| A-693 | allyl | cyclopropyl |
| A-694 | allyl | cylopentyl |
| A-695 | allyl | cyclohexyl |
| A-696 | allyl | phenyl |
| A-697 | allyl | 2-pyridyl |
| A-698 | allyl | 3-pyridyl |
| A-699 | allyl | 4-pyridyl |
| A-700 | allyl | 2-F-phenyl |
| A-701 | allyl | 3-F-phenyl |
| A-702 | allyl | 4-F-phenyl |
| A-703 | allyl | 2-Cl-phenyl |
| A-704 | allyl | 3-Cl-phenyl |
| A-705 | allyl | 4-Cl-phenyl |
| A-706 | allyl | 2-methyl-phenyl |
| A-707 | allyl | 3-methyl-phenyl |
| A-708 | allyl | 4-methyl-phenyl |
| A-709 | tert-butyl | H |
| A-710 | tert-butyl | CH$_3$ |
| A-711 | tert-butyl | CH$_2$CH$_3$ |
| A-712 | tert-butyl | CH$_2$CH$_2$CH$_3$ |
| A-713 | tert-butyl | CH(CH$_3$)$_2$ |
| A-714 | tert-butyl | CH$_2$CH$_2$CH$_2$CH$_3$ |
| A-715 | tert-butyl | CH(CH$_3$)CH$_2$CH$_3$ |
| A-716 | tert-butyl | CH$_2$CH(CH$_3$)CH$_3$ |
| A-717 | tert-butyl | C(CH$_3$)$_3$ |
| A-718 | tert-butyl | C(=O)—CH$_3$ |
| A-719 | tert-butyl | C(=O)—CH$_2$CH$_3$ |
| A-720 | tert-butyl | C(=O)—CH$_2$CH$_2$CH$_3$ |
| A-721 | tert-butyl | C(=O)—CH(CH$_3$)$_2$ |
| A-722 | tert-butyl | C(=O)—CH$_2$CH$_2$CH$_2$CH$_3$ |
| A-723 | tert-butyl | C(=O)—CH(CH$_3$)CH$_2$CH$_3$ |
| A-724 | tert-butyl | C(=O)—CH$_2$CH(CH$_3$)CH$_3$ |
| A-725 | tert-butyl | C(=O)—C(CH$_3$)$_3$ |
| A-726 | tert-butyl | C(=O)—CH$_2$CH$_2$CH$_2$CH$_2$CH$_3$ |
| A-727 | tert-butyl | C(=O)—CH(CH$_3$)CH$_2$CH$_2$CH$_3$ |
| A-728 | tert-butyl | C(=O)—CH$_2$CH(CH$_3$)CH$_2$CH$_3$ |
| A-729 | tert-butyl | C(=O)—CH$_2$CH$_2$CH(CH$_3$)CH$_3$ |
| A-730 | tert-butyl | C(=O)—CH(CH$_2$CH$_3$)CH$_2$CH$_3$ |
| A-731 | tert-butyl | C(=O)—OCH$_3$ |
| A-732 | tert-butyl | C(=O)—OCH$_2$CH$_3$ |
| A-733 | tert-butyl | C(=O)—OCH$_2$CH$_2$CH$_3$ |
| A-734 | tert-butyl | C(=O)—OCH(CH$_3$)$_2$ |
| A-735 | tert-butyl | C(=O)—OCH$_2$CH$_2$CH$_2$CH$_3$ |
| A-736 | tert-butyl | C(=O)—OCH(CH$_3$)CH$_2$CH$_3$ |
| A-737 | tert-butyl | C(=O)—OCH$_2$CH(CH$_3$)CH$_3$ |
| A-738 | tert-butyl | C(=O)—OC(CH$_3$)$_3$ |
| A-739 | tert-butyl | C(=O)—OCH$_2$CH$_2$CH$_2$CH$_2$CH$_3$ |
| A-740 | tert-butyl | C(=O)—OCH(CH$_3$)CH$_2$CH$_2$CH$_3$ |
| A-741 | tert-butyl | C(=O)—OCH$_2$CH(CH$_3$)CH$_2$CH$_3$ |
| A-742 | tert-butyl | C(=O)—OCH$_2$CH$_2$CH(CH$_3$)CH$_3$ |
| A-743 | tert-butyl | C(=O)—OCH(CH$_2$CH$_3$)CH$_2$CH$_3$ |
| A-744 | tert-butyl | allyl |
| A-745 | tert-butyl | propargyl |
| A-746 | tert-butyl | cyclopropyl |
| A-747 | tert-butyl | cylopentyl |
| A-748 | tert-butyl | cyclohexyl |
| A-749 | tert-butyl | phenyl |
| A-750 | tert-butyl | 2-pyridyl |
| A-751 | tert-butyl | 3-pyridyl |
| A-752 | tert-butyl | 4-pyridyl |
| A-753 | tert-butyl | 2-F-phenyl |
| A-754 | tert-butyl | 3-F-phenyl |
| A-755 | tert-butyl | 4-F-phenyl |
| A-756 | tert-butyl | 2-Cl-phenyl |
| A-757 | tert-butyl | 3-Cl-phenyl |
| A-758 | tert-butyl | 4-Cl-phenyl |
| A-759 | tert-butyl | 2-methyl-phenyl |
| A-760 | tert-butyl | 3-methyl-phenyl |
| A-761 | tert-butyl | 4-methyl-phenyl |
| A-762 | phenyl | H |
| A-763 | phenyl | CH$_3$ |
| A-764 | phenyl | CH$_2$CH$_3$ |
| A-765 | phenyl | CH$_2$CH$_2$CH$_3$ |
| A-766 | phenyl | CH(CH$_3$)$_2$ |
| A-767 | phenyl | CH$_2$CH$_2$CH$_2$CH$_3$ |
| A-768 | phenyl | CH(CH$_3$)CH$_2$CH$_3$ |
| A-769 | phenyl | CH$_2$CH(CH$_3$)CH$_3$ |
| A-770 | phenyl | C(CH$_3$)$_3$ |
| A-771 | phenyl | C(=O)—CH$_3$ |
| A-772 | phenyl | C(=O)—CH$_2$CH$_3$ |
| A-773 | phenyl | C(=O)—CH$_2$CH$_2$CH$_3$ |
| A-774 | phenyl | C(=O)—CH(CH$_3$)$_2$ |
| A-775 | phenyl | C(=O)—CH$_2$CH$_2$CH$_2$CH$_3$ |
| A-776 | phenyl | C(=O)—CH(CH$_3$)CH$_2$CH$_3$ |
| A-777 | phenyl | C(=O)—CH$_2$CH(CH$_3$)CH$_3$ |
| A-778 | phenyl | C(=O)—C(CH$_3$)$_3$ |
| A-779 | phenyl | C(=O)—CH$_2$CH$_2$CH$_2$CH$_2$CH$_3$ |
| A-780 | phenyl | C(=O)—CH(CH$_3$)CH$_2$CH$_2$CH$_3$ |
| A-781 | phenyl | C(=O)—CH$_2$CH(CH$_3$)CH$_2$CH$_3$ |
| A-782 | phenyl | C(=O)—CH$_2$CH$_2$CH(CH$_3$)CH$_3$ |
| A-783 | phenyl | C(=O)—CH(CH$_2$CH$_3$)CH$_2$CH$_3$ |
| A-784 | phenyl | C(=O)—OCH$_3$ |
| A-785 | phenyl | C(=O)—OCH$_2$CH$_3$ |
| A-786 | phenyl | C(=O)—OCH$_2$CH$_2$CH$_3$ |
| A-787 | phenyl | C(=O)—OCH(CH$_3$)$_2$ |
| A-788 | phenyl | C(=O)—OCH$_2$CH$_2$CH$_2$CH$_3$ |
| A-789 | phenyl | C(=O)—OCH(CH$_3$)CH$_2$CH$_3$ |
| A-790 | phenyl | C(=O)—OCH$_2$CH(CH$_3$)CH$_3$ |
| A-791 | phenyl | C(=O)—OC(CH$_3$)$_3$ |
| A-792 | phenyl | C(=O)—OCH$_2$CH$_2$CH$_2$CH$_2$CH$_3$ |
| A-793 | phenyl | C(=O)—OCH(CH$_3$)CH$_2$CH$_2$CH$_3$ |
| A-794 | phenyl | C(=O)—OCH$_2$CH(CH$_3$)CH$_2$CH$_3$ |
| A-795 | phenyl | C(=O)—OCH$_2$CH$_2$CH(CH$_3$)CH$_3$ |
| A-796 | phenyl | C(=O)—OCH(CH$_2$CH$_3$)CH$_2$CH$_3$ |
| A-797 | phenyl | allyl |
| A-798 | phenyl | propargyl |
| A-799 | phenyl | cyclopropyl |
| A-800 | phenyl | cylopentyl |
| A-801 | phenyl | cyclohexyl |
| A-802 | phenyl | phenyl |
| A-803 | phenyl | 2-pyridyl |
| A-804 | phenyl | 3-pyridyl |
| A-805 | phenyl | 4-pyridyl |
| A-806 | phenyl | 2-F-phenyl |
| A-807 | phenyl | 3-F-phenyl |
| A-808 | phenyl | 4-F-phenyl |
| A-809 | phenyl | 2-Cl-phenyl |
| A-810 | phenyl | 3-Cl-phenyl |
| A-811 | phenyl | 4-Cl-phenyl |
| A-812 | phenyl | 2-methyl-phenyl |
| A-813 | phenyl | 3-methyl-phenyl |
| A-814 | phenyl | 4-methyl-phenyl |
| A-815 | CF$_3$ | H |
| A-816 | CF$_3$ | CH$_3$ |
| A-817 | CF$_3$ | CH$_2$CH$_3$ |
| A-818 | CF$_3$ | CH$_2$CH$_2$CH$_3$ |
| A-819 | CF$_3$ | CH(CH$_3$)$_2$ |
| A-820 | CF$_3$ | CH$_2$CH$_2$CH$_2$CH$_3$ |
| A-821 | CF$_3$ | CH(CH$_3$)CH$_2$CH$_3$ |
| A-822 | CF$_3$ | CH$_2$CH(CH$_3$)CH$_3$ |
| A-823 | CF$_3$ | C(CH$_3$)$_3$ |
| A-824 | CF$_3$ | C(=O)—CH$_3$ |
| A-825 | CF$_3$ | C(=O)—CH$_2$CH$_3$ |
| A-826 | CF$_3$ | C(=O)—CH$_2$CH$_2$CH$_3$ |
| A-827 | CF$_3$ | C(=O)—CH(CH$_3$)$_2$ |
| A-828 | CF$_3$ | C(=O)—CH$_2$CH$_2$CH$_2$CH$_3$ |
| A-829 | CF$_3$ | C(=O)—CH(CH$_3$)CH$_2$CH$_3$ |
| A-830 | CF$_3$ | C(=O)—CH$_2$CH(CH$_3$)CH$_3$ |
| A-831 | CF$_3$ | C(=O)—C(CH$_3$)$_3$ |
| A-832 | CF$_3$ | C(=O)—CH$_2$CH$_2$CH$_2$CH$_2$CH$_3$ |
| A-833 | CF$_3$ | C(=O)—CH(CH$_3$)CH$_2$CH$_2$CH$_3$ |
| A-834 | CF$_3$ | C(=O)—CH$_2$CH(CH$_3$)CH$_2$CH$_3$ |
| A-835 | CF$_3$ | C(=O)—CH$_2$CH$_2$CH(CH$_3$)CH$_3$ |

TABLE A-continued

| No | R$^1$ | R$^2$ |
|---|---|---|
| A-836 | CF$_3$ | C(=O)—CH(CH$_2$CH$_3$)CH$_2$CH$_3$ |
| A-837 | CF$_3$ | C(=O)—OCH$_3$ |
| A-838 | CF$_3$ | C(=O)—OCH$_2$CH$_3$ |
| A-839 | CF$_3$ | C(=O)—OCH$_2$CH$_2$CH$_3$ |
| A-840 | CF$_3$ | C(=O)—OCH(CH$_3$)$_2$ |
| A-841 | CF$_3$ | C(=O)—OCH$_2$CH$_2$CH$_2$CH$_3$ |
| A-842 | CF$_3$ | C(=O)—OCH(CH$_3$)CH$_2$CH$_3$ |
| A-843 | CF$_3$ | C(=O)—OCH$_2$CH(CH$_3$)CH$_3$ |
| A-844 | CF$_3$ | C(=O)—OC(CH$_3$)$_3$ |
| A-845 | CF$_3$ | C(=O)—OCH$_2$CH$_2$CH$_2$CH$_2$CH$_3$ |
| A-846 | CF$_3$ | C(=O)—OCH(CH$_3$)CH$_2$CH$_2$CH$_3$ |
| A-847 | CF$_3$ | C(=O)—OCH$_2$CH(CH$_3$)CH$_2$CH$_3$ |
| A-848 | CF$_3$ | C(=O)—OCH$_2$CH$_2$CH(CH$_3$)CH$_3$ |
| A-849 | CF$_3$ | C(=O)—OCH(CH$_2$CH$_3$)CH$_2$CH$_3$ |
| A-850 | CF$_3$ | allyl |
| A-851 | CF$_3$ | propargyl |
| A-852 | CF$_3$ | cyclopropyl |
| A-853 | CF$_3$ | cylopentyl |
| A-854 | CF$_3$ | cyclohexyl |
| A-855 | CF$_3$ | phenyl |
| A-856 | CF$_3$ | 2-pyridyl |
| A-857 | CF$_3$ | 3-pyridyl |
| A-858 | CF$_3$ | 4-pyridyl |
| A-859 | CF$_3$ | 2-F-phenyl |
| A-860 | CF$_3$ | 3-F-phenyl |
| A-861 | CF$_3$ | 4-F-phenyl |
| A-862 | CF$_3$ | 2-Cl-phenyl |
| A-863 | CF$_3$ | 3-Cl-phenyl |
| A-864 | CF$_3$ | 4-Cl-phenyl |
| A-865 | CF$_3$ | 2-methyl-phenyl |
| A-866 | CF$_3$ | 3-methyl-phenyl |
| A-867 | CF$_3$ | 4-methyl-phenyl |
| A-868 | CH$_2$CF$_3$ | H |
| A-869 | CH$_2$CF$_3$ | CH$_3$ |
| A-870 | CH$_2$CF$_3$ | CH$_2$CH$_3$ |
| A-871 | CH$_2$CF$_3$ | CH$_2$CH$_2$CH$_3$ |
| A-872 | CH$_2$CF$_3$ | CH(CH$_3$)$_2$ |
| A-873 | CH$_2$CF$_3$ | CH$_2$CH$_2$CH$_2$CH$_3$ |
| A-874 | CH$_2$CF$_3$ | CH(CH$_3$)CH$_2$CH$_3$ |
| A-875 | CH$_2$CF$_3$ | CH$_2$CH(CH$_3$)CH$_3$ |
| A-876 | CH$_2$CF$_3$ | C(CH$_3$)$_3$ |
| A-877 | CH$_2$CF$_3$ | C(=O)—CH$_3$ |
| A-878 | CH$_2$CF$_3$ | C(=O)—CH$_2$CH$_3$ |
| A-879 | CH$_2$CF$_3$ | C(=O)—CH$_2$CH$_2$CH$_3$ |
| A-880 | CH$_2$CF$_3$ | C(=O)—CH(CH$_3$)$_2$ |
| A-881 | CH$_2$CF$_3$ | C(=O)—CH$_2$CH$_2$CH$_2$CH$_3$ |
| A-882 | CH$_2$CF$_3$ | C(=O)—CH(CH$_3$)CH$_2$CH$_3$ |
| A-883 | CH$_2$CF$_3$ | C(=O)—CH$_2$CH(CH$_3$)CH$_3$ |
| A-884 | CH$_2$CF$_3$ | C(=O)—C(CH$_3$)$_3$ |
| A-885 | CH$_2$CF$_3$ | C(=O)—CH$_2$CH$_2$CH$_2$CH$_2$CH$_3$ |
| A-886 | CH$_2$CF$_3$ | C(=O)—CH(CH$_3$)CH$_2$CH$_2$CH$_3$ |
| A-887 | CH$_2$CF$_3$ | C(=O)—CH$_2$CH(CH$_3$)CH$_2$CH$_3$ |
| A-888 | CH$_2$CF$_3$ | C(=O)—CH$_2$CH$_2$CH(CH$_3$)CH$_3$ |
| A-889 | CH$_2$CF$_3$ | C(=O)—CH(CH$_2$CH$_3$)CH$_2$CH$_3$ |
| A-890 | CH$_2$CF$_3$ | C(=O)—OCH$_3$ |
| A-891 | CH$_2$CF$_3$ | C(=O)—OCH$_2$CH$_3$ |
| A-892 | CH$_2$CF$_3$ | C(=O)—OCH$_2$CH$_2$CH$_3$ |
| A-893 | CH$_2$CF$_3$ | C(=O)—OCH(CH$_3$)$_2$ |
| A-894 | CH$_2$CF$_3$ | C(=O)—OCH$_2$CH$_2$CH$_2$CH$_3$ |
| A-895 | CH$_2$CF$_3$ | C(=O)—OCH(CH$_3$)CH$_2$CH$_3$ |
| A-896 | CH$_2$CF$_3$ | C(=O)—OCH$_2$CH(CH$_3$)CH$_3$ |
| A-897 | CH$_2$CF$_3$ | C(=O)—OC(CH$_3$)$_3$ |
| A-898 | CH$_2$CF$_3$ | C(=O)—OCH$_2$CH$_2$CH$_2$CH$_2$CH$_3$ |
| A-899 | CH$_2$CF$_3$ | C(=O)—OCH(CH$_3$)CH$_2$CH$_2$CH$_3$ |
| A-900 | CH$_2$CF$_3$ | C(=O)—OCH$_2$CH(CH$_3$)CH$_2$CH$_3$ |
| A-901 | CH$_2$CF$_3$ | C(=O)—OCH$_2$CH$_2$CH(CH$_3$)CH$_3$ |
| A-902 | CH$_2$CF$_3$ | C(=O)—OCH(CH$_2$CH$_3$)CH$_2$CH$_3$ |
| A-903 | CH$_2$CF$_3$ | allyl |
| A-904 | CH$_2$CF$_3$ | propargyl |
| A-905 | CH$_2$CF$_3$ | cyclopropyl |
| A-906 | CH$_2$CF$_3$ | cylopentyl |
| A-907 | CH$_2$CF$_3$ | cyclohexyl |
| A-908 | CH$_2$CF$_3$ | phenyl |
| A-909 | CH$_2$CF$_3$ | 2-pyridyl |
| A-910 | CH$_2$CF$_3$ | 3-pyridyl |
| A-911 | CH$_2$CF$_3$ | 4-pyridyl |
| A-912 | CH$_2$CF$_3$ | 2-F-phenyl |
| A-913 | CH$_2$CF$_3$ | 3-F-phenyl |
| A-914 | CH$_2$CF$_3$ | 4-F-phenyl |
| A-915 | CH$_2$CF$_3$ | 2-Cl-phenyl |
| A-916 | CH$_2$CF$_3$ | 3-Cl-phenyl |
| A-917 | CH$_2$CF$_3$ | 4-Cl-phenyl |
| A-918 | CH$_2$CF$_3$ | 2-methyl-phenyl |
| A-919 | CH$_2$CF$_3$ | 3-methyl-phenyl |
| A-920 | CH$_2$CF$_3$ | 4-methyl-phenyl |
| A-921 | cyclopropyl | H |
| A-922 | cyclopropyl | CH$_3$ |
| A-923 | cyclopropyl | CH$_2$CH$_3$ |
| A-924 | cyclopropyl | CH$_2$CH$_2$CH$_3$ |
| A-925 | cyclopropyl | CH(CH$_3$)$_2$ |
| A-926 | cyclopropyl | CH$_2$CH$_2$CH$_2$CH$_3$ |
| A-927 | cyclopropyl | CH(CH$_3$)CH$_2$CH$_3$ |
| A-928 | cyclopropyl | CH$_2$CH(CH$_3$)CH$_3$ |
| A-929 | cyclopropyl | C(CH$_3$)$_3$ |
| A-930 | cyclopropyl | C(=O)—CH$_3$ |
| A-931 | cyclopropyl | C(=O)—CH$_2$CH$_3$ |
| A-932 | cyclopropyl | C(=O)—CH$_2$CH$_2$CH$_3$ |
| A-933 | cyclopropyl | C(=O)—CH(CH$_3$)$_2$ |
| A-934 | cyclopropyl | C(=O)—CH$_2$CH$_2$CH$_2$CH$_3$ |
| A-935 | cyclopropyl | C(=O)—CH(CH$_3$)CH$_2$CH$_3$ |
| A-936 | cyclopropyl | C(=O)—CH$_2$CH(CH$_3$)CH$_3$ |
| A-937 | cyclopropyl | C(=O)—C(CH$_3$)$_3$ |
| A-938 | cyclopropyl | C(=O)—CH$_2$CH$_2$CH$_2$CH$_2$CH$_3$ |
| A-939 | cyclopropyl | C(=O)—CH(CH$_3$)CH$_2$CH$_2$CH$_3$ |
| A-940 | cyclopropyl | C(=O)—CH$_2$CH(CH$_3$)CH$_2$CH$_3$ |
| A-941 | cyclopropyl | C(=O)—CH$_2$CH$_2$CH(CH$_3$)CH$_3$ |
| A-942 | cyclopropyl | C(=O)—CH(CH$_2$CH$_3$)CH$_2$CH$_3$ |
| A-943 | cyclopropyl | C(=O)—OCH$_3$ |
| A-944 | cyclopropyl | C(=O)—OCH$_2$CH$_3$ |
| A-945 | cyclopropyl | C(=O)—OCH$_2$CH$_2$CH$_3$ |
| A-946 | cyclopropyl | C(=O)—OCH(CH$_3$)$_2$ |
| A-947 | cyclopropyl | C(=O)—OCH$_2$CH$_2$CH$_2$CH$_3$ |
| A-948 | cyclopropyl | C(=O)—OCH(CH$_3$)CH$_2$CH$_3$ |
| A-949 | cyclopropyl | C(=O)—OCH$_2$CH(CH$_3$)CH$_3$ |
| A-950 | cyclopropyl | C(=O)—OC(CH$_3$)$_3$ |
| A-951 | cyclopropyl | C(=O)—OCH$_2$CH$_2$CH$_2$CH$_2$CH$_3$ |
| A-952 | cyclopropyl | C(=O)—OCH(CH$_3$)CH$_2$CH$_2$CH$_3$ |
| A-953 | cyclopropyl | C(=O)—OCH$_2$CH(CH$_3$)CH$_2$CH$_3$ |
| A-954 | cyclopropyl | C(=O)—OCH$_2$CH$_2$CH(CH$_3$)CH$_3$ |
| A-955 | cyclopropyl | C(=O)—OCH(CH$_2$CH$_3$)CH$_2$CH$_3$ |
| A-956 | cyclopropyl | allyl |
| A-957 | cyclopropyl | propargyl |
| A-958 | cyclopropyl | cyclopropyl |
| A-959 | cyclopropyl | cylopentyl |
| A-960 | cyclopropyl | cyclohexyl |
| A-961 | cyclopropyl | phenyl |
| A-962 | cyclopropyl | 2-pyridyl |
| A-963 | cyclopropyl | 3-pyridyl |
| A-964 | cyclopropyl | 4-pyridyl |
| A-965 | cyclopropyl | 2-F-phenyl |
| A-966 | cyclopropyl | 3-F-phenyl |
| A-967 | cyclopropyl | 4-F-phenyl |
| A-968 | cyclopropyl | 2-Cl-phenyl |
| A-969 | cyclopropyl | 3-Cl-phenyl |
| A-970 | cyclopropyl | 4-Cl-phenyl |
| A-971 | cyclopropyl | 2-methyl-phenyl |
| A-972 | cyclopropyl | 3-methyl-phenyl |
| A-973 | cyclopropyl | 4-methyl-phenyl |

The compounds of the formula I can be prepared according to methods or in analogy to methods that are described in the prior art. The synthesis takes advantage of starting materials that are commercially available or may be prepared according to conventional procedures starting from readily available compounds. For example, compounds of the formula I can be prepared by reacting amidines of type II with trifluoroacetic anhydride in an organic solvent, preferably an ethereal solvent at temperatures between 0° C. and 100° C., preferably at room temperature, as previously described in WO2013/008162.

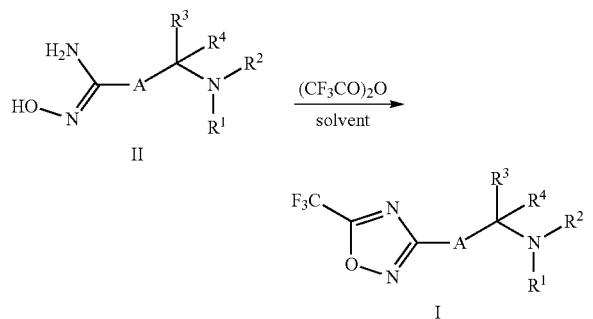

A skilled person will recognize that compounds of type II can be accessed by treating nitriles of type III with hydroxylamine (or its HCl salt) in an organic solvent and in the presence of a base (for precedents see for example WO2009/074950, WO2006/013104, EP1932843).

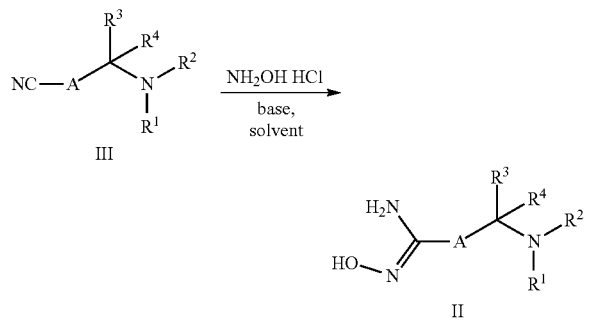

Compounds III can be prepared by reacting carbonyl compound of type IV with the respective amine in an organic solvent and in the presence of a base, followed by subsequent treatment of the intermediary iminium species V with an organometallic reagent or hydride (if R4=H). If appropriate, the iminium species V may be isolated. The reaction is performed preferably in an ethereal solvent and at temperatures between −78° C. and 40° C., more preferably at −15° C. or at room temperature as previously described (see for example Tetrahedron Letters 52(2), 281-284, 2011 or Journal of Organic Chemistry, 70(5), 1930-1933, 2005).

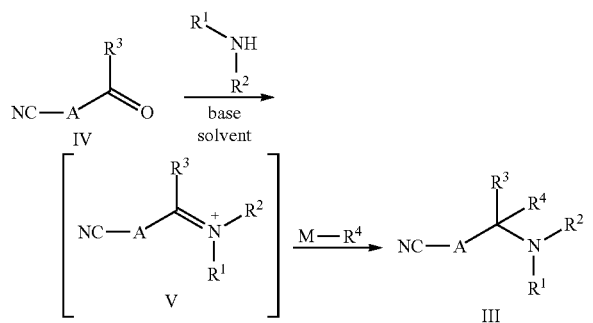

Compounds IV are either commercially available or can be accessed through known methods that are obvious for a person skilled in the art.

The compounds of the formula I or compositions comprising said compounds according to the invention and the mixtures comprising said compounds and compositions, respectively, are suitable as fungicides. They are distinguished by an outstanding effectiveness against a broad spectrum of phytopathogenic fungi, including soil-borne fungi, which derive especially from the following classes or are closely related to any of them: *Ascomycota* (*Ascomycetes*), for example, but not limited to the genus *Cocholiobolus, Colletotrichum, Fusarium, Microdochium, Penicillium, Phoma, Magnaporte, Zymoseptoria,* and *Pseudocercosporella; Basdiomycota* (*Basidiomycetes*), for example, but not limited to the genus *Phakospora, Puccinia, Rhizoctonia, Sphacelotheca, Tilletia, Typhula,* and *Ustilago; Chytridiomycota* (*Chytridiomycetes*), for example, but not limited to the genus *Chytridiales,* and *Synchytrium; Deuteromycetes* (syn. *Fungi imperfecti*), for example, but not limited to the genus *Ascochyta, Diplock's, Erysiphe, Fusarium, Phomopsis,* and *Pyrenophora; Peronosporomycetes* (syn. *Oomycetes*), for example but not limited to the genus *Peronospora, Pythium, Phytophthora; Plasmodiophoromycetes,* for example but not limited to the genus *Plasmodiophora; Zygomycetes,* for example, but not limited to the genus *Rhizopus.*

Some of the compounds of the formula I and the compositions according to the invention are systemically effective and they can be used in crop protection as foliar fungicides, fungicides for seed dressing and soil fungicides. Moreover, they are suitable for controlling harmful fungi, which inter alia occur in wood or roots of plants.

The compounds I and the compositions according to the invention are particularly important in the control of a multitude of phytopathogenic fungi on various cultivated plants, such as cereals, e. g. wheat, rye, barley, triticale, oats or rice; beet, e. g. sugar beet or fodder beet; fruits, such as pomes, stone fruits or soft fruits, e. g. apples, pears, plums, peaches, almonds, cherries, strawberries, raspberries, blackberries or gooseberries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, sugar cane or oil palm; corn; tobacco; nuts; coffee; tea; bananas; vines (table grapes and grape juice grape vines); hop; turf; sweet leaf (also called Stevia); natural rubber plants or ornamental and forestry plants, such as flowers, shrubs, broad-leaved trees or evergreens, e. g. conifers; and on the plant propagation material, such as seeds, and the crop material of these plants. Preferably, compounds I and compositions thereof, respectively are used for controlling a multitude of fungi on field crops, such as potatoes sugar beets, tobacco, wheat, rye, barley, oats, rice, corn, cotton, soybeans, rape, legumes, sunflowers, coffee or sugar cane; fruits; vines; ornamentals; or vegetables, such as cucumbers, tomatoes, beans or squashes. The term "plant propagation material" is to be understood to denote all the generative parts of the plant such as seeds and vegetative plant material such as cuttings and tubers (e. g. potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil.

These young plants may also be protected before transplantation by a total or partial treatment by immersion or pouring.

Preferably, treatment of plant propagation materials with compounds I and compositions thereof, respectively, is used for controlling a multitude of fungi on cereals, such as wheat, rye, barley and oats; rice, corn, cotton and soybeans.

The term "cultivated plants" is to be understood as including plants which have been modified by breeding, mutagenesis or genetic engineering including but not limiting to agricultural biotech products on the market or in development (cf. http://cera-gmc.org/, see GM crop database therein). Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-translational modification of protein(s), oligo- or polypeptides e. g. by glycosylation or polymer additions such as prenylated, acetylated or farnesylated moieties or PEG moieties. Plants that have been modified by breeding, mutagenesis or genetic engineering, e. g. have been rendered tolerant to applications of specific classes of herbicides, such as auxin herbicides such as dicamba or 2,4-D; bleacher herbicides such as hydroxylphenylpyruvate dioxygenase (HPPD) inhibitors or phytoene desaturase (PDS) inhibitors; acetolactate synthase (ALS) inhibitors such as sulfonyl ureas or imidazolinones; enolpyruvylshikimate-3-phosphate synthase (EPSPS) inhibitors, such as glyphosate; glutamine synthetase (GS) inhibitors such as glufosinate; protoporphyrinogen-IX oxidase inhibitors; lipid biosynthesis inhibitors such as acetyl CoA carboxylase (ACCase) inhibitors; or oxynil (i. e. bromoxynil or ioxynil) herbicides as a result of conventional methods of breeding or genetic engineering. Furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxin herbicides, or ACCase inhibitors. These herbicide resistance technologies are e. g. described in Pest Managem. Sci. 61, 2005, 246; 61, 2005, 258; 61, 2005, 277; 61, 2005, 269; 61, 2005, 286; 64, 2008, 326; 64, 2008, 332; Weed Sci. 57, 2009, 108; Austral. J. Agricult. Res. 58, 2007, 708; Science 316, 2007, 1185; and references quoted therein. Several cultivated plants have been rendered tolerant to herbicides by conventional methods of breeding (mutagenesis), e. g. Clearfield® summer rape (Canola, BASF SE, Germany) being tolerant to imidazolinones, e. g. imazamox, or ExpressSun® sunflowers (DuPont, USA) being tolerant to sulfonyl ureas, e. g. tribenuron. Genetic engineering methods have been used to render cultivated plants such as soybean, cotton, corn, beets and rape, tolerant to herbicides such as glyphosate and glufosinate, some of which are commercially available under the trade names RoundupReady® (glyphosate-tolerant, Monsanto, U.S.A.), Cultivance® (imidazolinone tolerant, BASF SE, Germany) and LibertyLink® (glufosinate-tolerant, Bayer CropScience, Germany).

Furthermore, plants are also covered that are by the use of recombinant DNA techniques capable to synthesize one or more insecticidal proteins, especially those known from the bacterial genus Bacillus, particularly from Bacillus thuringiensis, such as δ-endotoxins, e. g. CryIA(b), CryIA(c), CryIF, CryIF(a2), CryIIA(b), CryIIIA, CryIIIB(b1) or Cry9c; vegetative insecticidal proteins (VIP), e. g. VIP1, VIP2, VIP3 or VIP3A; insecticidal proteins of bacteria colonizing nematodes, e. g. Photorhabdus spp. or Xenorhabdus spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilbene synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e. g. WO 02/015701). Further examples of such toxins or genetically modified plants capable of synthesizing such toxins are disclosed, e. g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e. g. in the publications mentioned above. These insecticidal proteins contained in the genetically modified plants impart to the plants producing these proteins tolerance to harmful pests from all taxonomic groups of arthropods, especially to beetles (Coeloptera), two-winged insects (Diptera), and moths (Lepidoptera) and to nematodes (Nematoda). Genetically modified plants capable to synthesize one or more insecticidal proteins are, e. g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme phosphinothricin-N-acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf) (potato cultivars producing the Cry3A toxin); Bt-Xtra®, NatureGard®, KnockOut®, BiteGard®, Protecta®, Bt11 (e. g. Agrisure® CB) and Bt176 from Syngenta Seeds SAS, France, (corn cultivars producing the Cry1Ab toxin and PAT enyzme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme). Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e. g. EP-A 392 225), plant disease resistance genes (e. g. potato cultivars, which express resistance genes acting against *Phytophthora infestans* derived from the Mexican wild potato *Solarium bulbocastanum*) or T4-lysozym (e. g. potato cultivars capable of synthesizing these proteins with increased resistance against bacteria such as *Erwinia amylvora*). The methods for producing such genetically modified plants are generally known to the person skilled in the art and are described, e. g. in the publications mentioned above.

Furthermore, plants are also covered that are by the use of recombinant DNA techniques capable to synthesize one or more proteins to increase the productivity (e. g. bio mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e. g. oil crops that produce health-promoting long-chain omega-3 fatty acids or unsaturated omega-9 fatty acids (e. g. Nexera® rape, DOW Agro Sciences, Canada).

Furthermore, plants are also covered that contain by the use of recombinant DNA techniques a modified amount of substances of content or new substances of content, specifically to improve raw material production, e. g. potatoes that produce increased amounts of amylopectin (e. g. Amflora® potato, BASF SE, Germany).

The compounds I and compositions thereof, respectively, are particularly suitable for controlling the following plant diseases:

*Albugo* spp. (white rust) on ornamentals, vegetables (e. g. *A. candida*) and sunflowers (e. g. *A. tragopogonis*); *Alternaria* spp. (*Alternaria* leaf spot) on vegetables, rape (*A. brassicola* or *brassicae*), sugar beets (*A. tenuis*), fruits, rice, soybeans, potatoes (e. g. *A. solani* or *A. altemata*), tomatoes (e. g. *A. solani* or *A. altemata*) and wheat; *Aphanomyces* spp. on sugar beets and vegetables; *Ascochyta* spp. on cereals and vegetables, e. g. *A. tritici* (anthracnose) on wheat and *A. hordei* on barley; *Bipolaris* and *Drechslera* spp. (teleomorph: *Cochliobolus* spp.), e. g. Southern leaf blight (*D. maydls*) or Northern leaf blight (*B. zeicola*) on corn, e. g. spot blotch (*B. soroklnlana*) on cereals and e. g. *B. oryzae* on rice and turfs; *Blumeria* (formerly *Erysiphe*) *graminis* (powdery mildew) on cereals (e. g. on wheat or barley); *Botrytis cinerea* (teleomorph: *Botryotinia fucliana*: grey mold) on fruits and berries (e. g. strawberries), vegetables (e. g. lettuce, carrots, celery and cabbages), rape, flowers, vines, forestry plants and wheat; *Bremla lactucae* (downy mildew) on lettuce; *Ceratocystis* (syn. *Ophlostoma*) spp. (rot or wilt) on broad-leaved trees and evergreens, e. g. *C. ulmi* (Dutch elm disease) on elms; *Cercospora* spp. (*Cercospora* leaf spots) on corn (e. g. Gray leaf spot: *C. zeae-maydis*), rice, sugar beets (e. g. *C. beticola*), sugar cane, vegetables, coffee, soybeans (e. g. *C. sojina* or *C. kikuchil*) and rice; *Cladosporlum* spp. on tomatoes (e. g. *C. fulvum*: leaf mold) and cereals, e. g. *C. herbarum* (black ear) on wheat; *Claviceps purpurea* (ergot) on cereals; *Cochliobolus* (anamorph: *Helminthosporium* of *Bipolaris*) spp. (leaf spots) on corn (*C. carbonum*), cereals (e. g. *C. sativus*, anamorph: *B. sorokiniana*) and rice (e. g. *C. miyabeanus*, anamorph: *H. oryzae*); *Colletotrichum* (teleomorph: *Glomerella*) spp. (anthracnose) on cotton (e. g. *C. gossypil*), corn (e. g. *C. graminicola*: Anthracnose stalk rot), soft fruits, potatoes (e. g. *C. coccodes*: black dot), beans (e. g. *C. lindemuthianum*) and soybeans (e. g. *C. truncatum* or *C. gloeosporioides*); *Corticium* spp., e. g. *C. sasakii* (sheath blight) on rice; *Corynespora cassiicola* (leaf spots) on soybeans and ornamentals; *Cycloconium* spp., e. g. *C. oleaginum* on olive trees; *Cylindrocarpon* spp. (e. g. fruit tree canker or young vine decline, teleomorph: *Nectria* or *Neonectria* spp.) on fruit trees, vines (e. g. *C. liriodendri*, teleomorph: *Neonectria liriodendri*, Black Foot Disease) and ornamentals; *Dematophora* (teleomorph: *Rosellinla*) necatrbc (root and stem rot) on soybeans; *Diaporthe* spp., e. g. *D. phaseolorum* (damping off) on soybeans; *Drechslera* (syn. *Helminthosporium*, teleomorph: *Pyrenophora*) spp. on corn, cereals, such as barley (e. g. *D. teres*, net blotch) and wheat (e. g. *D. tritici-repentis*: tan spot), rice and turf; Esca (dieback, apoplexy) on vines, caused by *Formitiporia* (syn. *Phellinus*) *punctata, F. mediterranea, Phaeomoniella chlamydospora* (earlier *Phaeoacremonium chlamydosporum*), *Phaeoacremonium aleophilum* and/or *Botryosphaeria obtusa*; *Elsinoe* spp. on pome fruits (*E. pyri*), soft fruits (*E. veneta*: anthracnose) and vines (*E. ampelina*: anthracnose); *Entyloma oryzae* (leaf smut) on rice; *Epicoccum* spp. (black mold) on wheat; *Erysiphe* spp. (powdery mildew) on sugar beets (*E. betae*), vegetables (e. g. *E. pisi*), such as cucurbits (e. g. *E. cichoracearum*), cabbages, rape (e. g. *E. cruciferarum*); *Eutypa lata* (*Eutypa* canker or dieback, anamorph: *Cytosporina lata*, syn. *Libertella blepharis*) on fruit trees, vines and ornamental woods; *Exserohilum* (syn. *Helminthosporium*) spp. on corn (e. g. *E. turcicum*); *Fusarium* (teleomorph: *Gibberella*) spp. (wilt, root or stem rot) on various plants, such as *F. gram.nearum* or *F. culmorum* (root rot, scab or head blight) on cereals (e. g. wheat or barley), *F. oxysporum* on tomatoes, *F. solani* (f. sp. *glycines* now syn. *F. virguliforme*) and *F. tucumaniae* and *F. brasilierase* each causing sudden death syndrome on soybeans, and *F. verticillioides* on corn; *Gaeumannomyces graminis* (take-all) on cereals (e. g. wheat or barley) and corn; *Glomerella* spp. on cereals (e. g. *G. zeae*) and rice (e. g. *G. fujikuroi*, Bakanae disease); *Glomerella cingulata* on vines, pome fruits and other plants and *G. gossypii* on cotton; Grainstaining complex on rice; *Guignardia bidwellii* (black rot) on vines; *Gymnosporangium* spp. on rosaceous plants and junipers, e. g. *G. sabinae* (rust) on pears; *Helminthosporium* spp. (syn. *Drechslera*, teleomorph: *Cochliobolus*) on corn, cereals and rice; *Hemlleia* spp., e. g. *H. vastatrix* (coffee leaf rust) on coffee; *Isariopsis clavispora* (syn. *Cladosporium vitis*) on vines; *Macrophomina phaseolina* (syn. *phaseoli*) (root and stem rot) on soybeans and cotton; *Microdochium* (syn. *Fusarium*) *nivale* (pink snow mold) on cereals (e. g. wheat or barley); *Microsphaera diffusa* (powdery mildew) on soybeans; *Monllinia* spp., e. g. *M. laxa, M. fructicola* and *M. fructigena* (bloom and twig blight, brown rot) on stone fruits and other rosaceous plants; *Mycosphaerella* spp. on cereals, bananas, soft fruits and ground nuts, such as e. g. *M. graminicola* (anamorph: *Septoria tritici, Septoria* blotch) on wheat or *M. fifiensis* (black Sigatoka disease) on bananas; *Peronospora* spp. (downy mildew) on cabbage (e. g. *P. brassicae*), rape (e. g. *P. parasitica*), onions (e. g. *P. destructor*), tobacco (*P. tabacina*) and soybeans (e. g. *P. manshurica*); *Phakopsora pachyrhizi* and *P. meibomiae* (soybean rust) on soybeans; *Phialophora* spp. e. g. on vines (e. g. *P. tracheiphlla* and *P. tetraspora*) and soybeans (e. g. *P. gregata*: stem rot); *Phoma lingam* (root and stem rot) on rape and cabbage and *P. betae* (root rot, leaf spot and damping-off) on sugar beets; *Phomopsis* spp. on sunflowers, vines (e. g. *P. viticola*: can and leaf spot) and soybeans (e. g. stem rot: *P. phaseoli*, teleomorph: *Diaporthe phaseolorum*); *Physoderma maydis* (brown spots) on corn; *Phytophthora* spp. (wilt, root, leaf, fruit and stem root) on various plants, such as paprika and cucurbits (e. g. *P. capsici*), soybeans (e. g. *P.* megasperma, syn. *P. sojae*), potatoes and tomatoes (e. g. *P. infestans*: late blight) and broad-leaved trees (e. g. *P. ramorum*: sudden oak death); *Plasmodiophora brassicae* (club root) on cabbage, rape, radish and other plants; *Plasmopara* spp., e. g. *P. viticola* (grapevine downy mildew) on vines and *P. halstedii* on sunflowers; *Podosphaera* spp. (powdery mildew) on rosaceous plants, hop, pome and soft fruits, e. g. *P. leucotricha* on apples; *Polymyxa* spp., e. g. on cereals, such as barley and wheat (*P. graminis*) and sugar beets (*P. betae*) and thereby transmitted viral diseases; *Pseudocercosporella herpotrichoides* (eyespot, teleomorph: *Tapesia yallundae*) on cereals, e. g. wheat or barley; *Pseudoperonospora* (downy mildew) on various plants, e. g. *P. cubensis* on cucurbits or *P. humili* on hop; *Pseudopezicula tracheiphlla* (red fire disease or, rotbrenner', anamorph: *Phialophora*) on vines; *Puccinia* spp. (rusts) on various plants, e. g. *P. triticina* (brown or leaf rust), *P. striiformis* (stripe or yellow rust), *P. hordei* (dwarf rust), *P. graminis* (stem or black rust) or *P. recondita* (brown or leaf rust) on cereals, such as e. g. wheat, barley or rye, *P. kuehnii* (orange rust) on sugar cane and *P. asparagi* on asparagus; *Pyrenophora* (anamorph: *Drechslera*) *tritici-repengs* (tan spot) on wheat or *P. teres* (net blotch) on barley; *Pyricularia* spp., e. g. *P. oryzae* (teleomorph: *Magnaporthe grisea*, rice blast) on rice and *P. grisea* on turf and cereals; *Pythium* spp. (damping-off) on turf, rice, corn, wheat, cotton, rape, sunflowers, soybeans, sugar beets, vegetables and various other plants (e. g. *P. ultimum* or *P. aphanidermatum*); *Ramularia* spp., e. g. *R. collo-cygni* (Ramularia leaf spots, Physiological leaf spots) on barley and *R. beticola* on sugar beets; *Rhizoctonia* spp. on cotton, rice, potatoes, turf, corn, rape, potatoes, sugar beets, vegetables and various other plants, e. g. *R. solani* (root and stem rot) on soybeans, *R. solani* (sheath blight) on rice or *R. cereaks* (*Rhizoctonia* spring blight) on wheat or barley; *Rhizopus stolonifer* (black mold, soft rot) on strawberries, carrots, cabbage, vines and tomatoes; *Rhynchosporium secallis* (scald) on barley, rye and triticale; *Sarocladium oryzae* and *S. attenuatum* (sheath rot) on rice; *Sclerotinia* spp. (stem rot or white mold) on vegetables and field crops, such as rape, sunflowers (e. g. *S. sclerotiorum*) and soybeans (e. g. *S. rolfsii* or *S. sclerotiorum*); *Septoria* spp. on various plants, e. g. *S. glycines* (brown spot) on soybeans, *S. tritici* (*Septoria* blotch) on wheat and *S.* (syn. *Stagonospora*) *nodorum* (*Stagonospora* blotch) on cereals; *Uncinula* (syn. *Erysiphe*) *necator* (powdery mildew, anamorph: *Oidium tuckeri*) on vines; *Setospaeria* spp. (leaf blight) on corn (e. g. *S. turcicum*, syn. *Helminthosporium turcicum*) and turf; *Sphacelotheca* spp. (smut) on corn, (e. g. *S. reiliana*: head smut), sorghum and sugar cane; *Sphaerotheca fuliginea* (powdery mildew) on cucurbits; *Spongospora subterranea* (powdery scab) on potatoes and thereby transmitted viral diseases; *Stagonospora* spp. on cereals, e. g. *S. nodorum* (*Stagonospora* blotch, teleomorph: *Leptosphaeria* [syn. *Phaeosphaeria*] *nodorum*) on wheat; *Synchytrium endobioticum* on potatoes (potato wart disease); *Taphrina* spp., e. g. *T. deformans* (leaf curl disease) on peaches and *T. pruni* (plum pocket) on plums; *Thielaviopsis* spp. (black root rot) on tobacco, pome fruits, vegetables, soybeans and cotton, e. g. *T. basicola* (syn. *Chalara elegans*); *Tilletia* spp. (common bunt or stinking smut) on cereals, such as e. g. *T. tritici* (syn. *T. caries*, wheat bunt) and *T. controversa* (dwarf bunt) on wheat; *Typhula incarnata* (grey snow mold) on barley or wheat; *Urocysgs* spp., e. g. *U. occulta* (stem smut) on rye; *Uromyces* spp. (rust) on vegetables, such as beans (e. g. *U. appencliculatus*, syn. *U. phaseoli*) and sugar beets (e. g. *U. betae*); *Ustilago* spp. (loose smut) on cereals (e. g. *U. nuda* and *U. avaenae*), corn (e. g. *U. maydis*: corn smut) and sugar cane; *Venturia* spp. (scab) on apples (e. g. *V. inaequalis*) and pears; and *Verticillium* spp. (wilt) on various plants, such as fruits and ornamentals, vines, soft fruits, vegetables and field crops, e. g. *V. dahliae* on strawberries, rape, potatoes and tomatoes. In a preferred embodiment the compounds I and compositions thereof, respectively, are particularly suitable for controlling the following plant diseases: *Puccinia* spp. (rusts) on various plants, for example, but not limited to *P. triticina* (brown or leaf rust), *P. striiformis* (stripe or yellow rust), *P. hordei* (dwarf rust), *P. graminis* (stem or black rust) or *P. recondita* (brown or leaf rust) on cereals, such as e. g. wheat, barley or rye and *Phakopsoraceae* spp. on various plants, in particular *Phakopsora pachyrhizi* and *P. meibomiae* (soybean rust) on soybeans.

The compounds I and compositions thereof, respectively, are also suitable for controlling harmful fungi in the protection of stored products or harvest and in the protection of materials. The term "protection of materials" is to be understood to denote the protection of technical and non-living materials, such as adhesives, glues, wood, paper and paperboard, textiles, leather, paint dispersions, plastics, cooling lubricants, fiber or fabrics, against the infestation and destruction by harmful microorganisms, such as fungi and bacteria. As to the protection of wood and other materials, the particular attention is paid to the following harmful fungi: *Ascomycetes* such as *Ophiostoma* spp., *Ceratocysgs* spp., *Aureobasidium pullulans, Scierophoma* spp., *Chaetomium* spp., *Humicola* spp., *Petriella* spp., *Trichurus* spp.; *Basidiomycetes* such as *Coniophora* spp., *Coriolus* spp., *Gloeophyllum* spp., *Lentinus* spp., *Pleurotus* spp., *Poria* spp., *Serpula* spp. and *Tyromyces* spp., *Deuteromycetes* such as *Aspergillus* spp., *Cladosporium* spp., *Penicillium* spp., *Trichoderma* spp., *Alternaria* spp., *Paecllomyces* spp. and *Zygomycetes* such as *Mucor* spp., and in addition in the protection of stored products and harvest the following yeast fungi are worthy of note: *Candida* spp. and *Saccharomyces cerevisae*. The method of treatment according to the invention can also be used in the field of protecting stored products or harvest against attack of fungi and microorganisms. According to the present invention, the term "stored products" is understood to denote natural substances of plant or animal origin and their processed forms, which have been taken from the natural life cycle and for which long-term protection is desired. Stored products of crop plant origin, such as plants or parts thereof, for example stalks, leafs, tubers, seeds, fruits or grains, can be protected in the freshly harvested state or in processed form, such as pre-dried, moistened, comminuted, ground, pressed or roasted, which process is also known as post-harvest treatment. Also falling under the definition of stored products is timber, whether in the form of crude timber, such as construction timber, electricity pylons and barriers, or in the form of finished articles, such as furniture or objects made from wood. Stored products of animal origin are hides, leather, furs, hairs and the like. The combinations according the present invention can prevent disadvantageous effects such as decay, discoloration or mold. Preferably "stored products" is understood to denote natural substances of plant origin and their processed forms, more preferably fruits and their processed forms, such as pomes, stone fruits, soft fruits and citrus fruits and their processed forms.

The compounds of formula I can be present in different crystal modifications whose biological activity may differ. They are likewise subject matter of the present invention.

The compounds I are employed as such or in form of compositions by treating the fungi or the plants, plant propagation materials, such as seeds, soil, surfaces, materials or rooms to be protected from fungal attack with a fungicidally effective amount of the active substances. The application can be carried out both before and after the infection of the plants, plant propagation materials, such as seeds, soil, surfaces, materials or rooms by the fungi.

Plant propagation materials may be treated with compounds I as such or a composition comprising at least one compound I prophylactically either at or before planting or transplanting. The invention also relates to agrochemical compositions comprising an auxiliary and at least one compound I according to the invention.

An agrochemical composition comprises a fungicidally effective amount of a compound I. The term "effective amount" denotes an amount of the composition or of the compounds I, which is sufficient for controlling harmful fungi on cultivated plants or in the protection of materials and which does not result in a substantial damage to the treated plants. Such an amount can vary in a broad range and is dependent on various factors, such as the fungal species to be controlled, the treated cultivated plant or material, the climatic conditions and the specific compound I used.

The compounds I, their N-oxides and salts can be converted into customary types of agrochemical compositions, e. g. solutions, emulsions, suspensions, dusts, powders, pastes, granules, pressings, capsules, and mixtures thereof. Examples for composition types are suspensions (e. g. SC, OD, FS), emulsifiable concentrates (e. g. EC), emulsions (e. g. EW, EO, ES, ME), capsules (e. g. CS, ZC), pastes, pastilles, wettable powders or dusts (e. g. WP, SP, WS, DP, DS), pressings (e. g. BR, TB, DT), granules (e. g. WG, SG, GR, FG, GG, MG), insecticidal articles (e. g. LN), as well as gel formulations for the treatment of plant propagation materials such as seeds (e. g. GF). These and further compositions types are defined in the "Catalogue of pesticide formulation types and international coding system", Technical Monograph No. 2, 6th Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e. g. kerosene, diesel oil; oils of vegetable or animal origin; aliphatic, cyclic and aromatic hydrocarbons, e. g. toluene, paraffin, tetrahydronaphthalene, alkylated naphthalenes; alcohols, e. g. ethanol, propanol, butanol, benzyl alcohol, cyclohexanol; glycols; DMSO; ketones, e. g. cyclohexanone; esters, e. g. lactates, carbonates, fatty acid esters, gamma-butyrolactone; fatty acids; phosphonates; amines; amides, e. g. N-methyl pyrrolidone, fatty acid dimethyl amides; and mixtures thereof. Suitable solid carriers or fillers are mineral earths, e. g. silicates, silica gels, talc, kaolins, limestone, lime, chalk, clays, dolomite, diatomaceous earth, bentonite, calcium sulfate, magnesium sulfate, magnesium oxide; polysaccharides, e. g. cellulose, starch; fertilizers, e. g. ammonium sulfate, ammonium phosphate, ammonium nitrate, ureas; products of vegetable origin, e. g. cereal meal, tree bark meal, wood meal, nutshell meal, and mixtures thereof. Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylaryl sulfonates, diphenyl sulfonates, alpha-olefin sulfonates, lignin sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkyl naphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinyl pyrrolidone, vinyl alcohols, or vinyl acetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinyl amines or polyethylene amines.

Suitable adjuvants are compounds, which have a negligible or even no pesticidal activity themselves, and which improve the biological performance of the compound I on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e. g. xanthan gum, carboxymethyl cellulose), inorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e. g. in red, blue, or green) are pigments of low water solubility and water-soluble dyes. Examples are inorganic colorants (e. g. iron oxide, titan oxide, iron hexacyanoferrate) and organic colorants (e. g. alizarin-, azo- and phthalocyanine colorants).

Suitable tackifiers or binders are polyvinyl pyrrolidones, polyvinyl acetates, polyvinyl alcohols, polyacrylates, biological or synthetic waxes, and cellulose ethers.

Examples for composition types and their preparation are:

i) Water-Soluble Concentrates (SL, LS)

10-60 wt % of a compound I and 5-15 wt % wetting agent (e. g. alcohol alkoxylates) are dissolved in water and/or in a water-soluble solvent (e. g. alcohols) ad 100 wt %. The active substance dissolves upon dilution with water.

ii) Dispersible Concentrates (DC)

5-25 wt % of a compound I and 1-10 wt % dispersant (e. g. polyvinyl pyrrolidone) are dissolved in organic solvent (e. g. cyclohexanone) ad 100 wt %. Dilution with water gives a dispersion.

iii) Emulsifiable Concentrates (EC)

15-70 wt % of a compound I and 5-10 wt % emulsifiers (e. g. calcium dodecylbenzenesulfonate and castor oil ethoxylate) are dissolved in water-insoluble organic solvent (e. g. aromatic hydrocarbon) ad 100 wt %. Dilution with water gives an emulsion.

iv) Emulsions (EW, EO, ES)

5-40 wt % of a compound I and 1-10 wt % emulsifiers (e. g. calcium dodecylbenzenesulfonate and castor oil ethoxylate) are dissolved in 20-40 wt % water-insoluble organic solvent (e. g. aromatic hydrocarbon). This mixture is introduced into water ad 100 wt % by means of an emulsifying machine and made into a homogeneous emulsion. Dilution with water gives an emulsion.

v) Suspensions (SC, OD, FS)

In an agitated ball mill, 20-60 wt % of a compound I are comminuted with addition of 2-10 wt % dispersants and wetting agents (e. g. sodium lignosulfonate and alcohol ethoxylate), 0.1-2 wt % thickener (e. g. xanthan gum) and water ad 100 wt % to give a fine active substance suspension. Dilution with water gives a stable suspension of the active substance. For FS type composition up to 40 wt % binder (e. g. polyvinyl alcohol) is added.

vi) Water-Dispersible Granules and Water-Soluble Granules (WG, SG)

50-80 wt % of a compound I are ground finely with addition of dispersants and wetting agents (e. g. sodium lignosulfonate and alcohol ethoxylate) ad 100 wt % and prepared as water-dispersible or water-soluble granules by means of technical appliances (e. g. extrusion, spray tower, fluidized bed). Dilution with water gives a stable dispersion or solution of the active substance.

vii) Water-Dispersible Powders and Water-Soluble Powders (WP, SP, WS)

50-80 wt % of a compound I are ground in a rotor-stator mill with addition of 1-5 wt % dispersants (e. g. sodium lignosulfonate), 1-3 wt % wetting agents (e. g. alcohol ethoxylate) and solid carrier (e. g. silica gel) ad 100 wt %. Dilution with water gives a stable dispersion or solution of the active substance.

viii) Gel (GW, GF)

In an agitated ball mill, 5-25 wt % of a compound I are comminuted with addition of 3-10 wt % dispersants (e. g. sodium lignosulfonate), 1-5 wt % thickener (e. g. carboxymethyl cellulose) and water ad 100 wt % to give a fine suspension of the active substance. Dilution with water gives a stable suspension of the active substance.

ix) Microemulsion (ME)

5-20 wt % of a compound I are added to 5-30 wt % organic solvent blend (e. g. fatty acid dimethyl amide and cyclohexanone), 10-25 wt % surfactant blend (e. g. alcohol ethoxylate and arylphenol ethoxylate), and water ad 100%. This mixture is stirred for 1 h to produce spontaneously a thermodynamically stable microemulsion.

x) Microcapsules (CS)

An oil phase comprising 5-50 wt % of a compound I, 0-40 wt % water insoluble organic solvent (e. g. aromatic hydrocarbon), 2-15 wt % acrylic monomers (e. g. methylmethacrylate, methacrylic acid and a di- or triacrylate) are dispersed into an aqueous solution of a protective colloid (e. g. polyvinyl alcohol). Radical polymerization results in the formation of poly(meth)acrylate microcapsules. Alternatively, an oil phase comprising 5-50 wt % of a compound I according to the invention, 0-40 wt % water insoluble organic solvent (e. g. aromatic hydrocarbon), and an isocyanate monomer (e. g. diphenylmethene-4,4'-diisocyanatae) are dispersed into an aqueous solution of a protective colloid (e. g. polyvinyl alcohol). The addition of a polyamine (e. g. hexamethylenediamine) results in the formation of polyurea microcapsules. The monomers amount to 1-10 wt %. The wt % relate to the total CS composition.

xi) Dustable Powders (DP, DS)

1-10 wt % of a compound I are ground finely and mixed intimately with solid carrier (e. g. finely divided kaolin) ad 100 wt %.

xii) Granules (GR, FG)

0.5-30 wt % of a compound I is ground finely and associated with solid carrier (e. g. silicate) ad 100 wt %. Granulation is achieved by extrusion, spray-drying or fluidized bed.

xiii) Ultra-Low Volume Liquids (UL)

1-50 wt % of a compound I are dissolved in organic solvent (e. g. aromatic hydrocarbon) ad 100 wt %.

The compositions types i) to xiii) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions generally comprise between 0.01 and 95%, preferably between 0.1 and 90%, more preferably between 1 and 70%, and in particular between 10 and 60%, by weight of active substance. The active substances are employed in a purity of from 90% to 100%, preferably from 95% to 100% (according to NMR spectrum).

For the purposes of treatment of plant propagation materials, particularly seeds, solutions for seed treatment (LS), Suspoemulsions (SE), flowable concentrates (FS), powders for dry treatment (DS), water-dispersible powders for slurry treatment (WS), water-soluble powders (SS), emulsions (ES), emulsifiable concentrates (EC), and gels (GF) are usually employed. The compositions in question give, after two-to-tenfold dilution, active substance concentrations of from 0.01 to 60% by weight, preferably from 0.1 to 40%, in the ready-to-use preparations. Application can be carried out before or during sowing. Methods for applying compound I and compositions thereof, respectively, onto plant propagation material, especially seeds, include dressing, coating, pelleting, dusting, and soaking as well as in-furrow application methods. Preferably, compound I or the compositions thereof, respectively, are applied on to the plant propagation material by a method such that germination is not induced, e. g. by seed dressing, pelleting, coating and dusting.

When employed in plant protection, the amounts of active substances applied are, depending on the kind of effect desired, from 0.001 to 2 kg per ha, preferably from 0.005 to 2 kg per ha, more preferably from 0.05 to 0.9 kg per ha, and in particular from 0.1 to 0.75 kg per ha. In treatment of plant propagation materials such as seeds, e. g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seeds) are generally required.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetters, adjuvants, fertilizer, or micronutrients, and further pesticides (e. g. herbicides, insecticides, fungicides, growth regulators, safeners, biopesticides) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

A pesticide is generally a chemical or biological agent (such as pestidal active ingredient, compound, composition, virus, bacterium, antimicrobial or disinfectant) that through its effect deters, incapacitates, kills or otherwise discourages pests. Target pests can include insects, plant pathogens, weeds, mollusks, birds, mammals, fish, nematodes (roundworms), and microbes that destroy property, cause nuisance, spread disease or are vectors for disease. The term "pesticide" includes also plant growth regulators that alter the expected growth, flowering, or reproduction rate of plants; defoliants that cause leaves or other foliage to drop from a plant, usually to facilitate harvest; desiccants that promote drying of living tissues, such as unwanted plant tops; plant activators that activate plant physiology for defense of against certain pests; safeners that reduce unwanted herbicidal action of pesticides on crop plants; and plant growth promoters that affect plant physiology e.g. to increase plant growth, biomass, yield or any other quality parameter of the harvestable goods of a crop plant.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of a binary or ternary mixture may be mixed by the user himself in a spray tank or any other kind of vessel used for applications (e. g. seed treater drums, seed pelleting machinery, knapsack sprayer) and further auxiliaries may be added, if appropriate.

Consequently, one embodiment of the invention is a kit for preparing a usable pesticidal composition, the kit comprising a) a composition comprising component 1) as defined herein and at least one auxiliary; and b) a composition comprising component 2) as defined herein and at least one auxiliary; and optionally c) a composition comprising at least one auxiliary and optionally a further active component 3) as defined herein.

Mixing the compounds I or the compositions comprising them in the use form as fungicides with other fungicides results in many cases in an expansion of the fungicidal spectrum of activity being obtained or in a prevention of fungicide resistance development. Furthermore, in many cases, synergistic effects are obtained.

The following list of pesticides II (e. g. pesticidally-active substances and biopesticides), in conjunction with which the compounds I can be used, is intended to illustrate the possible combinations but does not limit them:

A) Respiration inhibitors: Inhibitors of complex III at $Q_o$ site: azoxystrobin (A.1.1), coumeth-oxystrobin (A.1.2), coumoxystrobin (A.1.3), dimoxystrobin (A.1.4), enestroburin (A.1.5), fenaminstrobin (A.1.6), fenoxystrobin/flufenoxystrobin (A.1.7), fluoxastrobin (A.1.8), kresoxim-methyl (A.1.9), mandestrobin (A.1.10), metominostrobin (A.1.11), orysastrobin (A.1.12), picoxy-strobin (A.1.13), pyraclostrobin (A.1.14), pyrametostrobin (A.1.15), pyraoxystrobin (A.1.16), trifloxystrobin (A.1.17), 2-(2-(3-(2,6-dichlorophenyl)-1-methyl-allylideneaminooxymethyl)-phenyl)-2-methoxyimino-N-methyl-acetamide (A.1.18), pyribencarb (A.1.19), triclopyricarb/chlorodincarb (A.1.20), famoxadone (A.1.21), fenamidone (A.1.21), methyl-N-[2-[(1,4-dimethyl-5-phenyl-pyrazol-3-yl)oxy]methyl]phenyl]-N-methoxy-carbamate (A.1.22), 1-[3-chloro-2-[[1-(4-chlorophenyl)-1H-pyrazol-3-yl]oxymethyl]phenyl]-4-methyl-tetrazol-5-one (A.1.23), 1-[3-bromo-2-[[1-(4-chlorophenyl)pyrazol-3-yl]oxymethyl]phenyl]-4-methyl-tetrazol-5-one (A.1.24), 1-[2-[[1-(4-chlorophenyl)pyrazol-3-yl]oxymethyl]-3-methyl-phenyl]-4-methyl-tetra-zol-5-one (A.1.25), 1-[2-[[1-(4-chlorophenyl)pyrazol-3-yl]oxymethyl]-3-fluoro-phenyl]-4-methyl-tetrazol-5-one (A.1.26), 1-[2-[[1-(2,4-dichlorophenyl)pyrazol-3-yl]oxymethyl]-3-fluoro-phenyl]-4-methyl-tetrazol-5-one (A.1.27), 1-[2-[[4-(4-chlorophenyl)thiazol-2-yl]oxymethyl]-3-methyl-phenyl]-4-methyl-tetrazol-5-one (A.1.28), 1-[3-chloro-2-[[4-(p-tolylthiazol-2-yl]oxymethyl]phenyl]-4-methyl-tetrazol-5-one (A.1.29), 1-[3-cyclopropyl-2-[[2-methyl-4-(1-methylpyrazol-3-yl)phenoxy]-methyl]phenyl]-4-methyl-tetrazol-5-one (A.1.30), 1-[3-(difluoromethoxy)-2-[[2-methyl-4-(1-methylpyrazol-3-yl)phenoxy]methyl]phenyl]-4-methyl-tetrazol-5-one (A.1.31), 1-methyl-4-[3-methyl-2-[[2-methyl-4-(1-methylpyrazol-3-yl)phenoxy]methyl]phenyl]tetrazol-5-one (A.1.32), 1-methyl-4-[3-methyl-2-[[1-[3-(trifluoromethyl)phenyl]-ethylideneamino]oxymethyl]phenyl]tetrazol-5-one (A.1.33), (Z,2E)-5-[1-(2,4-dichlorophenyl)pyrazol-3-yl]-oxy-2-methoxyimino-N,3-dimethyl-pent-3-enamide (A.1.34), (Z,2E)-5-[1-(4-chlorophenyl)pyrazol-3-yl]oxy-2-methoxyimino-N,3-dimethyl-pent-3-enamide (A.1.35), pyriminostrobin (A.1.36), bifujunzhi (A.1.37), 2-(ortho-((2,5-dimethylphenyl-oxymethylen)phenyl)-3-methoxy-acrylic acid methylester (A.1.38).

Inhibitors of complex III at $Q_i$ site: cyazofamid (A.2.1), amisulbrom (A.2.2), [(6S,7R,8R)-8-benzyl-3-[(3-hydroxy-4-methoxy-pyridine-2-carbonyl)amino]-6-methyl-4,9-dioxo-1,5-dioxonan-7-yl] 2-methylpropanoate (A.2.3), [2-[[(7R,8R,9S)-7-benzyl-9-methyl-8-(2-methylpropanoyloxy)-2,6-dioxo-1,5-dioxonan-3-yl]carbamoyl]-4-methoxy-3-pyridyl]oxymethyl 2-methylpropanoate (A.2.4), [(6S,7R,8R)-8-benzyl-3-[[4-methoxy-3-(propanoyloxy-methoxy)pyridine-2-carbonyl]amino]-6-methyl-4,9-dioxo-1,5-dioxonan-7-yl] 2-methylpropanoate (A.2.5).

Inhibitors of complex II: benodanil (A.3.1), benzovindiflupyr (A.3.2), bixafen (A.3.3), boscalid (A.3.4), carboxin (A.3.5), fenfuram (A.3.6), fluopyram (A.3.7), flutolanil (A.3.8), fluxapyroxad (A.3.9), furametpyr (A.3.10), isofetamid (A.3.11), isopyrazam (A.3.12), mepronil (A.3.13), oxycarboxin (A.3.14), penflufen (A.3.15), penthiopyrad (A.3.16), 3-(difluoromethyl)-N-methoxy-1-methyl-N-[1-methyl-2-(2,4,6-trichlorophenypethyl]pyrazole-4-carboxamide (A.3.17), N-[2-(3,4-difluorophenyl)phenyl]-3-(trifluoromethyl)pyrazine-2-carboxamide (A.3.18), sedaxane (A.3.19), tecloftalam (A.3.20), thifluzamide (A.3.21), 3-(difluoromethyl)-1-methyl-N-(1,1,3-trimethylindan-4-yl)pyrazole-4-carboxamide (A.3.22), 3-(trifluoromethyl)-1-methyl-N-(1,1,3-trimethylindan-4-yl)pyrazole-4-carboxamide (A.3.23), 1,3-dimethyl-N-(1,1,3-trimethylindan-4-yl)pyrazole-4-carboxamide (A.3.24), 3-(trifluoromethyl)-1,5-dimethyl-N-(1,1,3-trimethylindan-4-yl)pyrazole-4-carboxamide (A.3.25), 1,3,5-trimethyl-N-(1,1,3-trimethylindan-4-yl)pyrazole-4-carboxamide (A.3.26), 3-(difluoromethyl)-1,5-dimethyl-N-(1,1,3-trimethylindan-4-yl)pyrazole-4-carboxamide (A.3.27), 3-(difluoromethyl)-N-(7-fluoro-1,1,3-trimethyl-indan-4-yl)-1-methyl-pyrazole-4-carboxamide (A.3.28), methyl (E)-2-[2-[(5-cyano-2-methyl-phenoxy)methyl]phenyl]-3-methoxy-prop-2-enoate (A.3.30), N-[(5-chloro-2-isopropyl-phenyl)methyl]-N-cyclopropyl-3-(difluoromethyl)-5 fluoro-1-methyl-pyrazole-4-carboxamide (A.3.31), 2-(difluoromethyl)-N-(1,1,3-trimethyl-indan-4-yl)pyridine-3-carboxamide (A.3.32), 2-(difluoromethyl)-N-[(3R)-1,1,3-trimethylindan-4-yl]pyridine-3-carboxamide (A.3.33), 2-(difluoromethyl)-N-(3-ethyl-1,1-dimethyl-indan-4-yl)¬pyridine-3-carboxamide (A.3.34), 2-(difluoromethyl)-N-[(3R)-3-ethyl-1,1-dimethyl-indan-4-yl]¬pyridine-3-carboxamide (A.3.35), 2-(difluoromethyl)-N-(1,1-dimethyl-3-propyl-indan-4-yl)¬py¬iridine-3-carboxamide (A.3.36), 2-(difluoromethyl)-N-[(3R)-1,1-dimethyl-3-propyl-indan-4-yl]¬pyridine-3-carboxamide (A.3.37), 2-(difluoromethyl)-N-(3-isobutyl-1,1-dimethyl-indan-4-yl)¬pyridine-3-carboxamide (A.3.38), 2-(difluoromethyl)-N-[(3R)-3-isobutyl-1,1-dimethyl-indan-4 yl]pyridine-3-carboxamide (A.3.39).

Other respiration inhibitors: diflumetorim (A.4.1); nitrophenyl derivates: binapacryl (A.4.2), dinobuton (A.4.3), dinocap (A.4.4), fluazinam (A.4.5), meptyldinocap (A.4.6), ferimzone (A.4.7); organometal compounds: fentin salts, e. g. fentin-acetate (A.4.8), fentin chloride (A.4.9) or fentin hydroxide (A.4.10); ametoctradin (A.4.11); silthiofam (A.4.12).

B) Sterol biosynthesis inhibitors (SBI fungicides)

C14 demethylase inhibitors: triazoles: azaconazole (B.1.1), bitertanol (B.1.2), bromuconazole (B.1.3), cyproconazole (B.1.4), difenoconazole (B.1.5), diniconazole (B.1.6), diniconazole-M (B.1.7), epoxiconazole (B.1.8), fenbuconazole (B.1.9), fluquinconazole (B.1.10), flusilazole (B.1.11), flutriafol (B.1.12), hexaconazole (B.1.13), imibenconazole (B.1.14), ipconazole (B.1.15), metconazole (B.1.17), myclobutanil (B.1.18), oxpoconazole (B.1.19), paclobutrazole (B.1.20), penconazole (B.1.21), propiconazole (B.1.22), prothioconazole (B.1.23), simeconazole (B.1.24), tebuconazole (B.1.25), tetraconazole (B.1.26), triadimefon (B.1.27), triadimenol (B.1.28), triticonazole (B.1.29), uniconazole (B.1.30), 1-[rel-(2S;3R)-3-(2-chlorophenyl)-2-(2,4-difluorophenyl)-oxiranylmethyl]-5-thiocyanato-1H-[1,2,4]triazole (B.1.31), 2-[rel-(2S,3R)-3-(2-chlorophenyl)-2-(2,4-difluorophenyl)-oxiranylmethyl]-2H-[1,2,4]triazole-3-thiol (B.1.32), 2-[2-chloro-4-(4-chlorophenoxy)phenyl]-1-(1,2,4-triazol-1-yl)pentan-2-ol (B.1.33), 1-[4-(4-chlorophenoxy)-2-(trifluoromethyl)phenyl]-1-cyclopropyl-2-(1,2,4-triazol-1-yl)ethanol (B.1.34), 2-[4-(4-chlorophenoxy)-2-(trifluoromethyl)phenyl]-1-(1,2,4-triazol-1-yl)butan-2-ol (B.1.35), 2-[2-chloro-4-(4-chlorophenoxy)phenyl]-1-(1,2,4-triazol-1-yl)butan-2-ol (B.1.36), 2-[4-(4-chloro-phenoxy)-2-(trifluoromethyl)phenyl]-3-methyl-1-(1,2,4-triazol-1-yl)butan-2-ol (B.1.37), 2-[4-(4-chlorophenoxy)-2-(trifluoromethyl)phenyl]-1-(1,2,4-triazol-1-yl)propan-2-ol (B.1.38), 2-[2-chloro-4-(4-chlorophenoxy)phenyl]-3-methyl-1-(1,2,4-triazol-1-yl)butan-2-ol (B.1.39), 2-[4-(4-chlorophenoxy)-2-(trifluoromethyl)phenyl]-1-(1,2,4-triazol-1-yl)pentan-2-ol (B.1.40), 2-[4-(4-fluorophenoxy)-2-(trifluoromethyl)phenyl]-1-(1,2,4-triazol-1-yl)propan-2-ol (B.1.41), 2-[2-chloro-4-(4-chlorophenoxy)phenyl]-1-(1,2,4-triazol-1-yl)pent-3-yn-2-ol (B.1.42), 2-(chloromethyl)-2-methyl-5-(p-tolylmethyl)-1-(1,2,4-triazol-1-ylmethyl)cyclopentanol (B.1.43); imidazoles: imazalil (B.1.44), pefurazoate (B.1.45), prochloraz (B.1.46), triflumizol (B.1.47); pyrimidines, pyridines and piperazines: fenarimol (B.1.49), pyrifenox (B.1.50), triforine (B.1.51), [3-(4-chloro-2-fluorophenyl)-5-(2,4-difluorophenypisoxazol-4-yl]-(3-pyridyl)methanol (B.1.52).

Delta14-reductase inhibitors: aldimorph (B.2.1), dodemorph (B.2.2), dodemorph-acetate (B.2.3), fenpropimorph (B.2.4), tridemorph (B.2.5), fenpropidin (B.2.6), piperalin (B.2.7), spiroxamine (B.2.8).

Inhibitors of 3-keto reductase: fenhexamid (B.3.1).

Other Sterol biosynthesis inhibitors: chlorphenomizole (B.4.1).

C) Nucleic acid synthesis inhibitors

Phenylamides or acyl amino acid fungicides: benalaxyl (C.1.1), benalaxyl-M (C.1.2), kiralaxyl (C.1.3), metalaxyl (C.1.4), metalaxyl-M (C.1.5), ofurace (C.1.6), oxadixyl (C.1.7). Other nucleic acid synthesis inhibitors: hymexazole (C.2.1), octhilinone (C.2.2), oxolinic acid (C.2.3), bupirimate (C.2.4), 5-fluorocytosine (C.2.5), 5-fluoro-2-(p-tolylmethoxy)pyrimidin-4-amine (C.2.6), 5-fluoro-2-(4-fluorophenylmethoxy)pyrimidin-4-amine (C.2.7), 5-fluoro-2-(4-chlorophenylmethoxy)pyrimidin-4 amine (C.2.8).

D) Inhibitors of cell division and cytoskeleton

Tubulin inhibitors: benomyl (D.1.1), carbendazim (D.1.2), fuberidazole (D1.3), thiabendazole (D.1.4), thiophanate-methyl (D.1.5), 3-chloro-4-(2,6-difluorophenyl)-6-methyl-5-phenyl-pyridazine (D.1.6), 3-chloro-6-methyl-5-phenyl-4-(2,4,6-trifluorophenyl)pyridazine (D.1.7), N-ethyl-2-[(3-ethynyl-8-methyl-6-q uinolyl)oxy]butanamide (D.1.8), N-ethyl-2-[(3-ethynyl-8-methyl-6-q uinolyl)oxy]-2-methylsulfanyl-acetamide (D.1.9), 2-[(3-ethynyl-8-methyl-6-quinolyl)oxy]-N-(2-fluoroethyl)butanamide (D.1.10), 2-[(3-ethynyl-8-methyl-6-quinolyl)oxy]-N-(2-fluoroethyl)-2-methoxy-acetamide (D.1.11), 2-[(3-ethynyl-8-methyl-6-quinolyl)oxy]-N-propyl-butanamide (D.1.12), 2-[(3-ethynyl-8-methyl-6-quinolyl)oxy]-2-methoxy-N-propyl-acetamide (D.1.13), 2-[(3-ethynyl-8-methyl-6-quinolyl)oxy]-2-methylsulfanyl-N-propyl-acetamide (D.1.14), 2-[(3-ethynyl-8-methyl-6-qui nolyl)oxy]-N-(2-fluoroethyl)-2-methylsulfanyl-acetamide (D.1.15), 4-(2-bromo-4-fluorophenyl)-N-(2-chloro-6-fluoro-phenyl)-2,5-dimethyl-pyrazol-3-amine (D.1.16). Other cell division inhibitors: diethofencarb (D.2.1), ethaboxam (D.2.2), pencycuron (D.2.3), fluopicolide (D.2.4), zoxamide (D.2.5), metrafenone (D.2.6), pyriofenone (D.2.7).

E) Inhibitors of amino acid and protein synthesis

Methionine synthesis inhibitors: cyprodinil (E.1.1), mepanipyrim (E.1.2), pyrimethanil (E.1.3). Protein synthesis inhibitors: blasticidin-S (E.2.1), kasugamycin (E.2.2), kasugamycin hydrochloride-hydrate (E.2.3), mildiomycin (E.2.4), streptomycin (E.2.5), oxytetracyclin (E.2.6).

F) Signal transduction inhibitors

MAP/histidine kinase inhibitors: fluoroimid (F.1.1), iprodione (F.1.2), procymidone (F.1.3), vinclozolin (F.1.4), fludioxonil (F.1.5).

G protein inhibitors: quinoxyfen (F.2.1).

G) Lipid and membrane synthesis inhibitors

Phospholipid biosynthesis inhibitors: edifenphos (G.1.1), iprobenfos (G.1.2), pyrazophos (G.1.3), isoprothiolane (G.1.4).

Lipid peroxidation: dicloran (G.2.1), quintozene (G.2.2), tecnazene (G.2.3), tolclofos-methyl (G.2.4), biphenyl (G.2.5), chloroneb (G.2.6), etridiazole (G.2.7).

Phospholipid biosynthesis and cell wall deposition: dimethomorph (G.3.1), flumorph (G.3.2), mandipropamid (G.3.3), pyrimorph (G.3.4), benthiavalicarb (G.3.5), iprovalicarb (G.3.6), valifenalate (G.3.7).

Compounds affecting cell membrane permeability and fatty acides: propamocarb (G.4.1). Inhibitors of oxysterol binding protein: oxathiapiprolin (G.5.1), 2-{3-[2-(1-{[3,5-bis(difluoromethyl-1H-pyrazol-1-yl]acetyl}piperidin-4-yl)-1,3-thiazol-4-yl]-4,5-dihydro-1,2-oxazol-5-yl}phenyl methanesulfonate (G.5.2), 2-{3-[2-(1-{[3,5-bis(difluoromethyl)-1H-pyrazol-1-yl]acetyl}piperidin-4-yl) 1,3-thiazol-4-yl]-4,5-dihydro-1,2-oxazol-5-yl}-3-chlorophenyl methanesulfonate (G.5.3), 4-[1-[2-[3-(difluoromethyl)-5-methyl-pyrazol-1-yl]acetyl]-4-piperidyl]-N-tetralin-1-yl-pyridine-2-carboxamide (G.5.4), 4-[1-[2-[3,5-bis(difluoromethyl)pyrazol-1-yl]acetyl]-4-piperidyl]-N-tetralin-1-yl-pyridine-2-carboxamide (G.5.5), 4-[1-[2-[3-(difluoromethyl)-5-(trifluoromethyl)pyrazol-1-yl]acetyl]-4-piperidyl]-N-tetralin-1-yl-pyridine-2-carboxamide (G.5.6), 4-[1-[2-[5-cyclopropyl-3-(difluoromethyl)pyrazol-1-yl]acetyl]-4-piperidyl]-N-tetralin-1-yl-pyridine-2-carboxamide (G.5.7), 4-[1-[2-[5-methyl-3-(trifluoromethyl)pyrazol-1-yl]acetyl]-4-piperidyl]-N-tetralin-1-yl-pyridine-2-carboxamide (G.5.8), 4-[1-[2-[5-(difluoromethyl)-3-(trifluoromethyppyrazol-1-yl]acetyl]-4-piperidyl]-N-tetralin-1-yl-pyridine-2-carboxamide (G.5.9), 4-[1-[2-[3,5-bis(trifluoromethyl)pyrazol-1-yl]acetyl]-4-piperidyl]-N-tetralin-1-yl-pyridine-2-carboxamide (G.5.10), (4-[1-[2-[5-cyclopropyl-3-(trifluoromethyppyrazol-1-yl]acetyl]-4-piperidyl]-N-tetralin-1-yl-pyridine-2-carboxamide (G.5.11).

H) Inhibitors with Multi Site Action

Inorganic active substances: Bordeaux mixture (H.1.1), copper (H.1.2), copper acetate (H.1.3), copper hydroxide (H.1.4), copper oxychloride (H.1.5), basic copper sulfate (H.1.6), sulfur (H.1.7).

Thio- and dithiocarbamates: ferbam (H.2.1), mancozeb (H.2.2), maneb (H.2.3), metam (H.2.4), metiram (H.2.5), propineb (H.2.6), thiram (H.2.7), zineb (H.2.8), ziram (H.2.9). Organochlorine compounds: anilazine (H.3.1), chlorothalonil (H.3.2), captafol (H.3.3), captan (H.3.4), folpet (H.3.5), dichlofluanid (H.3.6), dichlorophen (H.3.7), hexachlorobenzene (H.3.8), pentachlorphenole (H.3.9) and its salts, phthalide (H.3.10), tolylfluanid (H.3.11). Guanidines and others: guanidine (H.4.1), dodine (H.4.2), dodine free base (H.4.3), guazatine (H.4.4), guazatine-acetate (H.4.5), iminoctadine (H.4.6), iminoctadine-triacetate (H.4.7), iminoctadine-tris(albesilate) (H.4.8), dithianon (H.4.9), 2,6-dimethyl-1H,5H-[1,4]dithiino[2,3-c:5,6-c'] dipyrrole-1,3,5,7(2H,6H)-tetraone (H.4.10).

I) Cell wall synthesis inhibitors

Inhibitors of glucan synthesis: validamycin (I.1.1), polyoxin B (I.1.2).

Melanin synthesis inhibitors: pyroquilon (I.2.1), tricyclazole (I.2.2), carpropamid (I.2.3), dicyclomet (I.2.4), fenoxanil (I.2.5).

J) Plant defence inducers

Acibenzolar-S-methyl (J.1.1), probenazole (J.1.2), isotianil (J.1.3), tiadinil (J.1.4), prohexadione-calcium (J.1.5); phosphonates: fosetyl (J.1.6), fosetyl-aluminum (J.1.7), phosphorous acid and its salts (J.1.8), potassium or sodium bicarbonate (J.1.9), 4-cyclopropyl-N-(2,4-dimethoxyphenyl)thiadiazole-5-carboxamide (J.1.10).

K) Unknown mode of action

Bronopol (K.1.1), chinomethionat (K.1.2), cyflufenamid (K.1.3), cymoxanil (K.1.4), dazomet (K.1.5), debacarb (K.1.6), diclocymet (K.1.7), diclomezine (K.1.8), difenzoquat (K.1.9), di-fenzoquat-methylsulfate (K.1.10), diphenylamin (K.1.11), fenitropan (K.1.12), fenpyrazamine (K.1.13), flumetover (K.1.14), flusulfamide (K.1.15), flutianil (K.1.16), harpin (K.1.17), metha-sulfocarb (K.1.18), nitrapyrin (K.1.19), nitrothal-isopropyl (K.1.20), tolprocarb (K.1.21), oxin-copper (K.1.22), proquinazid (K.1.23), tebufloquin (K.1.24), tecloftalam (K.1.25), triazoxide (K.1.26), N'-(4-(4-chloro-3-trifluoromethyl-phenoxy)-2,5-dimethyl-phenyl)-N-ethyl-N-methyl formamidine (K.1.27), N'-(4-(4-fluoro-3-trifluoromethyl-phenoxy)-2,5-dimethyl-phenyl)-N-ethyl-N-methyl formamidine (K.1.28), N'-[4-[[3-[(4-chlorophenyhmethyl]-1,2,4-thiadiazol-5-yl]oxy]-2,5-dimethyl-phenyl]-N-ethyl-N-methyl-formamidine (K.1.29), N'-(5-bromo-6-indan-2-yloxy-2-methyl-3-pyridyl)-N-ethyl-N-methyl-formamidine (K.1.30), N'-[5-bromo-6-[1-(3,5-difluorophenyhethoxy]-2-methyl-3-pyridyl]-N-ethyl-N-methyl-formamidine (K.1.31), N'-[5-bromo-6-(4-isopropylcyclohexoxy)-2-methyl-3-pyridyl]-N-ethyl-N-methyl-formamidine (K.1.32), N'-[5-bromo-2-methyl-6-(1-phenylethoxy)-3-pyridyl]-N-ethyl-N-methyl-formamidine (K.1.33), N'-(2-methyl-5-trifluoromethyl-4-(3-trimethylsilanyl-propoxy)-phenyl)-N-ethyl-N-methyl formamidine (K.1.34), N'-(5-difluoromethyl-2-methyl-4-(3-trimethylsilanyl-propoxy)-phenyl)-N-ethyl-N-methyl formamidine (K.1.35), 2-(4-chloro-phenyl)-N-[4-(3,4-dimethoxy-phenyl)-isoxazol-5-yl]-2-prop-2-ynyloxy-acetamide (K.1.36), 3-[5-(4-chloro-phenyl)-2,3-dimethyl-isoxazolidin-3-yl]-pyridine (pyrisoxazole) (K.1.37), 3-[5-(4-methylphenyl)-2,3-dimethyl-isoxazolidin-3 yl]-pyridine (K.1.38), 5-chloro-1-(4,6-dimethoxy-pyrimidin-2-yl)-2-methyl-1H-benzoimidazole (K.1.39), ethyl (Z)-3-amino-2-cyano-3-phenyl-prop-2-enoate (K.1.40), picarbutrazox (K.1.41), pentyl N-[6-[[(Z)-[(1-methyltetrazol-5-yl)-phenyl-methylene]amino]oxymethyl]-2-pyridyl]carbamate (K.1.42), but-3-ynyl N-[6-[[(Z)-[(1-methyltetrazol-5-yl)-phenyl-methylene]amino]oxymethyl]-2-pyridyl]carbamate (K.1.43), 2-[2-[(7,8-difluoro-2-methyl-3-quinolyhoxy)-6-fluoro-phenyl] propan-2-ol (K.1.44), 2-[2-fluoro-6-[(8-fluoro-2-methyl-3-quinolyl)oxy]phen-yl]propan-2-ol (K.1.45), 3-(5-fluoro-3,3,4,4-tetramethyl-3,4-dihydroisoquinolin-1-yhquinoline (K.1.46), quinofumelin (K.1.47), 3-(4,4,5-trifluoro-3,3-dimethyl-3,4-dihydroisoquinolin-1-yl)quinoline (K.1.48), 9-fluoro-2,2-dimethyl-5-(3-quinolyl)-3H-1,4-benzoxazepine (K.1.49), 2-(6-benzyl-2-pyridyl)quinazoline (K.1.50), 2-[6-(3-fluoro-4-methoxy-phenyl)-5-methyl-2-pyridyl]quinazoline (K.1.51), 3-[(3,4-dichloroisothiazol-5-yl)methoxy]-1,2-benzothiazole 1,1-dioxide (K.1.52), N'-(2,5-dimethyl-4-phenoxy-phenyl)-N-ethyl-N-methyl-formamidine (K.1.53).

M) Growth regulators abscisic acid (M.1.1), amidochlor, ancymidol, 6-benzylaminopurine, brassinolide, butralin, chlormequat, chlormequat chloride, choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat, mepiquat chloride, naphthaleneacetic acid, N-6-benzyladenine, paclobutrazol, prohexadione, prohexadione-calcium, prohydrojasmon, thidiazuron, triapenthenol, tributyl phosphorotrithioate, 2,3,5-tri-iodobenzoic acid, trinexapac-ethyl and uniconazole;

N) Herbicides from classes N.1 to N.15

N.1 Lipid biosynthesis inhibitors: alloxydim (N.1.1), alloxydim-sodium (N.1.2), butroxydim (N.1.3), clethodim (N.1.4), clodinafop (N.1.5), clodinafop-propargyl (N.1.6), cycloxydim (N.1.7), cyhalofop (N.1.8), cyhalofop-butyl (N.1.9), diclofop(N.1.10), diclofop-methyl (N.1.11), fenoxaprop (N.1.12), fenoxaprop-ethyl (N.1.13), fenoxaprop-P (N.1.14), fenoxaprop-P-ethyl (N.1.15), fluazifop (N.1.16), fluazifop-butyl (N.1.17), fluazifop-P (N.1.18), fluazifop-P-butyl (N.1.19), haloxyfop (N.1.20), haloxyfop-methyl (N.1.21), haloxyfop-P (N.1.22), haloxyfop-P-methyl (N.1.23), metamifop (N.1.24), pinoxaden (N.1.25), profoxydim (N.1.26), propaquizafop (N.1.27), quizalofop (N.1.28), quizalofop-ethyl (N.1.29), quizalofop-tefuryl (N.1.30), quizalofop-P (N.1.31), quizalofop-P-ethyl (N.1.32), quizalofop-P-tefuryl (N.1.33), sethoxydim (N.1.34), tepraloxydim (N.1.35), tralkoxydim (N.1.36), 4-(4'-chloro-4-cyclo¬propyl-2'-fluoro[1,1'-biphenyl]-3-yl)-5-hydroxy-2,2,6,6-tetramethyl-2H-pyran-3(6H)-one ((N.1.37) CAS 1312337-72-6); 4-(2',4'-dichloro-4-cyclopropyl[1,1'-biphenyl]-3-yl)-5-hydroxy-2,2,6,6-tetramethyl-2H-pyran-3(6H)-one ((N.1.38) CAS 1312337-45-3); 4-(4'-chloro-4-ethyl-2'-fluoro[1,1'-biphenyl]-3-yl)-5-hydroxy-2,2,6,6-tetramethyl-2H-pyran-3(6H)-one ((N.1.39) CAS 1033757-93-5); 4-(2',4'-Dichloro-4-ethyl[1,1'-biphenyl]-3-yl)-2,2,6,6-tetramethyl-2H-pyran-3,5(4H,6H)-dione ((N.1.40) CAS 1312340-84-3); 5-(acetyloxy)-4-(4'-chloro-4-cyclopropyl-2'-fluoro[1,1'-biphenyl]-3-yl)-3,6-dihydro-2,2,6,6-tetramethyl-2H-pyran-3-one ((N.1.41) CAS 1312337-48-6); 5-(acetyloxy)-4-(2",4'-dichloro-4-cyclopropyl-[1,1'-biphenyl]-3-yl)-3,6-dihydro-2,2,6,6-tetramethyl-2H-pyran-3-one (N.1.42); 5-(acetyloxy)-4-(4'-chloro-4-ethyl-2'-fluoro[1,1'-biphenyl]-3-yl)-3,6-dihydro-2,2,6,6-tetramethyl-2H-pyran-3-one ((N.1.43) CAS 1312340-82-1); 5-(acetyloxy)-4-(2',4'-dichloro-4-ethyl[1,1'-biphenyl]-3-yl)-3,6-dihydro-2,2,6,6-tetramethyl-2H-pyran-3-one ((N.1.44) CAS 1033760-55-2); 4-(4'-chloro-4-cyclopropyl-2'-fluoro[1,1'-biphenyl]-3-yl)-5,6-dihydro-2,2,6,6-tetramethyl-5-oxo-2H-pyran-3-yl carbonic acid methyl ester ((N.1.45) CAS 1312337-51-1); 4-(2",4'-dichloro-4-cyclopropyl-[1,1'-biphenyl]-3-yl)-5,6-dihydro-2,2,6,6-tetramethyl-5-oxo-2H-pyran-3-yl carbonic acid methyl ester (N.1.46); 4-(4'-chloro-4-ethyl-2'-fluoro[1,1'-biphenyl]-3-yl)-5,6-dihydro-2,2,6,6-tetramethyl-5-oxo-2H-pyran-3-yl carbonic acid methyl ester ((N.1.47) CAS 1312340-83-2); 4-(2',4'-dichloro-4-ethyl-[1,1'-biphenyl]-3-yl)-5,6-dihydro-2,2,6,6-tetramethyl-5-oxo-2H-pyran-3-yl carbonic acid methyl ester ((N.1.48) CAS 1033760-58-5); benfuresate (N.1.49), butylate (N.1.50), cycloate (N.1.51), dalapon (N.1.52), dimepiperate (N.1.53), EPTC (N.1.54), esprocarb (N.1.55), ethofumesate (N.1.56), flupropanate (N.1.57), molinate (N.1.58), orbencarb (N.1.59), pebulate (N.1.60), prosulfocarb (N.1.61), TCA (N.1.62), thiobencarb (N.1.63), tiocarbazil (N.1.64), triallate (N.1.65) and vernolate (N.1.66);

N.2 ALS inhibitors: amidosulfuron (N.2.1), azimsulfuron (N.2.2), bensulfuron (N.2.3), bensul-furon-methyl (N.2.4), chlorimuron (N.2.5), chlorimuron-ethyl (N.2.6), chlorsulfuron (N.2.7), cinosulfuron (N.2.8), cyclosulfamuron (N.2.9), ethametsulfuron (N.2.10), ethametsulfuron-methyl (N.2.11), ethoxysulfuron (N.2.12), flazasulfuron (N.2.13), flucetosulfuron (N.2.14), flupyrsulfuron (N.2.15), flupyrsulfuron-methyl-sodium (N.2.16), foramsulfuron (N.2.17), halosulfuron (N.2.18), halosulfuron-methyl (N.2.19), imazosulfuron (N.2.20), iodosulfuron (N.2.21), iodosulfuron-methyl-sodium (N.2.22), iofensulfuron (N.2.23), iofensulfuron-sodium (N.2.24), mesosulfuron (N.2.25), metazosulfuron (N.2.26), metsulfuron (N.2.27), metsulfuron-methyl (N.2.28), nicosulfuron (N.2.29), orthosulfamuron (N.2.30), oxasulfuron (N.2.31), primisulfuron (N.2.32), primisulfuron-methyl (N.2.33), propyrisulfuron (N.2.34), prosulfuron (N.2.35), pyrazosulfuron (N.2.36), pyrazosulfuron-ethyl (N.2.37), rimsulfuron (N.2.38), sulfometuron (N.2.39), sulfometuron-methyl (N.2.40), sulfosulfuron (N.2.41), thifensulfuron (N.2.42), thifensulfuron-methyl (N.2.43), triasulfuron (N.2.44), tribenuron (N.2.45), tribenuron-methyl (N.2.46), trifloxysulfuron (N.2.47), triflusulfuron (N.2.48), triflusulfuron-methyl (N.2.49), tritosulfuron (N.2.50), imazamethabenz (N.2.51), imazamethabenz-methyl (N.2.52), imazamox (N.2.53), imazapic (N.2.54), imazapyr (N.2.55), imazaquin (N.2.56), imazethapyr (N.2.57); cloransulam (N.2.58), cloransulam-methyl (N.2.59), diclosulam (N.2.60), flumetsulam (N.2.61), florasulam (N.2.62), metosulam (N.2.63), penoxsulam (N.2.64), pyrimisulfan (N.2.65) and pyroxsulam (N.2.66); bispyribac (N.2.67), bispyribac-sodium (N.2.68), pyribenzoxim (N.2.69), pyriftalid (N.2.70), pyriminobac (N.2.71), pyriminobac-methyl (N.2.72), pyrithiobac (N.2.73), pyrithiobac-sodium (N.2.74), 4-[[[2-[(4,6-dimethoxy-2-pyrimidinyl)oxy]phenyl]methyl]amino]-benzoic acid-1-methyhethyl ester ((N.2.75) CAS 420138-41-6), 4-[[[2-[(4,6-dimethoxy-2-pyrimidinyl)oxy]phenyl]¬methyl]amino]-benzoic acid propyl ester ((N.2.76) CAS 420138-40-5), N-(4-bromophenyl)-2-[(4,6-dimethoxy-2-pyrimidinyl)oxy]benzenemethanamine ((N.2.77) CAS 420138-01-8); flucarbazone (N.2.78), flucarbazone-sodium (N.2.79), propoxycarbazone (N.2.80), propoxycarbazone-sodium (N.2.81), thiencarbazone (N.2.82), thiencarbazone-methyl (N.2.83), triafamone (N.2.84);

N.3 Photosynthesis inhibitors: amicarbazone (N.3.1); chlorotriazine (N.3.2); ametryn (N.3.3), atrazine (N.3.4), chloridazone (N.3.5), cyanazine (N.3.6), desmetryn (N.3.7), dimethametryn (N.3.8), hexazinone (N.3.9), metribuzin (N.3.10), prometon (N.3.11), prometryn (N.3.12), propazine (N.3.13), simazine (N.3.14), simetryn (N.3.15), terbumeton (N.3.16), terbuthylazin (N.3.17), terbutryn (N.3.18), trietazin (N.3.19); chlorbromuron (N.3.20), chlorotoluron (N.3.21), chloroxuron (N.3.22), dimefuron (N.3.23), diuron (N.3.24), fluometuron (N.3.25), isoproturon (N.3.26), isouron (N.3.27), linuron (N.3.28), metamitron (N.3.29), methabenzthiazuron (N.3.30), metobenzuron (N.3.31), metoxuron (N.3.32), monolinuron (N.3.33), neburon (N.3.34), siduron (N.3.35), tebuthiuron (N.3.36), thiadiazuron (N.3.37), desmedipham (N.3.38), karbutilat (N.3.39), phenmedipham (N.3.40), phenmedipham-ethyl (N.3.41), bromofenoxim (N.3.42), bromoxynil (N.3.43) and its salts and esters, ioxynil (N.3.44) and its salts and esters, bromacil (N.3.45), lenacil (N.3.46), terbacil (N.3.47), bentazon (N.3.48), bentazon-sodium (N.3.49), pyridate (N.3.50), pyridafol (N.3.51), pentanochlor (N.3.52), propanil (N.3.53); diquat (N.3.54), diquat-dibromide (N.3.55), paraquat (N.3.56), paraquat-dichloride (N.3.57), paraquat-dimetilsulfate (N.3.58);

N.4 protoporphyrinogen-IX oxidase inhibitors: acifluorfen (N.4.1), acifluorfen-sodium (N.4.2), azafenidin (N.4.3), bencarbazone (N.4.4), benzfendizone (N.4.5), bifenox (N.4.6), butafenacil (N.4.7), carfentrazone (N.4.8), carfentrazone-ethyl (N.4.9), chlormethoxyfen (N.4.10), cinidon-ethyl (N.4.11), fluazolate (N.4.12), flufenpyr (N.4.13), flufenpyr-ethyl (N.4.14), flumiclorac (N.4.15), flumiclorac-pentyl (N.4.16), flumioxazin (N.4.17), fluoroglycofen (N.4.18), fluoroglycofen-ethyl (N.4.19), fluthiacet (N.4.20), fluthiacet-methyl (N.4.21), fomesafen (N.4.22), halosafen (N.4.23), lactofen (N.4.24), oxadiargyl (N.4.25), oxadiazon (N.4.26), oxyfluorfen (N.4.27), pentoxazone (N.4.28), profluazol (N.4.29), pyraclonil (N.4.30), pyraflufen (N.4.31), pyraflufen-ethyl (N.4.32), saflufenacil (N.4.33), sulfentrazone (N.4.34), thidiazimin (N.4.35), tiafenacil (N.4.36), trifludimoxazin (N.4.37), ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate ((N.4.38) CAS 353292-31-6), N-ethyl-3-(2,6-dichloro-4-trifluoro-methyl-phenoxy)-5-methyl-1H-pyrazole-1-carboxamide ((N.4.39) CAS 452098-92-9), N tetrahydrofurfuryl-3-(2,6-dichloro-4-trifluoromethylphenoxy)-5-methyl-1H-pyrazole-1-carboxamide ((N.4.40) CAS 915396-43-9), N-ethyl-3-(2-chloro-6-fluoro-4-trifluoromethyl¬phenoxy)-5-methyl-1H-pyrazole-1-carboxamide ((N.4.41) CAS 452099-05-7), N tetrahydro¬furfuryl-3-(2-chloro-6-fluoro-4-trifluoro¬methylphenoxy)-5-methyl-1H-pyrazole-1-carboxamide ((N.4.42) CAS 452100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione ((N.4.43) CAS 451484-50-7), 2-(2,2,7-trifluoro-3-oxo-4-prop-2-ynyl-3,4-dihydro-2H-benzo[1,4]oxazin-6-yl)-4,5,6,7-tetrahydro-isoindole-1,3-dione ((N.4.44) CAS 1300118-96-0), 1-methyl-6-trifluoro¬methyl-3-(2,2,7-tri-fluoro-3-oxo-4-prop-2-ynyl-3,4-dihydro-2H-benzo[1,4]oxazin-6-yl)-1H-pyrimidine-2,4-dione ((N.4.45) CAS 1304113-05-0), methyl (E)-4-[2-chloro-5-[4-chloro-5-(difluoromethoxy)-1H-methyl-pyrazol-3-yl]-4-fluoro-phenoxy]-3-methoxy-but-2-enoate ((N.4.46) CAS 948893-00-3), 3-[7-chloro-5-fluoro-2-(trifluoromethyl)-1H-benzimidazol-4-yl]-1-methyl-6-(trifluoromethyl)-1H-pyrimidine-2,4-dione ((N.4.47) CAS 212754-02-4);

N.5 Bleacher herbicides: beflubutamid (N.5.1), diflufenican (N.5.2), fluridone (N.5.3), flurochloridone (N.5.4), flurtamone (N.5.5), norflurazon (N.5.6), picolinafen (N.5.7), 4-(3-trifluoromethyl¬phenoxy)-2-(4-trifluoromethylphenyl)¬pyrimidine ((N.5.8) CAS 180608-33-7); benzobicyclon (N.5.9), benzofenap (N.5.10), bicyclopyrone (N.5.11), clomazone (N.5.12), fenquintrione (N.5.13), isoxaflutole (N.5.14), mesotrione (N.5.15), pyrasulfotole (N.5.16), pyrazolynate (N.5.17), pyrazoxyfen (N.5.18), sulcotrione (N.5.19), tefuryltrione (N.5.20), tembotrione (N.5.21), tolpyralate (N.5.22), topramezone (N.5.23); aclonifen (N.5.24), amitrole (N.5.25), flumeturon (N.5.26);

N.6 EPSP synthase inhibitors: glyphosate (N.6.1), glyphosate-isopropylammonium (N.6.2), glyposate-potassium (N.6.3), glyphosate-trimesium (sulfosate) (N.6.4);

N.7 Glutamine synthase inhibitors: bilanaphos (bialaphos) (N.7.1), bilanaphos-sodium (N.7.2), glufosinate (N.7.3), glufosinate-P (N.7.4), glufosinate-ammonium (N.7.5);

N.8 DHP synthase inhibitors: asulam (N.8.1);

N.9 Mitosis inhibitors: benfluralin (N.9.1), butralin (N.9.2), dinitramine (N.9.3), ethalfluralin (N.9.4), fluchloralin (N.9.5), oryzalin (N.9.6), pendimethalin (N.9.7), prodiamine (N.9.8), trifluralin (N.9.9); amiprophos (N.9.10), amiprophos-methyl (N.9.11), butamiphos (N.9.12); chlorthal (N.9.13), chlorthal-dimethyl (N.9.14), dithiopyr (N.9.15), thiazopyr (N.9.16), propyzamide (N.9.17), tebutam (N.9.18); carbetamide (N.9.19), chlorpropham (N.9.20), flamprop (N.9.21), flamprop-isopropyl (N.9.22), flamprop-methyl (N.9.23), flamprop-M-isopropyl (N.9.24), flamprop-M-methyl (N.9.25), propham (N.9.26);

N.10 VLCFA inhibitors: acetochlor (N.10.1), alachlor (N.10.2), butachlor (N.10.3), dimethachlor (N.10.4), dimethenamid (N.10.5), dimethenamid-P (N.10.6), metazachlor (N.10.7), metolachlor (N.10.8), metolachlor-S (N.10.9), pethoxamid (N.10.10), pretilachlor (N.10.11), propachlor (N.10.12), propisochlor (N.10.13), thenylchlor (N.10.14), flufenacet (N.10.15), mefenacet (N.10.16), diphenamid (N.10.17), naproanilide (N.10.18), napropamide (N.10.19), napropamide-M (N.10.20), fentrazamide (N.10.21), anilofos (N.10.22), cafenstrole (N.10.23), fenoxasulfone (N.10.24), ipfencarbazone (N.10.25), piperophos (N.10.26), pyroxasulfone (N.10.27), isoxazoline compounds of the formulae II.1, II.2, II.3, II.4, II.5, II.6, II.7, II.8 and II.9

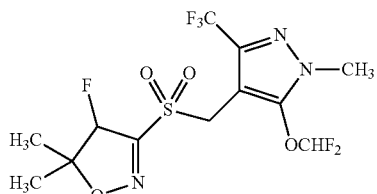

II.1

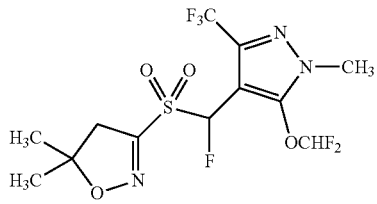

II.2

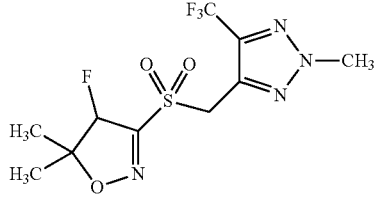

II.3

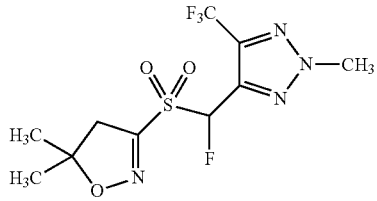

II.4

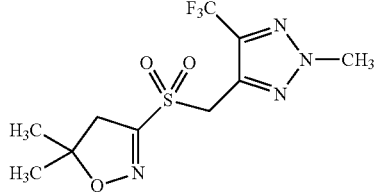

II.5

-continued

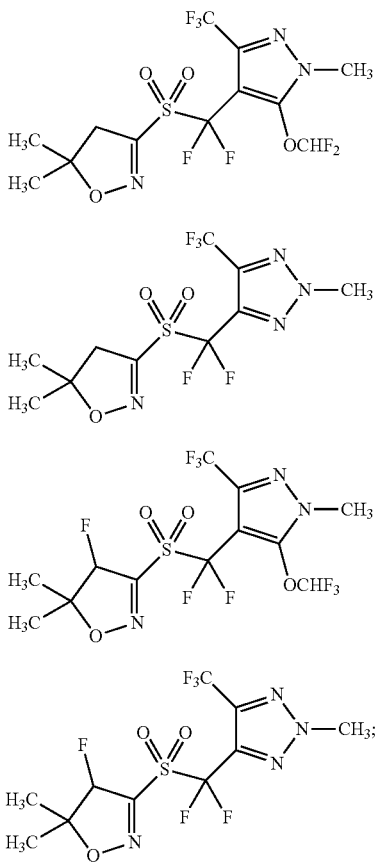

N.11 Cellulose biosynthesis inhibitors: chlorthiamid (N.11.1), dichlobenil (N.11.2), flupoxam (N.11.3), indaziflam (N.11.4), isoxaben (N.11.5), triaziflam (N.11.6), 1-cyclohexyl-5-pentafluorphenyloxy-14-[1,2,4,6]thiatriazin-3-ylamine ((N.11.7) CAS 175899-01-1);

N.12 Decoupler herbicides: dinoseb (N.12.1), dinoterb (N.12.2), DNOC (N.12.3) and its salts;

N.13 Auxinic herbicides: 2,4-D (N.13.1) and its salts and esters, clacyfos (N.13.2), 2,4-DB (N.13.3) and its salts and esters, aminocyclopyrachlor (N.13.4) and its salts and esters, aminopyralid (N.13.5) and its salts such as aminopyralid-dimethylammonium (N.13.6), aminopyralid-tris(2-hydroxypropyl)ammonium (N.13.7) and its esters, benazolin (N.13.8), benazolin-ethyl (N.13.9), chloramben (N.13.10) and its salts and esters, clomeprop (N.13.11), clopyralid (N.13.12) and its salts and esters, dicamba (N.13.13) and its salts and esters, dichlorprop (N.13.14) and its salts and esters, dichlorprop-P (N.13.15) and its salts and esters, fluroxypyr (N.13.16), fluroxypyr-butometyl (N.13.17), fluroxypyr-meptyl (N.13.18), halauxifen (N.13.) and its salts and esters (CAS 943832-60-8); MCPA (N.13.) and its salts and esters, MCPA-thioethyl (N.13.19), MCPB (N.13.20) and its salts and esters, mecoprop (N.13.21) and its salts and esters, mecoprop-P (N.13.22) and its salts and esters, picloram (N.13.23) and its salts and esters, quinclorac (N.13.24), quinmerac (N.13.25), TBA (2,3,6) (N.13.26) and its salts and esters, triclopyr (N.13.27) and its salts and esters, 4-amino-3-chloro-6-(4-chloro-2-fluoro-3-meth-oxyphenyl)-5-fluoropyridine-2-carboxylic acid (N.13.28), benzyl 4-amino-3-chloro-6-(4-chloro-2-fluoro-3-methoxyphenyl)-5-fluoropyridine-2-carboxylate ((N.13.29) CAS 1390661-72-9);

N.14 Auxin transport inhibitors: diflufenzopyr (N.14.1), diflufenzopyr-sodium (N.14.2), naptalam (N.14.3) and naptalam-sodium (N.14.4);

N.15 Other herbicides: bromobutide (N.15.1), chlorflurenol (N.15.2), chlorflurenol-methyl (N.15.3), cinmethylin (N.15.4), cumyluron (N.15.5), cyclopyrimorate ((N.15.6) CAS 499223-49-3) and its salts and esters, dalapon (N.15.7), dazomet (N.15.8), difenzoquat (N.15.9), difenzoquat-metilsulfate (N.15.10), dimethipin (N.15.11), DSMA (N.15.12), dymron (N.15.13), endothal (N.15.14) and its salts, etobenzanid (N.15.15), flurenol (N.15.16), flurenol-butyl (N.15.17), flurprimidol (N.15.18), fosamine (N.15.19), fosamine-ammonium (N.15.20), indanofan (N.15.21), maleic hydrazide (N.15.22), mefluidide (N.15.23), metam (N.15.24), methiozolin ((N.15.25) CAS 403640-27-7), methyl azide (N.15.26), methyl bromide (N.15.27), methyldymron (N.15.28), methyl iodide (N.15.29), MSMA (N.15.30), oleic acid (N.15.31), oxaziclomefone (N.15.32), pelargonic acid (N.15.33), pyributicarb (N.15.34), quinoclamine (N.15.35), tridiphane (N.15.36);

O) Insecticides from classes O.1 to O.29

O.1 Acetylcholine esterase (AChE) inhibitors: aldicarb (O.1.1), alanycarb (O.1.2), bendiocarb (O.1.3), benfuracarb (O.1.4), butocarboxim (O.1.5), butoxycarboxim (O.1.6), carbaryl (O.1.7), carbofuran (O.1.8), carbosulfan (O.1.9), ethiofencarb (O.1.10), fenobucarb (O.1.11), formetanate (O.1.12), furathiocarb (O.1.13), isoprocarb (O.1.14), methiocarb (O.1.15), methomyl (O.1.16), metolcarb (O.1.17), oxamyl (O.1.18), pirimicarb (O.1.19), propoxur (O.1.20), thiodicarb (O.1.21), thiofanox (O.1.22), trimethacarb (O.1.23), XMC (O.1.24), xylylcarb (O.1.25) and triazamate (O.1.26); acephate (O.1.27), azamethiphos (O.1.28), azinphos-ethyl (O.1.29), azinphosmethyl (O.1.30), cadusafos (O.1.31), chlorethoxyfos (O.1.32), chlorfenvinphos (O.1.33), chlormephos (O.1.34), chlorpyrifos (O.1.35), chlorpyrifos-methyl (O.1.36), coumaphos (O.1.37), cyanophos (O.1.38), demeton-S-methyl (O.1.39), diazinon (O.1.40), dichlorvos/DDVP (O.1.41), dicrotophos (O.1.42), dimethoate (O.1.43), dimethylvinphos (O.1.44), disulfoton (O.1.45), EPN (O.1.46), ethion (O.1.47), ethoprophos (O.1.48), famphur (O.1.49), fenamiphos (O.1.50), fenitrothion (O.1.51), fenthion (O.1.52), fosthiazate (O.1.53), heptenophos (O.1.54), imicyafos (O.1.55), isofenphos (O.1.56), isopropyl 0-(methoxyaminothio-phosphoryl) salicylate (O.1.57), isoxathion (O.1.58), malathion (O.1.59), mecarbam (O.1.60), methamidophos (O.1.61), methidathion (O.1.62), mevinphos (O.1.63), monocrotophos (O.1.64), naled (O.1.65), omethoate (O.1.66), oxydemeton-methyl (O.1.67), parathion (O.1.68), parathion-methyl (O.1.69), phenthoate (O.1.70), phorate (O.1.71), phosalone (O.1.72), phosmet (O.1.73), phosphamidon (O.1.74), phoxim (O.1.75), pirimiphos-methyl (O.1.76), profenofos (O.1.77), propetamphos (O.1.78), prothiofos (O.1.79), pyraclofos (O.1.80), pyridaphenthion (O.1.81), quinalphos (O.1.82), sulfotep (O.1.83), tebupirimfos (O.1.84), temephos (O.1.85), terbufos (O.1.86), tetrachlorvinphos (O.1.87), thiometon (O.1.88), triazophos (O.1.89), trichlorfon (O.1.90), vamidothion (O.1.91);

O.2 GABA-gated chloride channel antagonists: endosulfan (O.2.1), chlordane (O.2.2); ethiprole (O.2.3), fipronil (O.2.4), flufiprole (O.2.5), pyrafluprole (O.2.6), pyriprole (O.2.7);

O.3 Sodium channel modulators: acrinathrin (O.3.1), allethrin (O.3.2), d-cis-trans allethrin (O.3.3), d-trans allethrin (O.3.4), bifenthrin (O.3.5), bioallethrin (O.3.6), bioallethrin S-cylclopentenyl (O.3.7), bioresmethrin (O.3.8), cycloprothrin (O.3.9), cyfluthrin (O.3.10), betacyfluthrin (O.3.11), cyhalothrin (O.3.12), lambda-cyhalothrin (O.3.13), gamma-cyhalothrin (O.3.14), cypermethrin (O.3.15), alpha-cypermethrin (O.3.16), beta-cypermethrin (O.3.17), theta-cypermethrin (O.3.18), zeta-cypermethrin (O.3.19), cyphenothrin (O.3.20), deltamethrin (O.3.21), empenthrin (O.3.22), esfenvalerate (O.3.23), etofenprox (O.3.24), fenpropathrin (O.3.25), fenvalerate (O.3.26), flucythrinate (O.3.27), flumethrin (O.3.28), tau-fluvalinate (O.3.29), halfenprox (O.3.30), heptafluthrin (O.3.31), imiprothrin (O.3.32), meperfluthrin (O.3.33), metofluthrin (O.3.34), momfluorothrin (O.3.35), permethrin (O.3.36), phenothrin (O.3.37), prallethrin (O.3.38), profluthrin (O.3.39), pyrethrin (pyrethrum) (O.3.40), resmethrin (O.3.41), silafluofen (O.3.42), tefluthrin (O.3.43), tetramethylfluthrin (O.3.44), tetramethrin (O.3.45), tralomethrin (O.3.46) and transfluthrin (O.3.47); DDT (O.3.48), methoxychlor (O.3.49);

O.4 Nicotinic acetylcholine receptor agonists (nAChR): acetamiprid (O.4.1), clothianidin (O.4.2), cycloxaprid (O.4.3), dinotefuran (O.4.4), imidacloprid (O.4.5), nitenpyram (O.4.6), thiacloprid (O.4.7), thiamethoxam (O.4.8); (2E)-1-[(6-chloropyridin-3-Amethyl]-N'-nitro-2-pentylidene-hydrazinecarboximidamide (O.4.9); 1-[(6-chloropyridin-3-Amethyl]-7-methyl-8-nitro-5-propoxy-1,2,3,5,6,7-hexahydroimidazo[1,2-a]pyridine (O.4.10); nicotine (O.4.11);

O.5 Nicotinic acetylcholine receptor allosteric activators: spinosad (O.5.1), spinetoram (O.5.2);

O.6 Chloride channel activators: abamectin (O.6.1), emamectin benzoate (O.6.2), ivermectin (O.6.3), lepimectin (O.6.4), milbemectin (O.6.5);

O.7 Juvenile hormone mimics: hydroprene (O.7.1), kinoprene (O.7.2), methoprene (O.7.3); fenoxycarb (O.7.4), pyriproxyfen (O.7.5);

O.8 miscellaneous non-specific (multi-site) inhibitors: methyl bromide (O.8.1) and other alkyl halides; chloropicrin (O.8.2), sulfuryl fluoride (O.8.3), borax (O.8.4), tartar emetic (O.8.5);

O.9 Selective homopteran feeding blockers: pymetrozine (O.9.1), flonicamid (O.9.2);

O.10 Mite growth inhibitors: clofentezine (O.10.1), hexythiazox (O.10.2), diflovidazin (O.10.3); etoxazole (O.10.4);

O.11 Microbial disruptors of insect midgut membranes: the Bt crop proteins: Cry1Ab, Cry1Ac, Cry1Fa, Cry2Ab, mCry3A, Cry3Ab, Cry3Bb, Cry34/35Ab1;

O.12 Inhibitors of mitochondrial ATP synthase: diafenthiuron (O.12.1); azocyclotin (O.12.2), cyhexatin (O.12.3), fenbutatin oxide (O.12.4), propargite (O.12.5), tetradifon (O.12.6);

O.13 Uncouplers of oxidative phosphorylation via disruption of the proton gradient: chlorfenapyr (O.13.1), DNOC (O.13.2), sulfluramid (O.13.3);

O.14 Nicotinic acetylcholine receptor (nAChR) channel blockers: bensultap (O.14.1), cartap hydrochloride (O.14.2), thiocyclam (O.14.3), thiosultap sodium (O.14.4);

O.15 Inhibitors of the chitin biosynthesis type 0: bistrifluron (O.15.1), chlorfluazuron (O.15.2), diflubenzuron (O.15.3), flucycloxuron (O.15.4), flufenoxuron (O.15.5), hexaflumuron (O.15.6), lufenuron (O.15.7), novaluron (O.15.8), noviflumuron (O.15.9), teflubenzuron (O.15.10), triflumuron (O.15.11);

O.16 Inhibitors of the chitin biosynthesis type 1: buprofezin (O.16.1);

O.17 Moulting disruptors: cyromazine (O.17.1);

O.18 Ecdyson receptor agonists: methoxyfenozide (O.18.1), tebufenozide (O.18.2), halofenozide (O.18.3), fufenozide (O.18.4), chromafenozide (O.18.5);

O.19 Octopamin receptor agonists: amitraz (O.19.1);

O.20 Mitochondrial complex III electron transport inhibitors: hydramethylnon (O.20.1), acequinocyl (O.20.2), fluacrypyrim (O.20.3);

O.21 Mitochondrial complex I electron transport inhibitors: fenazaquin (O.21.1), fenpyroximate (O.21.2), pyrimidifen (O.21.3), pyridaben (O.21.4), tebufenpyrad (O.21.5), tolfenpyrad (O.21.6); rotenone (O.21.7);

O.22 Voltage-dependent sodium channel blockers: indoxacarb (O.22.1), metaflumizone (O.22.2), 2-[2-(4-cyanophenyl)-1-[3-(trifluoromethyl)phenyl]ethylidene]-N4-[4-(difluoromethoxy)phenyl]-hydrazinecarboxamide (O.22.3), N-(3-chloro-2-methylphenyl)-2-[(4-chlorophenyl)-[4-[methyl(methylsulfonyl)amino]phenyl]methylene]-hydrazinecarboxamide (O.22.4);

O.23 Inhibitors of the of acetyl CoA carboxylase: spirodiclofen (O.23.1), spiromesifen (O.23.2), spirotetramat (O.23.3);

O.24 Mitochondrial complex IV electron transport inhibitors: aluminium phosphide (O.24.1), calcium phosphide (O.24.2), phosphine (O.24.3), zinc phosphide (O.24.4), cyanide (O.24.5);

O.25 Mitochondrial complex II electron transport inhibitors: cyenopyrafen (O.25.1), cyflumetofen (O.25.2);

O.26 Ryanodine receptor-modulators: flubendiamide (O.26.1), chlorantraniliprole (O.26.2), cyantraniliprole (O.26.3), cyanliliprole (O.26.4), tetraniliprole (O.26.5); (R)-3-chloro-N1-{2-methyl-4-[1,2,2,2-tetrafluoro-1-(trifluoromethypethyl]phenyl}-N2-(1-methyl-2-methylsulfonylethyl)phthalamide (O.26.6), (S)-3-chloro-N1-{2-methyl-4-[1,2,2,2-tetrafluoro-1-(trifluoromethypethyl]phenyl}-N2-(1-methyl-2-methylsulfonylethyl)phthalamide (O.26.7), methyl-2-[3,5-dibromo-2-({[3-bromo-1-(3-chloropyridin-2-yl)-1H-pyrazol-5-yl]carbonyl}amino)benzoyl]-1,2-dimethylhydrazinecarboxylate (O.26.8); N-[4,6-dichloro-2-[(diethyl-lambda-4-sulfanylidene)-carbamoyl]-phenyl]-2-(3-chloro-2-pyridyl)-5-(trifluoromethyl)pyrazole-3-carboxamide (O.26.9); N-[4-chloro-2-[(diethyl-lambda-4-sulfanylidene)carbamoyl]-6-methyl-phenyl]-2-(3-chloro-2-pyridyl)-5-(trifluoromethyl)pyrazole-3-carboxamide (O.26.10); N-[4-chloro-2-[(di-2-propyl-lambda-4-sulfanylidene)carbamoyl]-6-methyl-phenyl]-2-(3-chloro-2-pyridyl)-5-(trifluoromethyl)pyrazole-3-carboxamide (O.26.11); N-[4,6-dichloro-2-[(di-2-propyl-lambda-4-sulfanylidene)carbamoyl]-phenyl]-2-(3-chloro-2-pyridyl)-5-(trifluoromethyl)pyrazole-3-carboxamide (O.26.12); N-[4,6-dibromo-2-[(diethyl-lambda-4-sulfanylidene)carbamoyl]-phenyl]-2-(3-chloro-2-pyridyl)-5-(tri-fluoromethyl)pyrazole-3-carboxamide (O.26.13); N-[2-(5-amino-1,3,4-thiadiazol-2-yl)-4-chloro-6-methylphenyl]-3-bromo-1-(3-chloro-2-pyridinyl)-1H-pyrazole-5-carboxamide (O.26.14); 3-chloro-1-(3-chloro-2-pyridinyl)-N-[2,4-dichloro-6-[[(1-cyano-1-methylethyl)amino]carbonyl]phenyl]-1H-pyrazole-5-carboxamide (O.26.15); 3-bromo-N-[2,4-dichloro-6-(methylcarbamoyl)phenyl]-1-(3,5-dichloro-2-pyridyl)-1H-pyrazole-5-carboxamide (O.26.16); N-[4-chloro-2-[[(1,1-dimethylethyl)amino]carbonyl]-6-methylphenyl]-1-(3-chloro-2-pyridinyl)-3-(fluoromethoxy)-1H-pyrazole-5-carboxamide (O.26.17); cyhalodiamide (O.26.18);

O.27. insecticidal active compounds of unknown or uncertain mode of action: afidopyropen (O.27.1), afoxolaner (O.27.2), azadirachtin (O.27.3), amidoflumet (O.27.4), benzoximate (O.27.5), bifenazate (O.27.6), broflanilide (O.27.7), bromopropylate (O.27.8), chinomethionat (O.27.9), cryolite (O.27.10), dicloromezotiaz (O.27.11), dicofol (O.27.12), flufenerim (O.27.13), flometoquin (O.27.14), fluensulfone (O.27.15), fluhexafon (O.27.16), fluopyram (O.27.17), flupyradifurone (O.27.18), fluralaner (O.27.19), metoxadiazone (O.27.20), piperonyl butoxide (O.27.21), pyflubumide (O.27.22), pyridalyl (O.27.23), pyrifluquinazon (O.27.24), sulfoxaflor (O.27.25), tioxazafen (O.27.26), triflumezopyrim (O.27.27), 11-(4-chloro-2,6-dimethylphenyl)-12-hydroxy-1,4-dioxa-9-azadispiro[4.2.4.2]tetradec-11-en-10-one (O.27.28), 3-(4'-fluoro-2,4-dimethylbiphenyl-3-yl)-4-hydroxy-8-oxa-1-azaspiro[4.5]dec-3-en-2-one (O.27.28), 1-[2-fluoro-4-methyl-5-[(2,2,2-trifluoroethyl)sulfinyl]phenyl]-3-(trifluoromethyl)-1H-1,2,4-triazole-5-amine (O.27.29), (E/Z)—N-[1-[(6-chloro-3-pyridyl)methyl]-2-pyridylidene]-2,2,2-trifluoro-acetamide (O.27.31); (E/Z)—N-[1-[(6-chloro-5-fluoro-3-pyridyl)methyl]-2-pyridylidene]-2,2,2-trifluoro-acetamide (O.27.32); (E/Z)-2,2,2-trifluoro-N-[1-[(6-fluoro-3-pyridyl)methyl]-2-pyridylidene]acetamide (O.27.33); (E/Z)—N-[1-[(6-bromo-3-pyridyl)methyl]-2-pyridylidene]-2,2,2-trifluoro-acetamide (O.27.34); (E/Z)—N-[1-[1-(6-chloro-3-pyridyl)ethyl]-2-pyridylidene]-2,2,2-trifluoro-acetamide (O.27.35); (E/Z)—N-[1-[(6-chloro-3-pyridyl)methyl]-2-pyridylidene]-2,2-difluoro-acetamide (O.27.36); (E/Z)-2-chloro-N-[1-[(6-chloro-3-pyridyl)methyl]-2-pyridylidene]-2,2-difluoro-acetamide (O.27.37); (E/Z)—N-[1-[(2-chloropyrimidin-5-yl)methyl]-2-pyridylidene]-2,2,2-trifluoro-acetamide (O.27.38); (E/Z)—N-[1-[(6-chloro-3-pyridyl)methyl]-2-pyridylidene]-2,2,3,3,3-pentafluoropropanamide (O.27.39); N-[1-[(6-chloro-3-pyridyl)methyl]-2-pyridylidene]-2,2,2-trifluoro-thioacetamide (O.27.40); N-[1-[(6-chloro-3-pyridyl)methyl]-2-pyridylidene]-2,2,2-trifluoro-N'-isopropyl-acetamidine (O.27.41); fluazaindolizine (O.27.42); 4-[5-(3,5-dichlorophenyl)-5-(trifluoromethyl)-4H-isoxazol-3-yl]-2-methyl-N-(1-oxothietan-3-yl)benzamide (O.27.43); fluxamet-amide (O.27.44); 5-[3-[2,6-dichloro-4-(3,3-dichloroallyloxy)phenoxy]propoxy]-1H-pyrazole (O.27.45); 3-(benzoylmethylamino)-N-[2-bromo-4-[1,2,2,3,3,3-hexafluoro-1-(trifluoromethyppropyl]-6-(trifluoromethyl)phenyl]-2-fluoro-benzamide (O.27.46); 3-(benzoylmethylamino)-2-fluoro-N-[2-iodo-4-[1,2,2,2-tetrafluoro-1-(trifluoromethyethyl]-6-(trifluoromethyl)phenyl]-benzamide (O.27.47); N-[3-[[[2-iodo-4-[1,2,2,2-tetrafluoro-1-(trifluoromethyhethyl]-6-(trifluoromethyl)phenyl]amino]carbonyl]phenyl]-N-methyl-benzamide (O.27.48); N-[3-[[[2-bromo-4-[1,2,2,2-tetrafluoro-1-(trifluoromethyhethyl]-6-(trifluoromethyl)phenyl]amino]carbonyl]-2-fluoro-phenyl]-4-fluoro-N-methyl-benzamide (O.27.49); 4-fluoro-N-[2-fluoro-3-[[[2-iodo-4-[1,2,2,2-tetrafluoro-1-(trifluoromethyhethyl]-6-(trifluoro-methyl)phenyl]amino]carbonyl]phenyl]-N-methyl-benzamide (O.27.50); 3-fluoro-N-[2-fluoro-3-[[[2-iodo-4-[1,2,2,2-tetrafluoro-1-(trifluoromethypethyl]-6(trifluoromethyl)phenyl]amino]carbonyl]phenyl]-N-methyl-benzamide (O.27.51); 2-chloro-N-[3-[[[2-iodo-4-[1,2,2,2-tetrafluoro-1-(trifluoromethypethyl]-6-(trifluoromethyl)phenyl]amino]carbonyl]phenyl]-3-pyridinecarboxamide (O.27.52); 4-cyano-N-[2-cyano-5-[[2,6-dibromo-4-[1,2,2,3,3,3-hexafluoro-1-(trifluorometh-yl)propyl]phenyl]carbamoyl]phenyl]-2-methyl-benzamide (O.27.53); 4-cyano-3-[(4-cyano-2-methyl-benzoyl)amino]-N-[2,6-dichloro-4-[1,2,2,3,3,3-hexafluoro-1-(trifluoromethyl)-propyl]phenyl]-2-fluoro-benzamide (O.27.54); N-[5-[[2-chloro-6-cyano-4-[1,2,2,3,3,3-hexafluoro-1-(trifluoromethyl)propyl]phenyl]carbamoyl]-4-cyano-phenyl]-4-cyano-2-methyl-benzamide (O.27.55); N-[5-[[2-bromo-6-chloro-4-[2,2,2-trifluoro-1-hydroxy-1-(trifluoromethyhethyl]phenyl]carbamoyl]-2-cyano-phenyl]-4-cyano-2-methyl-benzamide (O.27.56); N-[5-[[2-bromo-6-chloro-4-[1,2,2,3,3,3-hexafluoro-1-(trifluoromethyl)-propyl]phenyl]carbamoyl]-2-cyano-phenyl]-4-cyano-2-methyl-benzamide (O.27.57); 4-cyano-N-[2-cyano-5-[[2,6-dichloro-4-[1,2,2,3,3,3-hexafluoro-1-(trifluoromethyl)propyl]phenyl]-carbamoyl]phenyl]-2-methyl-benzamide (O.27.58); 4-cyano-N-[2-cyano-5-[[2,6-dichloro-4-[1,2,2,2-tetrafluoro-1-(trifluoromethyhethyl]phenyl]carbamoyl]phenyl]-2-methyl-benzamide (O.27.59); N-[5-[[2-bromo-6-chloro-4-[1,2,2,2-tetrafluoro-1-(trifluoromethyl)ethyl]phenyl]carbamoyl]-2-cyano-phenyl]-4-cyano-2-methyl-benzamide (O.27.60); 2-(1,3-dioxan-2-yl)-6-[2-(3-pyridinyl)-5-thiazolyl]-pyridine; 2-[6-[2-(5-fluoro-3-pyridinyl)-5-thiazolyl]-2-pyridinyl]-pyrimidine (O.27.61); 2-[6-[2-(3-pyridinyl)-5-thiazolyl]-2-pyridinyl]-pyrimidine (O.27.62); N-methylsulfonyl-6-[2-(3-pyridyhthiazol-5-yl]pyridine-2-carboxamide (O.27.63); N-methylsulfonyl-6-[2-(3-pyridyhthiazol-5-yl]pyridine-2-carboxamide (O.27.64); N-ethyl-N-[4-methyl-2-(3-pyridyhthiazol-5-yl]-3-methylthio-propanamide (O.27.65); N-methyl-N-[4-methyl-2-(3-pyridyhthiazol-5-yl]-3-methylthio-propanamide (O.27.66); N,2-dimethyl-N-[4-methyl-2-(3-pyridyhthiazol-5-yl]-3-methylthio-propanamide (O.27.67); N-ethyl-2-methyl-N-[4-methyl-2-(3-pyridyl)thiazol-5-yl]-3-methylthio-propanamide (O.27.68); N-[4-chloro-2-(3-pyridyhthiazol-5-yl]-N-ethyl-2-methyl-3-methylthio-propanamide (O.2769.); N-[4-chloro-2-(3-pyridyhthiazol-5-yl]-N,2-dimethyl-3-methylthio-propanamide (O.27.70); N-[4-chloro-2-(3-pyridyhthiazol-5-yl]-N-methyl-3-methylthio-propanamide (O.27.71); N-[4-chloro-2-(3-pyridyhthiazol-5-yl]-N-ethyl-3-methylthio-propanamide (O.27.72); 1-[(6-chloro-3-pyri-dinyhmethyl]-1,2,3,5,6,7-hexahydro-5-methoxy-7-methyl-8-nitro-imidazo[1,2-a]pyridine (O.27.73); 1-[(6-chloropyridin-3-yhmethyl]-7-methyl-8-nitro-1,2,3,5,6,7-hexahydroimidazo[1,2-a]pyridin-5-ol (O.27.74); 1-isopropyl-N,5-dimethyl-N-pyridazin-4-yl-pyrazole-4-carboxamide (O.27.75); 1-(1,2-dimethylpropyl)-N-ethyl-5-methyl-N-pyridazin-4-yl-pyrazole-4-carboxamide (O.27.76); N,5-dimethyl-N-pyridazin-4-yl-1-(2,2,2-trifluoro-1-methyl-ethyl)pyrazole-4-carboxamide (O.27.77); 1-[1-(1-cyanocyclopropypethyl]-N-ethyl-5-methyl-N-pyridazin-4-yl-pyrazole-4-carboxamide (O.27.78); N-ethyl-1-(2-fluoro-1-methyl-propyl)-5-methyl-N-pyridazin-4-yl-pyrazole-4-carboxamide (O.27.79); 1-(1,2-dimethylpropyl)-N,5-dimethyl-N-pyridazin-4-yl-pyrazole-4-carboxamide (O.27.80); 1-[1-(1-cyanocyclopropypethyl]-N,5-dimethyl-N-pyridazin-4-yl-pyrazole-4-carboxamide (O.27.81); N-methyl-1-(2-fluoro-1-methyl-propyl)-5-methyl-N-pyridazin-4-yl-pyrazole-4-carboxamide (O.27.82); 1-(4,4-difluorocyclohexyl)-N-ethyl-5-methyl-N-pyridazin-4-yl-pyrazole-4-carboxamide (O.27.83); 1-(4,4-difluorocyclohexyl)-N,5-dimethyl-N-pyridazin-4-yl-pyrazole-4-carboxamide (O.27.84), N-(1-methylethyl)-2-(3-pyridinyl)-2H-indazole-4-carboxamide (O.27.85); N-cyclopropyl-2-(3-pyridinyl)-2H-indazole-4-carboxamide (O.27.86); N-cyclohexyl-2-(3-pyridinyl)-2H-indazole-4-carboxamide (O.27.87); 2-(3-pyridinyl)-N-(2,2,2-trifluoroethyl)-2H-indazole-4-carboxamide (O.27.88); 2-(3-pyridinyl)-N-[(tetrahydro-2-furanyhmethyl]-2H-indazole-5-carboxamide (O.27.89); methyl 2-[[2-(3-pyridinyl)-2H-indazol-5-yl]carbonyl]hydrazinecarboxylate (O.27.90); N-[(2,2-difluorocyclopropyhmethyl]-2-(3-pyridinyl)-2H-indazole-5-carboxamide (O.27.91); N-(2,2-difluoropropyl)-2-(3-pyridinyl)-2H-indazole-5-carboxamide (O.27.92); 2-(3-pyridinyl)-N-(2-pyrimidinylmethyl)-2H-indazole-5-carboxamide (O.27.93); N-[(5-methyl-2-pyrazinyhmethyl]-

2-(3-pyridinyl)-2H-indazole-5-carboxamide (O.27.94), N-[3-chloro-1-(3-pyridyl)pyrazol-4-yl]-N-ethyl-3-(3,3,3-trifluoropropylsulfanyl)-propanamide (O.27.95); N-[3-chloro-1-(3-pyridyl)pyrazol-4-yl]-N-ethyl-3-(3,3,3-trifluoropropylsulfinyl)propanamide (O.27.96); N-[3-chloro-1-(3-pyridyl)pyrazol-4-yl]-3-[(2,2-di-fluorocyclopropyl)methylsulfanyl]-N-ethyl-propanamide (O.27.97); N-[3-chloro-1-(3-pyridyl)pyrazol-4-yl]-3-[(2,2-difluorocyclopropyhmethylsulfinyl]-N-ethyl-propanamide (O.27.98); sarolaner (O.27.99), lotilaner (O.27.100).

The active substances referred to as component 2, their preparation and their activity e. g. against harmful fungi is known (cf.: http://www.alanwood.net/pesticides/); these substances are commercially available. The compounds described by IUPAC nomenclature, their preparation and their pesticidal activity are also known (cf. Can. J. Plant Sci. 48(6), 587-94, 1968; EP-A 141 317; EP-A 152 031; EP-A 226 917; EP-A 243 970; EP-A 256 503; EP-A 428 941; EP-A 532 022; EP-A 1 028 125; EP-A 1 035 122; EP-A 1 201 648; EP-A 1 122 244, JP 2002316902; DE 19650197; DE 10021412; DE 102005009458; U.S. Pat. Nos. 3,296, 272; 3,325,503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624, WO 10/139271, WO 11/028657, WO 12/168188, WO 07/006670, WO 11/77514; WO 13/047749, WO 10/069882, WO 13/047441, WO 03/16303, WO 09/90181, WO 13/007767, WO 13/010862, WO 13/127704, WO 13/024009, WO 13/24010, WO 13/047441, WO 13/162072, WO 13/092224, WO 11/135833, CN 1907024, CN 1456054, CN 103387541, CN 1309897, WO 12/84812, CN 1907024, WO 09094442, WO 14/60177, WO 13/116251, WO 08/013622, WO 15/65922, WO 94/01546, EP 2865265, WO 07/129454, WO 12/165511, WO 11/081174, WO 13/47441).

The present invention furthermore relates to agrochemical compositions comprising a mixture of at least one compound I (component 1) and at least one further active substance useful for plant protection, e. g. selected from the groups A) to O) (component 2), in particular one further fungicide, e. g. one or more fungicide from the groups A) to K), as described above, and if desired one suitable solvent or solid carrier. Those mixtures are of particular interest, since many of them at the same application rate show higher efficiencies against harmful fungi. Furthermore, combating harmful fungi with a mixture of compounds I and at least one fungicide from groups A) to K), as described above, is more efficient than combating those fungi with individual compounds I or individual fungicides from groups A) to K).

By applying compounds I together with at least one active substance from groups A) to O) a synergistic effect can be obtained, i.e. more then simple addition of the individual effects is obtained (synergistic mixtures).

This can be obtained by applying the compounds I and at least one further active substance simultaneously, either jointly (e. g. as tank-mix) or seperately, or in succession, wherein the time interval between the individual applications is selected to ensure that the active substance applied first still occurs at the site of action in a sufficient amount at the time of application of the further active substance(s). The order of application is not essential for working of the present invention.

When applying compound I and a pesticide II sequentially the time between both applications may vary e. g. between 2 hours to 7 days. Also a broader range is possible ranging from 0.25 hour to 30 days, preferably from 0.5 hour to 14 days, particularly from 1 hour to 7 days or from 1.5 hours to 5 days, even more preferred from 2 hours to 1 day.

In the binary mixtures and compositions according to the invention the weight ratio of the component 1) and the component 2) generally depends from the properties of the active components used, usually it is in the range of from 1:10,000 to 10,000:1, often it is in the range of from 1:100 to 100:1, regularly in the range of from 1:50 to 50:1, preferably in the range of from 1:20 to 20:1, more preferably in the range of from 1:10 to 10:1, even more preferably in the range of from 1:4 to 4:1 and in particular in the range of from 1:2 to 2:1.

According to further embodiments of the binary mixtures and compositions, the weight ratio of the component 1) and the component 2) usually is in the range of from 1000:1 to 1:1, often in the range of from 100:1 to 1:1, regularly in the range of from 50:1 to 1:1, preferably in the range of from 20:1 to 1:1, more preferably in the range of from 10:1 to 1:1, even more preferably in the range of from 4:1 to 1:1 and in particular in the range of from 2:1 to 1:1.

According to a further embodiments of the binary mixtures and compositions, the weight ratio of the component 1) and the component 2) usually is in the range of from 1:1 to 1:1000, often in the range of from 1:1 to 1:100, regularly in the range of from 1:1 to 1:50, preferably in the range of from 1:1 to 1:20, more preferably in the range of from 1:1 to 1:10, even more preferably in the range of from 1:1 to 1:4 and in particular in the range of from 1:1 to 1:2.

In the ternary mixtures, i.e. compositions according to the invention comprising the component 1) and component 2) and a compound III (component 3), the weight ratio of component 1) and component 2) depends from the properties of the active substances used, usually it is in the range of from 1:100 to 100:1, regularly in the range of from 1:50 to 50:1, preferably in the range of from 1:20 to 20:1, more preferably in the range of from 1:10 to 10:1 and in particular in the range of from 1:4 to 4:1, and the weight ratio of component 1) and component 3) usually it is in the range of from 1:100 to 100:1, regularly in the range of from 1:50 to 50:1, preferably in the range of from 1:20 to 20:1, more preferably in the range of from 1:10 to 10:1 and in particular in the range of from 1:4 to 4:1.

Any further active components are, if desired, added in a ratio of from 20:1 to 1:20 to the component 1).

These ratios are also suitable for inventive mixtures applied by seed treatment.

Preference is also given to mixtures comprising as component 2) at least one active substance selected from inhibitors of complex III at $Q_o$ site in group A), more preferably selected from compounds (A.1.1), (A.1.4), (A.1.8), (A.1.9), (A.1.10), (A.1.12), (A.1.13), (A.1.14), (A.1.17), (A.1.21), (A.1.24), (A.1.25), (A.1.26), (A.1.27), (A.1.30), (A.1.31), (A.1.32), (A.1.34) and (A.1.35); particularly selected from (A.1.1), (A.1.4), (A.1.8), (A.1.9), (A.1.13), (A.1.14), (A.1.17), (A.1.24), (A.1.25), (A.1.26), (A.1.27), (A.1.30), (A.1.31), (A.1.32), (A.1.34) and (A.1.35). Preference is also given to mixtures comprising as component 2) at least one active substance selected from inhibitors of complex III at $Q_i$ site in group A), more preferably selected from compounds (A.2.1), (A.2.3) and (A.2.4); particularly selected from (A.2.3) and (A.2.4).

Preference is also given to mixtures comprising as component 2) at least one active substance selected from inhibitors of complex II in group A), more preferably selected from compounds (A.3.2), (A.3.3), (A.3.4), (A.3.7), (A.3.9), (A.3.11), (A.3.12), (A.3.15), (A.3.16), (A.3.17), (A.3.18), (A.3.19), (A.3.20), (A.3.21), (A.3.22), (A.3.23), (A.3.24), (A.3.25), (A.3.27), (A.3.28), (A.3.29), (A.3.31), (A.3.32), (A.3.33), (A.3.34), (A.3.35), (A.3.36), (A.3.37), (A.3.38) and (A.3.39); particularly selected from (A.3.2), (A.3.3), (A.3.4), (A.3.7), (A.3.9), (A.3.12), (A.3.15), (A.3.17), (A.3.19), (A.3.22), (A.3.23), (A.3.24), (A.3.25), (A.3.27), (A.3.29), (A.3.31), (A.3.32), (A.3.33), (A.3.34), (A.3.35), (A.3.36), (A.3.37), (A.3.38) and (A.3.39).

Preference is also given to mixtures comprising as component 2) at least one active substance selected from other respiration nhibitors in group A), more preferably selected from compounds (A.4.5) and (A.4.11); in particular (A.4.11).

Preference is also given to mixtures comprising as component 2) at least one active substance selected from C14 demethylase inhibitors in group B), more preferably selected from compounds (B.1.4), (B.1.5), (B.1.8), (B.1.10), (B.1.11), (B.1.12), (B.1.13), (B.1.17), (B.1.18), (B.1.21), (B.1.22), (B.1.23), (B.1.25), (B.1.26), (B.1.29), (B.1.34), (B.1.37), (B.1.38), (B.1.43) and (B.1.46); particularly selected from (B.1.5), (B.1.8), (B.1.10), (B.1.17), (B.1.22), (B.1.23), (B.1.25), (B.1.33), (B.1.34), (B.1.37), (B.138), (B.1.43) and (B.1.46).

Preference is also given to mixtures comprising as component 2) at least one active substance selected from Delta14-reductase inhibitors in group B), more preferably selected from compounds (B.2.4), (B.2.5), (B.2.6) and (B.2.8); in particular (B.2.4).

Preference is also given to mixtures comprising as component 2) at least one active substance selected from phenylamides and acyl amino acid fungicides in group C), more preferably selected from compounds (C.1.1), (C.1.2), (C.1.4) and (C.1.5); particularly selected from (C.1.1) and (C.1.4).

Preference is also given to mixtures comprising as component 2) at least one active substance selected from other nucleic acid synthesis inhibitors in group C), more preferably selected from compounds (C.2.6), (C.2.7) and (C.2.8).

Preference is also given to mixtures comprising as component 2) at least one active substance selected from group D), more preferably selected from compounds (D.1.1), (D.1.2), (D.1.5), (D.2.4) and (D.2.6); particularly selected from (D.1.2), (D.1.5) and (D.2.6).

Preference is also given to mixtures comprising as component 2) at least one active substance selected from group E), more preferably selected from compounds (E.1.1), (E.1.3), (E.2.2) and (E.2.3); in particular (E.1.3).

Preference is also given to mixtures comprising as component 2) at least one active substance selected from group F), more preferably selected from compounds (F.1.2), (F.1.4) and (F.1.5).

Preference is also given to mixtures comprising as component 2) at least one active substance selected from group G), more preferably selected from compounds (G.3.1), (G.3.3), (G.3.6), (G.5.1), (G.5.2), (G.5.3), (G.5.4), (G.5.5), G.5.6), G.5.7), (G.5.8), (G.5.9), (G.5.10) and (G.5.11); particularly selected from (G.3.1), (G.5.1), (G.5.2) and (G.5.3).

Preference is also given to mixtures comprising as component 2) at least one active substance selected from group H), more preferably selected from compounds (H.2.2), (H.2.3), (H.2.5), (H.2.7), (H.2.8), (H.3.2), (H.3.4), (H.3.5), (H.4.9) and (H.4.10); particularly selected from (H.2.2), (H.2.5), (H.3.2), (H.4.9) and (H.4.10).

Preference is also given to mixtures comprising as component 2) at least one active substance selected from group I), more preferably selected from compounds (I.2.2) and (I.2.5).

Preference is also given to mixtures comprising as component 2) at least one active substance selected from group J), more preferably selected from compounds (J.1.2), (J.1.5) and (J.1.8); in particular (J.1.5).

Preference is also given to mixtures comprising as component 2) at least one active substance selected from group K), more preferably selected from compounds (K.1.41), (K.1.42), (K.1.44), (K.1.45), (K.1.47) and (K.1.49); particularly selected from (K.1.41), (K.1.44), (K.1.45), (K.1.47) and (K.1.49).

Accordingly, the present invention furthermore relates to mixtures comprising one compound of the formula I (component 1) and one pesticide II (component 2), wherein pesticide II is selected from the column "Co. 2" of the lines B-1 to B-727 of Table B.

A further embodiment relates to the mixtures B-1 to B-727 listed in Table B, where a row of Table B corresponds in each case to a fungicidal mixture comprising as active components one of the in the present specification individualized compounds of formula I, i.e. compounds I.A.A-1 to I.A.A-503, I.B.A-1 to I.B.A-503, I.C.A-1 to I.C.A-503, I.D.A-1 to I.D.A-503, I.E.A-1 to I.E.A-503, I.F.A-1 to I.F.A-503, I.G.A-1 to I.G.A-503, I.H.A-1 to I.H.A-503, I.I.A-1 to I.I.A-503 and I.J.A-1 to I.J.A-503 as defined in tables 1 to 11 (component 1 in column "Co.1") and the respective pesticide II from groups A) to O) (component 2) stated in the row in question.

Another embodiment relates to the mixtures B-1 to B-727 listed in Table B, where a row of Table B corresponds in each case to a fungicidal mixture comprising as active components one of the compounds Ex-1 to Ex-7 of formula I as defined below in table I (component 1 in column "Co.1") and the respective pesticide 11 from groups A) to O) (component 2) stated in the row in question.

Preferably, the compositions described in Table B comprise the active components in synergistically effective amounts.

TABLE B

Mixtures comprising as active components one indiviualized compound of the fomula I (in column Co. 1), and as component 2) (in column Co. 2) one pesticide from groups A) to O) [which is coded e.g. as (A.1.1) for azoxystrobin as defined above].

| Mixt. | Co. 1 | Co. 2 |
| --- | --- | --- |
| B-1 | (I) | (A.1.1) |
| B-2 | (I) | (A.1.2) |
| B-3 | (I) | (A.1.3) |
| B-4 | (I) | (A.1.4) |
| B-5 | (I) | (A.1.5) |
| B-6 | (I) | (A.1.6) |
| B-7 | (I) | (A.1.7) |
| B-8 | (I) | (A.1.8) |
| B-9 | (I) | (A.1.9) |
| B-10 | (I) | (A.1.10) |
| B-11 | (I) | (A.1.11) |
| B-12 | (I) | (A.1.12) |
| B-13 | (I) | (A.1.13) |
| B-14 | (I) | (A.1.14) |
| B-15 | (I) | (A.1.15) |

TABLE B-continued

Mixtures comprising as active components one indiviualized compound of the fomula I (in column Co. 1), and as component 2) (in column Co. 2) one pesticide from groups A) to O) [which is coded e.g. as (A.1.1) for azoxystrobin as defined above].

| Mixt. | Co. 1 | Co. 2 |
|---|---|---|
| B-16 | (I) | (A.1.16) |
| B-17 | (I) | (A.1.17) |
| B-18 | (I) | (A.1.18) |
| B-19 | (I) | (A.1.19) |
| B-20 | (I) | (A.1.20) |
| B-21 | (I) | (A.1.21) |
| B-22 | (I) | (A.1.22) |
| B-23 | (I) | (A.1.23) |
| B-24 | (I) | (A.1.24) |
| B-25 | (I) | (A.1.25) |
| B-26 | (I) | (A.1.26) |
| B-27 | (I) | (A.1.27) |
| B-28 | (I) | (A.1.30) |
| B-29 | (I) | (A.1.31) |
| B-30 | (I) | (A.1.32) |
| B-31 | (I) | (A.2.1) |
| B-32 | (I) | (A.2.2) |
| B-33 | (I) | (A.2.3) |
| B-34 | (I) | (A.2.4) |
| B-35 | (I) | (A.2.6) |
| B-36 | (I) | (A.2.7) |
| B-37 | (I) | (A.2.8) |
| B-38 | (I) | (A.3.1) |
| B-39 | (I) | (A.3.2) |
| B-40 | (I) | (A.3.3) |
| B-41 | (I) | (A.3.4) |
| B-42 | (I) | (A.3.5) |
| B-43 | (I) | (A.3.6) |
| B-44 | (I) | (A.3.7) |
| B-45 | (I) | (A.3.8) |
| B-46 | (I) | (A.3.9) |
| B-47 | (I) | (A.3.10) |
| B-48 | (I) | (A.3.11) |
| B-49 | (I) | (A.3.12) |
| B-50 | (I) | (A.3.13) |
| B-51 | (I) | (A.3.14) |
| B-52 | (I) | (A.3.15) |
| B-53 | (I) | (A.3.16) |
| B-54 | (I) | (A.3.17) |
| B-55 | (I) | (A.3.18) |
| B-56 | (I) | (A.3.19) |
| B-57 | (I) | (A.3.20) |
| B-58 | (I) | (A.3.21) |
| B-59 | (I) | (A.3.22) |
| B-60 | (I) | (A.3.23) |
| B-61 | (I) | (A.3.24) |
| B-62 | (I) | (A.3.25) |
| B-63 | (I) | (A.3.26) |
| B-64 | (I) | (A.3.27) |
| B-65 | (I) | (A.3.28) |
| B-66 | (I) | (A.3.29) |
| B-67 | (I) | (A.3.30) |
| B-68 | (I) | (A.3.31) |
| B-69 | (I) | (A.3.32) |
| B-70 | (I) | (A.3.33) |
| B-71 | (I) | (A.3.34) |
| B-72 | (I) | (A.3.35) |
| B-73 | (I) | (A.3.36) |
| B-74 | (I) | (A.3.37) |
| B-75 | (I) | (A.3.38) |
| B-76 | (I) | (A.3.39) |
| B-77 | (I) | (A.4.1) |
| B-78 | (I) | (A.4.2) |
| B-79 | (I) | (A.4.3) |
| B-80 | (I) | (A.4.4) |
| B-81 | (I) | (A.4.5) |
| B-82 | (I) | (A.4.6) |
| B-83 | (I) | (A.4.7) |
| B-84 | (I) | (A.4.8) |
| B-85 | (I) | (A.4.9) |
| B-86 | (I) | (A.4.10) |
| B-87 | (I) | (A.4.11) |
| B-88 | (I) | (A.4.12) |
| B-89 | (I) | (B.1.1) |
| B-90 | (I) | (B.1.2) |
| B-91 | (I) | (B.1.3) |
| B-92 | (I) | (B.1.4) |
| B-93 | (I) | (B.1.5) |
| B-94 | (I) | (B.1.6) |
| B-95 | (I) | (B.1.7) |
| B-96 | (I) | (B.1.8) |
| B-97 | (I) | (B.1.9) |
| B-98 | (I) | (B.1.10) |
| B-99 | (I) | (B.1.11) |
| B-100 | (I) | (B.1.12) |
| B-101 | (I) | (B.1.13) |
| B-102 | (I) | (B.1.14) |
| B-103 | (I) | (B.1.15) |
| B-104 | (I) | (B.1.16) |
| B-105 | (I) | (B.1.17) |
| B-106 | (I) | (B.1.18) |
| B-107 | (I) | (B.1.19) |
| B-108 | (I) | (B.1.20) |
| B-109 | (I) | (B.1.21) |
| B-110 | (I) | (B.1.22) |
| B-111 | (I) | (B.1.23) |
| B-112 | (I) | (B.1.24) |
| B-113 | (I) | (B.1.25) |
| B-114 | (I) | (B.1.26) |
| B-115 | (I) | (B.1.27) |
| B-116 | (I) | (B.1.28) |
| B-117 | (I) | (B.1.29) |
| B-118 | (I) | (B.1.30) |
| B-119 | (I) | (B.1.34) |
| B-120 | (I) | (B.1.37) |
| B-121 | (I) | (B.1.38) |
| B-122 | (I) | (B.1.43) |
| B-123 | (I) | (B.1.44) |
| B-124 | (I) | (B.1.45) |
| B-125 | (I) | (B.1.46) |
| B-126 | (I) | (B.1.47) |
| B-127 | (I) | (B.1.48) |
| B-128 | (I) | (B.1.49) |
| B-129 | (I) | (B.1.50) |
| B-130 | (I) | (B.1.51) |
| B-131 | (I) | (B.2.1) |
| B-132 | (I) | (B.2.2) |
| B-133 | (I) | (B.2.3) |
| B-134 | (I) | (B.2.4) |
| B-135 | (I) | (B.2.5) |
| B-136 | (I) | (B.2.6) |
| B-137 | (I) | (B.2.7) |
| B-138 | (I) | (B.2.8) |
| B-139 | (I) | (B.3.1) |
| B-140 | (I) | (C.1.1) |
| B-141 | (I) | (C.1.2) |
| B-142 | (I) | (C.1.3) |
| B-143 | (I) | (C.1.4) |
| B-144 | (I) | (C.1.5) |
| B-145 | (I) | (C.1.6) |
| B-146 | (I) | (C.1.7) |
| B-147 | (I) | (C.2.1) |
| B-148 | (I) | (C.2.2) |
| B-149 | (I) | (C.2.3) |
| B-150 | (I) | (C.2.4) |
| B-151 | (I) | (C.2.5) |
| B-152 | (I) | (C.2.6) |
| B-153 | (I) | (C.2.7) |
| B-154 | (I) | (D.1.1) |
| B-155 | (I) | (D.1.2) |
| B-156 | (I) | (D.1.3) |
| B-157 | (I) | (D.1.4) |
| B-158 | (I) | (D.1.5) |
| B-159 | (I) | (D.1.6) |
| B-160 | (I) | (D.2.1) |
| B-161 | (I) | (D.2.2) |

TABLE B-continued

Mixtures comprising as active components one indiviualized compound of the fomula I (in column Co. 1), and as component 2) (in column Co. 2) one pesticide from groups A) to O) [which is coded e.g. as (A.1.1) for azoxystrobin as defined above].

| Mixt. | Co. 1 | Co. 2 |
|---|---|---|
| B-162 | (I) | (D.2.3) |
| B-163 | (I) | (D.2.4) |
| B-164 | (I) | (D.2.5) |
| B-165 | (I) | (D.2.6) |
| B-166 | (I) | (D.2.7) |
| B-167 | (I) | (E.1.1) |
| B-168 | (I) | (E.1.2) |
| B-169 | (I) | (E.1.3) |
| B-170 | (I) | (E.2.1) |
| B-171 | (I) | (E.2.2) |
| B-172 | (I) | (E.2.3) |
| B-173 | (I) | (E.2.4) |
| B-174 | (I) | (E.2.5) |
| B-175 | (I) | (E.2.6) |
| B-176 | (I) | (E.2.7) |
| B-177 | (I) | (E.2.8) |
| B-178 | (I) | (F.1.1) |
| B-179 | (I) | (F.1.2) |
| B-180 | (I) | (F.1.3) |
| B-181 | (I) | (F.1.4) |
| B-182 | (I) | (F.1.5) |
| B-183 | (I) | (F.1.6) |
| B-184 | (I) | (F.2.1) |
| B-185 | (I) | (G.1.1) |
| B-186 | (I) | (G.1.2) |
| B-187 | (I) | (G.1.3) |
| B-188 | (I) | (G.1.4) |
| B-189 | (I) | (G.2.1) |
| B-190 | (I) | (G.2.2) |
| B-191 | (I) | (G.2.3) |
| B-192 | (I) | (G.2.4) |
| B-193 | (I) | (G.2.5) |
| B-194 | (I) | (G.2.6) |
| B-195 | (I) | (G.2.7) |
| B-196 | (I) | (G.3.1) |
| B-197 | (I) | (G.3.2) |
| B-198 | (I) | (G.3.3) |
| B-199 | (I) | (G.3.4) |
| B-200 | (I) | (G.3.5) |
| B-201 | (I) | (G.3.6) |
| B-202 | (I) | (G.3.7) |
| B-203 | (I) | (G.3.8) |
| B-204 | (I) | (G.4.1) |
| B-205 | (I) | (G.5.1) |
| B-206 | (I) | (G.5.2) |
| B-207 | (I) | (G.5.3) |
| B-208 | (I) | (H.1.1) |
| B-209 | (I) | (H.1.2) |
| B-210 | (I) | (H.1.3) |
| B-211 | (I) | (H.1.4) |
| B-212 | (I) | (H.1.5) |
| B-213 | (I) | (H.1.6) |
| B-214 | (I) | (H.2.1) |
| B-215 | (I) | (H.2.2) |
| B-216 | (I) | (H.2.3) |
| B-217 | (I) | (H.2.4) |
| B-218 | (I) | (H.2.5) |
| B-219 | (I) | (H.2.6) |
| B-220 | (I) | (H.2.7) |
| B-221 | (I) | (H.2.8) |
| B-222 | (I) | (H.2.9) |
| B-223 | (I) | (H.3.1) |
| B-224 | (I) | (H.3.2) |
| B-225 | (I) | (H.3.3) |
| B-226 | (I) | (H.3.4) |
| B-227 | (I) | (H.3.5) |
| B-228 | (I) | (H.3.6) |
| B-229 | (I) | (H.3.7) |
| B-230 | (I) | (H.3.8) |
| B-231 | (I) | (H.3.9) |
| B-232 | (I) | (H.3.10) |
| B-233 | (I) | (H.3.11) |
| B-234 | (I) | (H.4.1) |
| B-235 | (I) | (H.4.2) |
| B-236 | (I) | (H.4.3) |
| B-237 | (I) | (H.4.4) |
| B-238 | (I) | (H.4.5) |
| B-239 | (I) | (H.4.6) |
| B-240 | (I) | (H.4.7) |
| B-241 | (I) | (H.4.8) |
| B-242 | (I) | (H.4.9) |
| B-243 | (I) | (H.4.10) |
| B-244 | (I) | (I.1.1) |
| B-245 | (I) | (I.1.2) |
| B-246 | (I) | (I.2.1) |
| B-247 | (I) | (I.2.2) |
| B-248 | (I) | (I.2.3) |
| B-249 | (I) | (I.2.4) |
| B-250 | (I) | (I.2.5) |
| B-251 | (I) | (J.1.1) |
| B-252 | (I) | (J.1.2) |
| B-253 | (I) | (J.1.3) |
| B-254 | (I) | (J.1.4) |
| B-255 | (I) | (J.1.5) |
| B-256 | (I) | (J.1.6) |
| B-257 | (I) | (J.1.7) |
| B-258 | (I) | (J.1.8) |
| B-259 | (I) | (J.1.9) |
| B-260 | (I) | (J.1.10) |
| B-261 | (I) | (K.1.1) |
| B-262 | (I) | (K.1.2) |
| B-263 | (I) | (K.1.3) |
| B-264 | (I) | (K.1.4) |
| B-265 | (I) | (K.1.5) |
| B-266 | (I) | (K.1.6) |
| B-267 | (I) | (K.1.7) |
| B-268 | (I) | (K.1.8) |
| B-269 | (I) | (K.1.9) |
| B-270 | (I) | (K.1.10) |
| B-271 | (I) | (K.1.11) |
| B-272 | (I) | (K.1.12) |
| B-273 | (I) | (K.1.13) |
| B-274 | (I) | (K.1.14) |
| B-275 | (I) | (K.1.15) |
| B-276 | (I) | (K.1.16) |
| B-277 | (I) | (K.1.17) |
| B-278 | (I) | (K.1.18) |
| B-279 | (I) | (K.1.19) |
| B-280 | (I) | (K.1.20) |
| B-281 | (I) | (K.1.21) |
| B-282 | (I) | (K.1.22) |
| B-283 | (I) | (K.1.23) |
| B-284 | (I) | (K.1.24) |
| B-285 | (I) | (K.1.25) |
| B-286 | (I) | (K.1.26) |
| B-287 | (I) | (K.1.27) |
| B-288 | (I) | (K.1.28) |
| B-289 | (I) | (K.1.29) |
| B-290 | (I) | (K.1.30) |
| B-291 | (I) | (K.1.31) |
| B-292 | (I) | (K.1.32) |
| B-293 | (I) | (K.1.33) |
| B-294 | (I) | (K.1.34) |
| B-295 | (I) | (K.1.35) |
| B-296 | (I) | (K.1.36) |
| B-297 | (I) | (K.1.37) |
| B-298 | (I) | (K.1.38) |
| B-299 | (I) | (K.1.39) |
| B-300 | (I) | (K.1.40) |
| B-301 | (I) | (K.1.41) |
| B-302 | (I) | (K.1.42) |
| B-303 | (I) | (K.1.43) |
| B-304 | (I) | (K.1.44) |
| B-305 | (I) | (K.1.45) |
| B-306 | (I) | (K.1.47) |
| B-307 | (I) | (M.1.1) |

TABLE B-continued

Mixtures comprising as active components one indiviualized compound of the fomula I (in column Co. 1), and as component 2) (in column Co. 2) one pesticide from groups A) to O) [which is coded e.g. as (A.1.1) for azoxystrobin as defined above].

| Mixt. | Co. 1 | Co. 2 |
|---|---|---|
| B-308 | (I) | (M.1.2) |
| B-309 | (I) | (M.1.3) |
| B-310 | (I) | (M.1.4) |
| B-311 | (I) | (M.1.5) |
| B-312 | (I) | (M.1.6) |
| B-313 | (I) | (M.1.7) |
| B-314 | (I) | (M.1.8) |
| B-315 | (I) | (M.1.9) |
| B-316 | (I) | (M.1.10) |
| B-317 | (I) | (M.1.11) |
| B-318 | (I) | (M.1.12) |
| B-319 | (I) | (M.1.13) |
| B-320 | (I) | (M.1.14) |
| B-321 | (I) | (M.1.15) |
| B-322 | (I) | (M.1.16) |
| B-323 | (I) | (M.1.17) |
| B-324 | (I) | (M.1.18) |
| B-325 | (I) | (M.1.19) |
| B-326 | (I) | (M.1.20) |
| B-327 | (I) | (M.1.21) |
| B-328 | (I) | (M.1.22) |
| B-329 | (I) | (M.1.23) |
| B-330 | (I) | (M.1.24) |
| B-331 | (I) | (M.1.25) |
| B-332 | (I) | (M.1.26) |
| B-333 | (I) | (M.1.27) |
| B-334 | (I) | (M.1.28) |
| B-335 | (I) | (M.1.29) |
| B-336 | (I) | (M.1.30) |
| B-337 | (I) | (M.1.31) |
| B-338 | (I) | (M.1.32) |
| B-339 | (I) | (M.1.33) |
| B-340 | (I) | (M.1.34) |
| B-341 | (I) | (M.1.35) |
| B-342 | (I) | (M.1.36) |
| B-343 | (I) | (M.1.37) |
| B-344 | (I) | (M.1.38) |
| B-345 | (I) | (M.1.39) |
| B-346 | (I) | (M.1.40) |
| B-347 | (I) | (M.1.41) |
| B-348 | (I) | (M.1.42) |
| B-349 | (I) | (M.1.43) |
| B-350 | (I) | (M.1.44) |
| B-351 | (I) | (M.1.45) |
| B-352 | (I) | (M.1.46) |
| B-353 | (I) | (M.1.47) |
| B-354 | (I) | (M.1.48) |
| B-355 | (I) | (M.1.49) |
| B-356 | (I) | (M.1.50) |
| B-357 | (I) | (N.1.1) |
| B-358 | (I) | (N.1.2) |
| B-359 | (I) | (N.1.3) |
| B-360 | (I) | (N.1.4) |
| B-361 | (I) | (N.1.5) |
| B-362 | (I) | (N.2.1) |
| B-363 | (I) | (N.2.2) |
| B-364 | (I) | (N.2.3) |
| B-365 | (I) | (N.3.1) |
| B-366 | (I) | (N.3.2) |
| B-367 | (I) | (N.3.3) |
| B-368 | (I) | (N.3.4) |
| B-369 | (I) | (N.4.1) |
| B-370 | (I) | (N.5.1) |
| B-371 | (I) | (N.6.1) |
| B-372 | (I) | (N.6.2) |
| B-373 | (I) | (N.6.3) |
| B-374 | (I) | (N.6.4) |
| B-375 | (I) | (N.6.5) |
| B-376 | (I) | (N.7.1) |
| B-377 | (I) | (N.7.2) |
| B-378 | (I) | (N.7.3) |
| B-379 | (I) | (N.8.1) |
| B-380 | (I) | (N.9.1) |
| B-381 | (I) | (N.10.1) |
| B-382 | (I) | (N.10.2) |
| B-383 | (I) | (N.10.3) |
| B-384 | (I) | (N.10.4) |
| B-385 | (I) | (N.10.5) |
| B-386 | (I) | (N.11.1) |
| B-387 | (I) | (N.12.1) |
| B-388 | (I) | (N.12.2) |
| B-389 | (I) | (N.12.3) |
| B-390 | (I) | (N.12.4) |
| B-391 | (I) | (N.13.1) |
| B-392 | (I) | (N.13.2) |
| B-393 | (I) | (N.13.3) |
| B-394 | (I) | (N.13.4) |
| B-395 | (I) | (N.13.5) |
| B-396 | (I) | (N.13.6) |
| B-397 | (I) | (N.13.7) |
| B-398 | (I) | (N.13.8) |
| B-399 | (I) | (N.13.9) |
| B-400 | (I) | (N.14.1) |
| B-401 | (I) | (N.14.2) |
| B-402 | (I) | (N.14.3) |
| B-403 | (I) | (N.15.1) |
| B-404 | (I) | (N.16.1) |
| B-405 | (I) | (N.16.2) |
| B-406 | (I) | (N.17.1) |
| B-407 | (I) | (N.17.2) |
| B-408 | (I) | (N.17.3) |
| B-409 | (I) | (N.17.4) |
| B-410 | (I) | (N.17.5) |
| B-411 | (I) | (N.17.6) |
| B-412 | (I) | (N.17.7) |
| B-413 | (I) | (N.17.8) |
| B-414 | (I) | (N.17.9) |
| B-415 | (I) | (N.17.10) |
| B-416 | (I) | (N.17.11) |
| B-417 | (I) | (N.17.12) |
| B-418 | (I) | (O.1.1) |
| B-419 | (I) | (O.1.2) |
| B-420 | (I) | (O.1.3) |
| B-421 | (I) | (O.1.4) |
| B-422 | (I) | (O.1.5) |
| B-423 | (I) | (O.1.6) |
| B-424 | (I) | (O.1.7) |
| B-425 | (I) | (O.1.8) |
| B-426 | (I) | (O.1.9) |
| B-427 | (I) | (O.1.10) |
| B-428 | (I) | (O.1.11) |
| B-429 | (I) | (O.1.12) |
| B-430 | (I) | (O.1.13) |
| B-431 | (I) | (O.1.14) |
| B-432 | (I) | (O.1.15) |
| B-433 | (I) | (O.1.16) |
| B-434 | (I) | (O.1.17) |
| B-435 | (I) | (O.1.18) |
| B-436 | (I) | (O.1.19) |
| B-437 | (I) | (O.1.20) |
| B-438 | (I) | (O.1.21) |
| B-439 | (I) | (O.1.22) |
| B-440 | (I) | (O.1.23) |
| B-441 | (I) | (O.1.24) |
| B-442 | (I) | (O.1.25) |
| B-443 | (I) | (O.1.26) |
| B-444 | (I) | (O.1.27) |
| B-445 | (I) | (O.1.28) |
| B-446 | (I) | (O.1.29) |
| B-447 | (I) | (O.1.30) |
| B-448 | (I) | (O.1.31) |
| B-449 | (I) | (O.1.32) |
| B-450 | (I) | (O.1.33) |
| B-451 | (I) | (O.1.34) |
| B-452 | (I) | (O.1.35) |
| B-453 | (I) | (O.1.36) |

TABLE B-continued

Mixtures comprising as active components one indiviualized compound of the fomula I (in column Co. 1), and as component 2) (in column Co. 2) one pesticide from groups A) to O) [which is coded e.g. as (A.1.1) for azoxystrobin as defined above].

| Mixt. | Co. 1 | Co. 2 |
|---|---|---|
| B-454 | (I) | (O.1.37) |
| B-455 | (I) | (O.1.38) |
| B-456 | (I) | (O.2.1) |
| B-457 | (I) | (O.2.2) |
| B-458 | (I) | (O.2.3) |
| B-459 | (I) | (O.2.4) |
| B-460 | (I) | (O.2.5) |
| B-461 | (I) | (O.2.6) |
| B-462 | (I) | (O.2.7) |
| B-463 | (I) | (O.2.8) |
| B-464 | (I) | (O.2.9) |
| B-465 | (I) | (O.2.10) |
| B-466 | (I) | (O.2.11) |
| B-467 | (I) | (O.2.12) |
| B-468 | (I) | (O.2.13) |
| B-469 | (I) | (O.2.14) |
| B-470 | (I) | (O.2.15) |
| B-471 | (I) | (O.2.16) |
| B-472 | (I) | (O.3.1) |
| B-473 | (I) | (O.3.2) |
| B-474 | (I) | (O.3.3) |
| B-475 | (I) | (O.3.4) |
| B-476 | (I) | (O.3.5) |
| B-477 | (I) | (O.3.6) |
| B-478 | (I) | (O.3.7) |
| B-479 | (I) | (O.3.8) |
| B-480 | (I) | (O.3.9) |
| B-481 | (I) | (O.3.10) |
| B-482 | (I) | (O.3.11) |
| B-483 | (I) | (O.3.12) |
| B-484 | (I) | (O.3.13) |
| B-485 | (I) | (O.3.14) |
| B-486 | (I) | (O.3.15) |
| B-487 | (I) | (O.3.16) |
| B-488 | (I) | (O.3.17) |
| B-489 | (I) | (O.3.18) |
| B-490 | (I) | (O.3.19) |
| B-491 | (I) | (O.3.20) |
| B-492 | (I) | (O.3.21) |
| B-493 | (I) | (O.3.22) |
| B-494 | (I) | (O.3.23) |
| B-495 | (I) | (O.3.24) |
| B-496 | (I) | (O.3.25) |
| B-497 | (I) | (O.3.26) |
| B-498 | (I) | (O.3.27) |
| B-499 | (I) | (O.4.1) |
| B-500 | (I) | (O.4.2) |
| B-501 | (I) | (O.4.3) |
| B-502 | (I) | (O.4.4) |
| B-503 | (I) | (O.4.5) |
| B-504 | (I) | (O.4.6) |
| B-505 | (I) | (O.4.7) |
| B-506 | (I) | (O.4.8) |
| B-507 | (I) | (O.4.9) |
| B-508 | (I) | (O.4.10) |
| B-509 | (I) | (O.4.11) |
| B-510 | (I) | (O.4.12) |
| B-511 | (I) | (O.4.13) |
| B-512 | (I) | (O.4.14) |
| B-513 | (I) | (O.4.15) |
| B-514 | (I) | (O.4.16) |
| B-515 | (I) | (O.4.17) |
| B-516 | (I) | (O.4.18) |
| B-517 | (I) | (O.4.19) |
| B-518 | (I) | (O.4.20) |
| B-519 | (I) | (O.4.21) |
| B-520 | (I) | (O.4.22) |
| B-521 | (I) | (O.4.23) |
| B-522 | (I) | (O.4.24) |
| B-523 | (I) | (O.5.1) |
| B-524 | (I) | (O.5.2) |
| B-525 | (I) | (O.5.3) |
| B-526 | (I) | (O.5.4) |
| B-527 | (I) | (O.5.5) |
| B-528 | (I) | (O.5.6) |
| B-529 | (I) | (O.5.7) |
| B-530 | (I) | (O.5.8) |
| B-531 | (I) | (O.5.9) |
| B-532 | (I) | (O.6.1) |
| B-533 | (I) | (O.6.2) |
| B-534 | (I) | (O.6.3) |
| B-535 | (I) | (O.6.4) |
| B-536 | (I) | (O.6.5) |
| B-537 | (I) | (O.6.6) |
| B-538 | (I) | (O.6.7) |
| B-539 | (I) | (O.7.1) |
| B-540 | (I) | (O.7.2) |
| B-541 | (I) | (O.7.3) |
| B-542 | (I) | (O.7.4) |
| B-543 | (I) | (O.7.5) |
| B-544 | (I) | (O.7.6) |
| B-545 | (I) | (O.8.1) |
| B-546 | (I) | (O.8.2) |
| B-547 | (I) | (O.8.3) |
| B-548 | (I) | (O.8.4) |
| B-549 | (I) | (O.8.5) |
| B-550 | (I) | (O.9.1) |
| B-551 | (I) | (O.9.2) |
| B-552 | (I) | (O.9.3) |
| B-553 | (I) | (O.10.1) |
| B-554 | (I) | (O.11.1) |
| B-555 | (I) | (O.11.2) |
| B-556 | (I) | (O.11.3) |
| B-557 | (I) | (O.11.4) |
| B-558 | (I) | (O.12.1) |
| B-559 | (I) | (O.13.1) |
| B-560 | (I) | (O.14.1) |
| B-561 | (I) | (O.14.2) |
| B-562 | (I) | (O.15.1) |
| B-563 | (I) | (O.15.2) |
| B-564 | (I) | (O.15.3) |
| B-565 | (I) | (O.15.4) |
| B-566 | (I) | (O.15.5) |
| B-567 | (I) | (O.15.6) |
| B-568 | (I) | (O.15.7) |
| B-569 | (I) | (O.15.8) |
| B-570 | (I) | (O.15.9) |
| B-571 | (I) | (O.15.10) |
| B-572 | (I) | (O.15.11) |
| B-573 | (I) | (O.16.1) |
| B-574 | (I) | (O.16.2) |
| B-575 | (I) | (O.16.3) |
| B-576 | (I) | (O.16.4) |
| B-577 | (I) | (O.16.5) |
| B-578 | (I) | (O.16.6) |
| B-579 | (I) | (O.17.1) |
| B-580 | (I) | (O.18.1) |
| B-581 | (I) | (O.18.2) |
| B-582 | (I) | (O.18.3) |
| B-583 | (I) | (O.18.4) |
| B-584 | (I) | (O.18.5) |
| B-585 | (I) | (O.19.1) |
| B-586 | (I) | (O.20.1) |
| B-587 | (I) | (O.20.2) |
| B-588 | (I) | (O.20.3) |
| B-589 | (I) | (O.21.1) |
| B-590 | (I) | (O.21.2) |
| B-591 | (I) | (O.21.3) |
| B-592 | (I) | (O.21.4) |
| B-593 | (I) | (O.21.5) |
| B-594 | (I) | (O.21.6) |
| B-595 | (I) | (O.21.7) |
| B-596 | (I) | (O.22.1) |
| B-597 | (I) | (O.22.2) |
| B-598 | (I) | (O.22.3) |
| B-599 | (I) | (O.22.4) |

TABLE B-continued

Mixtures comprising as active components one indiviualized compound of the fomula I (in column Co. 1), and as component 2) (in column Co. 2) one pesticide from groups A) to O) [which is coded e.g. as (A.1.1) for azoxystrobin as defined above].

| Mixt. | Co. 1 | Co. 2 |
|---|---|---|
| B-600 | (I) | (O.23.1) |
| B-601 | (I) | (O.23.2) |
| B-602 | (I) | (O.23.3) |
| B-603 | (I) | (O.24.1) |
| B-604 | (I) | (O.24.2) |
| B-605 | (I) | (O.24.3) |
| B-606 | (I) | (O.24.4) |
| B-607 | (I) | (O.24.5) |
| B-608 | (I) | (O.25.1) |
| B-609 | (I) | (O.25.2) |
| B-610 | (I) | (O.26.1) |
| B-611 | (I) | (O.26.2) |
| B-612 | (I) | (O.26.3) |
| B-613 | (I) | (O.26.4) |
| B-614 | (I) | (O.26.5) |
| B-615 | (I) | (O.26.6) |
| B-616 | (I) | (O.26.7) |
| B-617 | (I) | (O.26.8) |
| B-618 | (I) | (O.26.9) |
| B-619 | (I) | (O.26.10) |
| B-620 | (I) | (O.26.11) |
| B-621 | (I) | (O.26.12) |
| B-622 | (I) | (O.26.13) |
| B-623 | (I) | (O.26.14) |
| B-624 | (I) | (O.26.15) |
| B-625 | (I) | (O.26.16) |
| B-626 | (I) | (O.26.17) |
| B-627 | (I) | (O.26.18) |
| B-628 | (I) | (O.27.1) |
| B-629 | (I) | (O.27.2) |
| B-630 | (I) | (O.27.3) |
| B-631 | (I) | (O.27.4) |
| B-632 | (I) | (O.27.5) |
| B-633 | (I) | (O.27.6) |
| B-634 | (I) | (O.27.7) |
| B-635 | (I) | (O.27.8) |
| B-636 | (I) | (O.27.9) |
| B-637 | (I) | (O.27.10) |
| B-638 | (I) | (O.27.11) |
| B-639 | (I) | (O.27.12) |
| B-640 | (I) | (O.27.13) |
| B-641 | (I) | (O.27.14) |
| B-642 | (I) | (O.27.15) |
| B-643 | (I) | (O.27.16) |
| B-644 | (I) | (O.27.17) |
| B-645 | (I) | (O.27.18) |
| B-646 | (I) | (O.27.19) |
| B-647 | (I) | (O.27.20) |
| B-648 | (I) | (O.27.21) |
| B-649 | (I) | (O.27.22) |
| B-650 | (I) | (O.27.23) |
| B-651 | (I) | (O.27.24) |
| B-652 | (I) | (O.27.25) |
| B-653 | (I) | (O.27.26) |
| B-654 | (I) | (O.27.27) |
| B-655 | (I) | (O.27.28) |
| B-656 | (I) | (O.27.29) |
| B-657 | (I) | (O.27.30) |
| B-658 | (I) | (O.27.31) |
| B-659 | (I) | (O.27.32) |
| B-660 | (I) | (O.27.33) |
| B-661 | (I) | (O.27.34) |
| B-662 | (I) | (O.27.35) |
| B-663 | (I) | (O.27.36) |
| B-664 | (I) | (O.27.37) |
| B-665 | (I) | (O.27.38) |
| B-666 | (I) | (O.27.39) |
| B-667 | (I) | (O.27.40) |
| B-668 | (I) | (O.27.41) |
| B-669 | (I) | (O.27.42) |
| B-670 | (I) | (O.27.43) |
| B-671 | (I) | (O.27.44) |
| B-672 | (I) | (O.27.45) |
| B-673 | (I) | (O.27.46) |
| B-674 | (I) | (O.27.47) |
| B-675 | (I) | (O.27.48) |
| B-676 | (I) | (O.27.49) |
| B-677 | (I) | (O.27.50) |
| B-678 | (I) | (O.27.51) |
| B-679 | (I) | (O.27.52) |
| B-680 | (I) | (O.27.53) |
| B-681 | (I) | (O.27.54) |
| B-682 | (I) | (O.27.55) |
| B-683 | (I) | (O.27.56) |
| B-684 | (I) | (O.27.57) |
| B-685 | (I) | (O.27.58) |
| B-686 | (I) | (O.27.59) |
| B-687 | (I) | (O.27.60) |
| B-688 | (I) | (O.27.61) |
| B-689 | (I) | (O.27.62) |
| B-690 | (I) | (O.27.63) |
| B-691 | (I) | (O.27.64) |
| B-692 | (I) | (O.27.65) |
| B-693 | (I) | (O.27.66) |
| B-694 | (I) | (O.27.67) |
| B-695 | (I) | (O.27.68) |
| B-696 | (I) | (O.27.69) |
| B-697 | (I) | (O.27.70) |
| B-698 | (I) | (O.27.71) |
| B-699 | (I) | (O.27.72) |
| B-700 | (I) | (O.27.73) |
| B-701 | (I) | (O.27.74) |
| B-702 | (I) | (O.27.75) |
| B-703 | (I) | (O.27.76) |
| B-704 | (I) | (O.27.77) |
| B-705 | (I) | (O.27.78) |
| B-706 | (I) | (O.27.79) |
| B-707 | (I) | (O.27.80) |
| B-708 | (I) | (O.27.81) |
| B-709 | (I) | (O.27.82) |
| B-710 | (I) | (O.27.83) |
| B-711 | (I) | (O.27.84) |
| B-712 | (I) | (O.27.85) |
| B-713 | (I) | (O.27.86) |
| B-714 | (I) | (O.27.87) |
| B-715 | (I) | (O.27.88) |
| B-716 | (I) | (O.27.89) |
| B-717 | (I) | (O.27.90) |
| B-718 | (I) | (O.27.91) |
| B-719 | (I) | (O.27.92) |
| B-720 | (I) | (O.27.93) |
| B-721 | (I) | (O.27.94) |
| B-722 | (I) | (O.27.95) |
| B-723 | (I) | (O.27.96) |
| B-724 | (I) | (O.27.97) |
| B-725 | (I) | (O.27.98) |
| B-726 | (I) | (O.27.99) |
| B-727 | (I) | (O.27.100) |

The mixtures of active substances can be prepared as compositions comprising besides the active ingredients at least one inert ingredient (auxiliary) by usual means, e. g. by the means given for the compositions of compounds I. Concerning usual ingredients of such compositions reference is made to the explanations given for the compositions containing compounds I. The mixtures of active substances according to the present invention are suitable as fungicides, as are the compounds of formula I. They are distinguished by an outstanding effectiveness against a broad spectrum of phytopathogenic fungi, especially from the classes of the *Ascomycetes, Basidiomycetes, Deuteromycetes* and Peronosporomycetes (syn. *Oomycetes*). In addition, it is refered to the explanations regarding the fungicidal activity of the compounds and the compositions containing compounds I, respectively.

I. SYNTHESIS EXAMPLES

The compounds of formula I can be prepared according to the methods outlined below.

I.1) Preparation of N'-hydroxy-4-[1-(methylamino)ethyl]benzamidine

To a solution of 4-[1-(methylamino)ethyl]benzonitrile (13 g, 1 eq.) in ethanol (150 mL) was added triethylamine (17.4 g, 2.5 eq.) and hydroxyl amine (9.5 g, 2 eq.). The mixture was refluxed for 3 hours and concentrated under reduced pressure. The crude product (13 g) was used directly without further purification.

I.2) Preparation N-methyl-1-[4-[5-(trifluoromethyl)-1,2,4-oxadiazol-3-yl]phenyl]ethanamine A solution of N'-hydroxy-4-[1-(methylamino)ethyl]benzamidine as obtained in step 1.1 (35 g, 1.0 eq.) in dichloromethane (400 mL) was treated with trifluoroacetic anhydride (97 g, 3 eq.) at room temperature. The mixture was stirred for 1 hour, before it was washed with a saturated aqueous solutions of sodium bicarbonate and water. The organic layer was dried over sodium sulfate and concentrated under reduced pressure. The crude product (48 g) was that was used directly without further purification.

I.3) Preparation N-methyl-N-[1-[4-[5-(trifluoromethyl)-1,2,4-oxadiazol-3-yl]phenyl] ethyl]acetamide (Ex-16)

To a solution of N-methyl-1-[4-[5-(trifluoromethyl)-1,2,4-oxadiazol-3-yl]phenyl] ethanamine obtained in step 1.2 (8.5 g, 1 eq.) in dichloromethane (100 mL) was added triethylamine (5.9 g, 2.2 eq.) and acetyl chloride (2.3 g, 1.1 eq.). The mixture was stirred overnight, before it was diluted with dichloromethane and washed with aqueous 1N hydrochloric acid. The organic layer was successively washed with a saturated aqueous solution of sodium chloride, dried over sodium sulfate and freed from solvent under reduced pressure. Flash chromatography on silica gel using cyclohexane-ethyl acetate provided the titled product (4.95 g).

$^1$H NMR (CDCl$_3$): δ [ppm]=1.5 and 1.65 (d, 3H), 2.15 and 2.25 (s, 3H), 2.7 (s, 3H), 5.25 and 6.15 (q, 1H), 7.45 (m, 2H), 8.13 (m, 2H).

I.4) Preparation of N-[[4-[(Z)—N'-hydroxycarbamimidoyl]phenyl]methyl]-N,2-dimethyl-propanamide To a solution of N-[(4-cyanophenyl)methyl]-N-methyl-acetamide (8.8 g, 1.0 eq.) in tetrahydrofuran (50 mL) was added hydroxylamine hydrochloride (4.2 g, 1.5 eq.) and potassium carbonate (4.5 g, 0.8 eq.) in 20 mL water. The mixture was stirred overnight at 23° C. and the progress of the reaction was monitored by HPLC. It was filtered, washed five times with toluene and concentrated under reduced pressure to afford the title compound (10 g) that was used directly without further purification.

I.5) Preparation of N,2-dimethyl-N[[4-[5-(trifluoromethyl)-1,2,4-oxadiazol-3-yl] phenyl] methyl]propanamide (Ex-13)

A solution of N-[[4-[(Z)—N'-hydroxycarbamimidoyl]phenyl]methyl]-N,2-dimethyl-propanamide obtained in step I.4 (10 g, 1.0 eq.) in tetrahydrofuran (100 mL) was treated with trifluoroacetic anhydride (30 g, 3.5 eq.) at room temperature. The mixture was stirred for 2 hours, concentrated under reduced pressure and water was added. The aqueous phase was extracted with ethyl acetate, the combined organic phases were washed with aqueous 1N hydrochloric acid and saturated aqueous solution of sodium bicarbonate. The organic layer was dried over sodium sulfate and concentrated under reduced pressure. The crude product was dissolved in dichloromethane and washed with saturated aqueous solution of sodium bicarbonate to remove trifluoroacetic acid, and concentrated under reduced pressure to afford the titled product (3 g). Melting point: 55° C.

I.6) Preparation of N'-hydroxy-4-[(2-oxopyrrolidin-1-yl)methyl]benzamidine

To a solution of 4-[(2-oxopyrrolidin-1-yl)methyl]benzonitrile (0.55 g, 1.0 eq.) in ethanol (5 mL) was added hydroxylamine hydrochloride (0.382 g, 2 eq.) and triethylamine (0.694 g, 2.5 eq.). The mixture was refluxed for 4 hours and concentrated under reduced pressure to afford the title compound that was used directly without further purification.

I.7) Preparation of 1-[[4-[5-(trifluoromethyl)-1,2,4-oxadiazol-3-yl]phenyl]methyl] pyrrolidin-2-one (Ex-30)

A solution of N'-hydroxy-4-[(2-oxopyrrolidin-1-yl)methyl]benzamidine obtained in step 1.5 (1 g, 1.0 eq.) in dichloromethan (5 mL) was treated with trifluoroacetic anhydride (4.5 g, 5 eq.) at room temperature. The mixture was stirred for 2 hours at 23° C., washed with saturated aqueous solution of sodium bicarbonate and water. The organic layer was dried over sodium sulfate and concentrated under reduced pressure. Flash chromatography on silica gel using cyclohexane-ethyl acetate provided the titled product (80 mg). $^1$H NMR (CDCl$_3$): δ [ppm]=2.1 (m, 2H), 2.45 (m, 2H), 3.3 (m, 3H), 4.5 (s, 2H), 7.4 (m, 2H), 8.13 (m, 2H).

The compounds Ex-1 to Ex-34 listed in Table I were prepared in an analogous manner.

TABLE I

Compounds Ex-1 to Ex-34 of formula I.Ex, wherein A corresponds to subformula (A.4), wherein A is unsubstituted, and wherein the meaning of $R^1$, $R^2$, $R^3$ and $R^4$ are as defined in each line, and wherein # denotes the point of attachment of the $NR^1R^2$ group to the $CR^3R^4$ moiety.

| Ex. no | $R^3$ | $R^4$ | $R^1$ | $R^2$ | HPLC $R_t$*/ (M + H); or Melting point (° C.) |
|---|---|---|---|---|---|
| Ex-1 | CF$_3$ | H | CH$_3$ | H | 0.94/326 |
| Ex-2 | CF$_3$ | H | cyclopropyl | H | 1.28/352 |
| Ex-3 | H | H | CH$_3$ | C(=O)—CH$_3$ | 1.09/300 |
| Ex-4 | H | H | allyl | C(=O)—CH$_3$ | 1.17/326 |
| Ex-5 | H | H | allyl | C(=O)—CH$_2$CH$_3$ | 1.24/340 |
| Ex-6 | H | H | allyl | C(=O)—C(CH$_3$)$_3$ | 1.34/368 |
| Ex-7 | H | H | CH$_3$ | C(=O)—CH$_2$CH$_3$ | 1.16/314 |
| Ex-8 | H | H | CH$_3$ | C(=O)—C(CH$_3$)$_3$ | 1.29/342 |
| Ex-9 | H | H | CH(CH$_3$)$_2$ | C(=O)—CH$_2$CH$_3$ | 1.26/342 |
| Ex-10 | H | H | CH(CH$_3$)$_2$ | C(=O)—C(CH$_3$)$_3$ | 1.38/370 |
| Ex-11 | H | H | CH$_3$ | C(=O)—CH(CH$_2$CH$_3$)$_2$ | 1.26/356 |
| Ex-12 | H | H | CH$_3$ | C(=O)—CH$_2$CH$_2$CH$_3$ | 1.174/328 |
| Ex-13 | H | H | CH$_3$ | C(=O)—CH(CH$_3$)$_2$ | 1.170/328 |
| Ex-14 | H | H | CH$_3$ | C(=O)—CHCH$_3$CH$_2$CH$_3$ | 1.21/342 |
| Ex-15 | H | H | H | C(=O)—CH$_3$ | 132° C. |
| Ex-16 | CH$_3$ | H | CH$_3$ | C(=O)—CH$_3$ | 1.11/314 |
| Ex-17 | CH$_3$ | H | CH$_3$ | C(=O)—C(CH$_3$)$_3$ | 1.36/356 |
| Ex-18 | CH$_3$ | H | CH$_3$ | C(=O)—CH$_2$CH$_3$ | 1.20/327 |
| Ex-19 | CH$_3$ | H | CH$_3$ | C(=O)—CH$_2$CH$_2$CH$_3$ | 1.24/341 |
| Ex-20 | CH$_3$ | H | CH$_3$ | C(=O)—CH(CH$_2$CH$_3$)$_2$ | 1.36/369 |
| Ex-21 | CH$_3$ | H | CH$_3$ | C(=O)—CH(CH$_3$)$_2$ | 1.24/341 |
| Ex-22 | CH$_3$ | H | CH$_3$ | C(=O)—CHCH$_3$CH$_2$CH$_3$ | 1.30/355 |

TABLE I-continued

Compounds Ex-1 to Ex-34 of formula I.Ex, wherein A corresponds to subformula (A.4), wherein A is unsubstituted, and wherein the meaning of $R^1$, $R^2$, $R^3$ and $R^4$ are as defined in each line, and wherein # denotes the point of attachment of the $NR^1R^2$ group to the $CR^3R^4$ moiety.

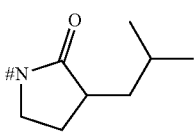

I.Ex

| Ex. no | $R^3$ | $R^4$ | $R^1$ | $R^2$ | HPLC $R_t$*/ (M + H); or Melting point (° C.) |
|---|---|---|---|---|---|
| Ex-23 | $CF_3$ | H | H | C(=O)—$CH_3$ | 191° C. |
| Ex-24 | H | H | $CH_2CH_3$ | C(=O)—CH($CH_3$)$_2$ | 1.32/341 |
| Ex-25 | H | H | $CH_2CH_3$ | C(=O)—$CH_2CH_2CH_3$ | 1.24/341 |
| Ex-26 | H | H | $CH_2CH_3$ | C(=O)—$CH_2CH_3$ | 1.31/327 |
| Ex-27 | H | H | $CH_2CH_3$ | C(=O)—C($CH_3$)$_3$ | 1.32/355 |
| Ex-28 | H | H | $CH_2CH_3$ | C(=O)—CH$CH_3CH_2CH_3$ | 1.29/355 |
| Ex-29 | H | H | 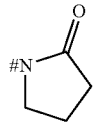 | | 1.31/367 |
| Ex-30 | H | H | 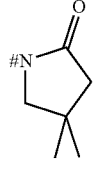 | | 1.07/311 |
| Ex-31 | H | H | 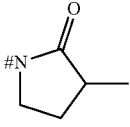 | | 1.19/339 |
| Ex-32 | H | H | | | 91° C. |
| Ex-33 | H | H | 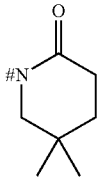 | | 1.22/353 |
| Ex-34 | H | H | 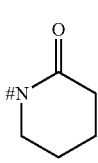 | | 1.11; 325 |

*HPLC: High Performance Liquid Chromatography; HPLC-column Kinetex XB C18 1,7 µ (50 × 2, 1 mm); eluent: acetonitrile/water + 0.1% trifluoroacetic acid (gradient from 5:95 to 100:0 in 1.5 min at 60° C., flow gradient from 0.8 to 1.0 ml/min in 1.5 min). MS: Quadrupol Electrospray Ionisation, 80 V (positive mode). $R_t$: retention time in minutes.

II. BIOLOGICAL EXAMPLES FOR FUNGICIDAL ACTIVITY

The fungicidal action of the compounds of formula I was demonstrated by the following experiments:

A. Glass House Trials

The spray solutions were prepared in several steps: The stock solution were prepared: a mixture of acetone and/or dimethylsulfoxide and the wetting agent/emulsifier Wettol, which is based on ethoxylated alkylphenoles, in a relation (volume) solvent-emulsifier of 99 to 1 was added to 25 mg of the compound to give a total of 5 ml. Water was then added to total volume of 100 ml. This stock solution was diluted with the described solvent-emulsifier-water mixture to the given concentration.

II.1) Curative control of soy bean rust on soy beans caused by *Phakopsora pachyrhizi* Leaves of pot-grown soy bean seedlings were inoculated with spores of *Phakopsora pachyrhizi*. To ensure the success of the artificial inoculation, the plants were transferred to a humid chamber with a relative humidity of about 95% and 20 to 24° C. for 24 hours. The next day the plants were cultivated for 3 days in a greenhouse chamber at 23 to 27° C. and a relative humidity between 60 and 80%. Then the plants were sprayed to run-off with an aqueous suspension, containing the concentration of active ingredient or their mixture as described below. The plants were allowed to air-dry. Then the trial plants were cultivated for 14 days in a greenhouse chamber at 23 to 27° C. and a relative humidity between 60 and 80%. The extent of fungal attack on the leaves was visually assessed as % diseased leaf area.

In this test, the plants which had been treated with 32 ppm of the active compound Ex-1, Ex-4, Ex-5, Ex-6, Ex-7, Ex-8, Ex-9, Ex-10, Ex-11, Ex-12, Ex-13, Ex-14, Ex-15, Ex-16, Ex-18, Ex-19, Ex-21, Ex-22, Ex-23, Ex-28, Ex-30, Ex-31, Ex-32 and Ex-33 showed a diseased leaf area of at most 5%, whereas the untreated plants showed 90% diseased leaf area.

II.2) Protective control of soy bean rust on soy beans caused by *Phakopsora pachyrhizi* Leaves of pot-grown soy bean seedlings were sprayed to run-off with an aqueous suspension, containing the concentration of active ingredient or their mixture as described below. The plants were allowed to air-dry. The trial plants were cultivated for 2 day in a greenhouse chamber at 23 to 27° C. and a relative humidity between 60 and 80%. Then the plants were inoculated with spores of *Phakopsora pachyrhizi*. To ensure the success the artificial inoculation, the plants were transferred to a humid chamber with a relative humidity of about 95% and 20 to 24° C. for 24 h. The trial plants were cultivated for fourteen days in a greenhouse chamber at 23 to 27° C. and a relative humidity between 60 and 80%. The extent of fungal attack on the leaves was visually assessed as % diseased leaf area.

In this test, the plants which had been treated with 32 ppm of the active compound Ex-1, Ex-4, Ex-5, Ex-6, Ex-7, Ex-8, Ex-9, Ex-10, Ex-11, Ex-12, Ex-13, Ex-14, Ex-15, Ex-16, Ex-17, Ex-18, Ex-19, Ex-20, Ex-21, Ex-22, Ex-23, Ex-28, Ex-29, Ex-30, Ex-31, Ex-32 and Ex-33 showed a diseased leaf area of 0%, whereas the untreated plants showed 90% diseased leaf area.

In this test, the plants which had been treated with 16 ppm of the active compound Ex-24, Ex-25, Ex-26 and Ex-27 showed a diseased leaf area of 0%, whereas the untreated plants showed 90% diseased leaf area.

II.3) Curative control of brown rust on wheat caused by *Puccinia recondite*

The first two developed leaves of pot-grown wheat seedling were dusted with spores of *Puccinia recondite*. To ensure the success the artificial inoculation, the plants were transferred to a humid chamber without light and a relative humidity of 95 to 99% and 20 to 24° C. for 24 hours. The next day the plants were cultivated for 3 days in a greenhouse chamber at 20 to 24° C. and a relative humidity between 65 and 70%. Then the plants were sprayed to run-off with an aqueous suspension, containing the concentration of active ingredient or their mixture as described below. The plants were allowed to air-dry. Then the trial plants were cultivated for 8 days in a greenhouse chamber at 20 to 24° C. and a relative humidity between 65 and 70%. The extent of fungal attack on the leaves was visually assessed as % diseased leaf area. In this test, the plants which had been treated with 63 ppm of the active compound Ex-1, Ex-4, Ex-5, Ex-7, Ex-8, Ex-9, Ex-10, Ex-11, Ex-12, Ex-13, Ex-14, Ex-15, Ex-16, Ex-18, Ex-19, Ex-21, Ex-23, Ex-31 and Ex-33 showed a diseased leaf area of at most 2%, whereas the untreated plants showed 90% diseased leaf area.

II.4) Preventative control of brown rust on wheat caused by *Puccinia recondite*

The first two developed leaves of pot-grown wheat seedling were sprayed to run-off with an aqueous suspension, containing the concentration of active ingredient or their mixture as described below. Seven days later the plants were inoculated with spores of *Puccinia recondite*. To ensure the success the artificial inoculation, the plants were transferred to a humid chamber without light and a relative humidity of 95 to 99% and 20 to 24° C. for 24 h. Then the trial plants were cultivated for 6 days in a greenhouse chamber at 20 to 24° C. and a relative humidity between 65 and 70%. The extent of fungal attack on the leaves was visually assessed as % diseased leaf area.

In this test, the plants which had been treated with 63 ppm of the active compound Ex-4, Ex-5, Ex-8, Ex-9, Ex-10, Ex-11, Ex-12, Ex-13 and Ex-14 showed a diseased leaf area of at most 12%, whereas the untreated plants showed 90% diseased leaf area.

The invention claimed is:

1. A method for combating phytopathogenic harmful fungi, which process comprises treating the fungi or materials, plants, soil or seeds to be protected against fungal attack, with an agrochemically effective amount of at least one compound of formula I

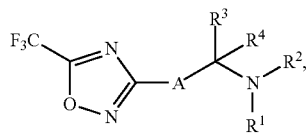

I or an N-oxide, or an agriculturally acceptable salt thereof; wherein:

A is group (A.4), which is unsubstituted

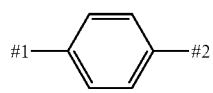

(A.4)

and wherein #1 shall denote the position which is bound to the trifluoromethyloxadiazole moiety and #2 denotes the position, which is connected to the —C($R^3R^4$)—$NR^1R^2$ group;

$R^1$, $R^2$ independently of each other are hydrogen, $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkenyl, C(=O)—($C_1$-$C_6$-alkyl), C(=O)—($C_1$-$C_6$-alkoxy), phenyl-$C_1$-$C_4$-alkyl, heteroaryl-$C_1$-$C_4$-alkyl, phenyl, naphthyl or a 3- to 10-membered saturated, partially unsaturated or aromatic mono- or bicyclic heterocycle, wherein the ring member atoms of said mono- or bicyclic heterocycle include besides carbon atoms further 1, 2, 3 or 4 heteroatoms selected from N, O and S as ring member atoms and wherein 1 or 2 carbon ring member atoms of the heterocycle may be replaced by 1 or 2 groups independently selected from C(=O) and C(=S); and wherein the heteroaryl group in heteroaryl-$C_1$-$C_4$-alkyl is a 5- or 6-membered aromatic heterocycle, wherein the ring member atoms of the heterocyclic ring include besides carbon atoms 1, 2, 3 or 4 heteroatoms selected from N, O and S as ring member atoms; and wherein any of the above-mentioned aliphatic or cyclic groups are unsubstituted or substituted by 1, 2, 3 or up to the maximum possible number of identical or different groups $R^{1a}$; or $R^1$ and $R^2$ together with the nitrogen atom to which they are bound form a saturated or partially unsaturated mono- or bicyclic 3- to 7-membered heterocycle, wherein the heterocycle includes beside one nitrogen atom and one or more carbon atoms no further heteroatom or 1, 2 or 3 further heteroatoms independently selected from N, O and S as ring member atoms; and wherein one or two $CH_2$ groups of the heterocycle may be replaced by one or two groups independently selected from the group of C(=O) and C(=S); and wherein the heterocycle is unsubstituted or substituted by 1, 2, 3, 4 or up to the maximum possible number of identical or different groups $R^{1a}$; wherein $R^{1a}$ is halogen, cyano, $NO_2$, OH, SH, $NH_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cyclo alkyl, $NHSO_2$—$C_1$-$C_4$-alkyl, (C=O)—($C_1$-$C_4$-alkyl), C(=O)—($C_1$-$C_4$-alkoxy) or $C_1$-$C_6$-alkylsulfonyl;

$R^3$ is H, $CH_3$, or $CF_3$; and,
$R^4$ is $CH_3$ or $CF_3$.

2. The method of claim 1, wherein $R^1$ and $R^2$ independently of each other are hydrogen, $C_1$-$C_6$-alkyl, $C_2$-$C_6$-alkenyl, $C_2$-$C_6$-alkynyl, $C_3$-$C_8$-cycloalkyl, C(=O)—($C_1$-$C_6$-alkyl), C(=O)—($C_1$-$C_6$-alkoxy), phenyl-$C_1$-$C_4$-alkyl or phenyl; and wherein any of the aliphatic or cyclic groups are unsubstituted or substituted by 1, 2, 3 or up to the maximum possible number of identical or different groups $R^{1a}$ as defined in claim 1.

3. The method of claim 1, wherein
$R^3$ is H.

4. The method of claim 1, wherein
$R^1$ is hydrogen, $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkenyl, C(=O)—($C_1$-$C_6$-alkyl), C(=O)—($C_1$-$C_6$-alkoxy), phenyl-$C_1$-$C_4$-alkyl, heteroaryl-$C_1$-$C_4$-alkyl, phenyl, naphthyl or a 3- to 10-membered saturated, partially unsaturated or aromatic mono- or bicyclic heterocycle, wherein the ring member atoms of said mono- or bicyclic heterocycle include besides carbon atoms further 1, 2, 3 or 4 heteroatoms selected from N, O and S as ring member atoms and wherein 1 or 2 carbon ring member atoms of the heterocycle may be replaced by 1 or 2 groups independently selected from C(=O) and C(=S); and wherein the heteroaryl group in heteroaryl-$C_1$-$C_4$-alkyl is a 5- or 6-membered aromatic heterocycle, wherein the ring member atoms of the heterocyclic ring include besides carbon atoms 1, 2, 3 or 4 heteroatoms selected from N, O and S as ring member atoms; and wherein any of the above-mentioned aliphatic or cyclic groups are unsubstituted or substituted by 1, 2, 3 or up to the maximum possible number of identical or different groups $R^{1a}$ as defined in claim 1; and $R^2$ is $C(=O)-(C_1-C_6$-alkyl) or $C(=O)-(C_1-C_6$-alkoxy).

5. The method of claim 1, wherein
$R^1$ and $R^2$ together with the nitrogen atom to which they are bound form a saturated or partially unsaturated mono- or bicyclic 3- to 7-membered heterocycle, wherein the heterocycle includes beside one nitrogen atom and one or more carbon atoms no further heteroatom or 1, 2 or 3 further heteroatoms independently selected from N, O and S as ring member atoms; and wherein one or two $CH_2$ groups of the heterocycle may be replaced by one or two groups independently selected from the group of $C(=O)$ and $C(=S)$; and wherein the heterocycle is unsubstituted or carries 1, 2, 3, 4 or up to the maximum possible number of identical or different groups $R^{1a}$; wherein
$R^{1a}$ is halogen, cyano, $NO_2$, OH, SH, $NH_2$, $C_1-C_6$-alkyl, $C_1-C_6$-haloalkyl, $C_1-C_6$-alkoxy, $C_1-C_6$-haloalkoxy, $C_1-C_6$-alkylthio, $C_1-C_6$-haloalkylthio, $C_3-C_8$-cycloalkyl, $NHSO_2-C_1-C_4$-alkyl, $(C=O)-(C_1-C_4$-alkyl), $C(=O)-(C_1-C_4$-alkoxy) or $C_1-C_6$-alkylsulfonyl.

6. The method of claim 1, wherein $R^1$ and $R^2$ independently of each other are hydrogen, $C_1-C_6$-alkyl, $C_2-C_6$-alkenyl, $C_2-C_6$-alkynyl, $C_3-C_8$-cycloalkyl, $C(=O)-(C_1-C_6$-alkyl), $C(=O)-(C_1-C_6$-alkoxy), phenyl-$C_1-C_4$-alkyl or phenyl; and wherein any of the aliphatic or cyclic groups are unsubstituted or substituted by 1, 2, 3, 4 or up to the maximum possible number of identical or different groups $R^{1a}$ as defined in claim 1.

7. An agrochemical mixture comprising at least one compound of the formula I

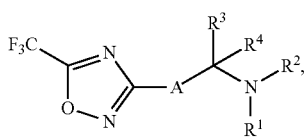

(I)

or an N-oxide, or an agriculturally acceptable salt thereof; wherein:
A is group (A.4), which is unsubstituted

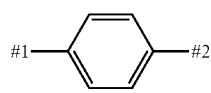

(A.4)

and wherein #1 shall denote the position which is bound to the trifluoromethyloxadiazole moiety and #2 denotes the position, which is connected to the $-C(R^3R^4)-NR^1R^2$ group;
$R^1$, $R^2$ independently of each other are hydrogen, $C_1-C_6$-alkyl, $C_2-C_6$-alkenyl, $C_2-C_6$-alkynyl, $C_3-C_6$-cycloalkyl, $C_3-C_6$-cycloalkenyl, $C(=O)-(C_1-C_6$-alkyl), $C(=O)-(C_1-C_6$-alkoxy), phenyl-$C_1-C_4$-alkyl, heteroaryl-$C_1-C_4$-alkyl, phenyl, naphthyl or a 3- to 10-membered saturated, partially unsaturated or aromatic mono- or bicyclic heterocycle, wherein the ring member atoms of said mono- or bicyclic heterocycle include besides carbon atoms further 1, 2, 3 or 4 heteroatoms selected from N, O and S as ring member atoms and wherein 1 or 2 carbon ring member atoms of the heterocycle may be replaced by 1 or 2 groups independently selected from $C(=O)$ and $C(=S)$; and wherein the heteroaryl group in heteroaryl-$C_1-C_4$-alkyl is a 5- or 6-membered aromatic heterocycle, wherein the ring member atoms of the heterocyclic ring include besides carbon atoms 1, 2, 3 or 4 heteroatoms selected from N, O and S as ring member atoms; and wherein any of the above-mentioned aliphatic or cyclic groups are unsubstituted or substituted by 1, 2, 3 or up to the maximum possible number of identical or different groups $R^{1a}$; or $R^1$ and $R^2$ together with the nitrogen atom to which they are bound form a saturated or partially unsaturated mono- or bicyclic 3- to 7-membered heterocycle, wherein the heterocycle includes beside one nitrogen atom and one or more carbon atoms no further heteroatom or 1, 2 or 3 further heteroatoms independently selected from N, O and S as ring member atoms; and wherein one or two $CH_2$ groups of the heterocycle may be replaced by one or two groups independently selected from the group of $C(=O)$ and $C(=S)$; and wherein the heterocycle is unsubstituted or substituted by 1, 2, 3, 4 or up to the maximum possible number of identical or different groups $R^{1a}$; wherein
$R^{1a}$ is halogen, cyano, $NO_2$, OH, SH, $NH_2$, $C_1-C_6$-alkyl, $C_1-C_6$-haloalkyl, $C_1-C_6$-alkoxy, $C_1-C_6$-haloalkoxy, $C_1-C_6$-alkylthio, $C_1-C_6$-haloalkylthio, $C_3-C_8$-cycloalkyl, $NHSO_2-C_1-C_4$-alkyl, $(C=O)-(C_1-C_4$-alkyl), $C(=O)-(C_1-C_4$-alkoxy) or $C_1-C_6$-alkylsulfonyl;
$R^3$ is H, $-CH_3$, or $CF_3$; and,
$R^4$ is $CH_3$ or $CF_3$;
and at least one further pesticidally active substance selected from the group consisting of herbicides, safeners, fungicides, insecticides, and plant growth regulators.

8. An agrochemical composition, which comprises an auxiliary and at least one compound of the formula I,

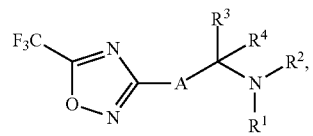

(I)

or an N-oxide, or an agriculturally acceptable salt thereof; wherein:
A is group (A.4), which is unsubstituted

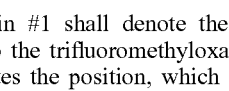

(A.4)

and wherein #1 shall denote the position which is bound to the trifluoromethyloxadiazole moiety and

2 denotes the position, which is connected to the —C($R^3R^4$)—N$R^1R^2$ group;

$R^1$, $R^2$ independently of each other are hydrogen, $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkenyl, C(=O)—($C_1$-$C_6$-alkyl), C(=O)—($C_1$-$C_6$-alkoxy), phenyl-$C_1$-$C_4$-alkyl, heteroaryl-$C_1$-$C_4$-alkyl, phenyl, naphthyl or a 3- to 10-membered saturated, partially unsaturated or aromatic mono- or bicyclic heterocycle, wherein the ring member atoms of said mono- or bicyclic heterocycle include besides carbon atoms further 1, 2, 3 or 4 heteroatoms selected from N, O and S as ring member atoms and wherein 1 or 2 carbon ring member atoms of the heterocycle may be replaced by 1 or 2 groups independently selected from C(=O) and C(=S); and wherein the heteroaryl group in heteroaryl-$C_1$-$C_4$-alkyl is a 5- or 6-membered aromatic heterocycle, wherein the ring member atoms of the heterocyclic ring include besides carbon atoms 1, 2, 3 or 4 heteroatoms selected from N, O and S as ring member atoms; and wherein any of the above-mentioned aliphatic or cyclic groups are unsubstituted or substituted by 1, 2, 3 or up to the maximum possible number of identical or different groups $R^{1a}$; or $R^1$ and $R^2$ together with the nitrogen atom to which they are bound form a saturated or partially unsaturated mono- or bicyclic 3- to 7-membered heterocycle, wherein the heterocycle includes beside one nitrogen atom and one or more carbon atoms no further heteroatom or 1, 2 or 3 further heteroatoms independently selected from N, O and S as ring member atoms; and wherein one or two $CH_2$ groups of the heterocycle may be replaced by one or two groups independently selected from the group of C(=O) and C(=S); and wherein the heterocycle is unsubstituted or substituted by 1, 2, 3, 4 or up to the maximum possible number of identical or different groups $R^{1a}$; wherein $R^{1a}$ is halogen, cyano, $NO_2$, OH, SH, $NH_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $NHSO_2$—$C_1$-$C_4$-alkyl, (C=O)—($C_1$-$C_4$-alkyl), C(=O)—($C_1$-$C_4$-alkoxy) or $C_1$-$C_6$-alkylsulfonyl;

$R^3$ is H, $CH_3$, or $CF_3$; and $R^4$ is $CH_3$ or $CF_3$.

9. The agrochemical composition according to claim 8, wherein the auxiliary is selected from the group consisting of anionic, cationic and non-ionic surfactants.

10. Seed treated with the agrochemical composition of claim 8 in an amount of the compound of the formula I, or an N-oxide, or an agriculturally acceptable salt thereof, of from 0.1 g to 10 kg per 100 kg of seed.

* * * * *